United States Patent [19]
Bramlet

[11] Patent Number: 5,827,285
[45] Date of Patent: Oct. 27, 1998

[54] MULTIPIECE INTERFRAGMENTARY FIXATION ASSEMBLY

[76] Inventor: Dale G. Bramlet, 2044 Brightwaters Blvd., St. Petersburg, Fla. 33703

[21] Appl. No.: 764,265

[22] Filed: Dec. 12, 1996

Related U.S. Application Data

[63] Continuation-in-part of Ser. No. 576,813, Dec. 21, 1996, abandoned.
[51] Int. Cl.[6] ............................... A61B 17/00; A61F 5/04
[52] U.S. Cl. .............................. 606/60; 606/72; 606/73; 606/104; 606/105; 411/81; 411/166
[58] Field of Search .............................. 606/73, 72, 104, 606/105; 411/81, 166

[56] References Cited

U.S. PATENT DOCUMENTS

| | | | |
|---|---|---|---|
| 4,456,005 | 6/1984 | Lichty | 606/60 |
| 4,858,601 | 8/1989 | Glisson | 606/73 |

Primary Examiner—Michael Buiz
Assistant Examiner—Julian W. Woo
Attorney, Agent, or Firm—Rudnick & Wolfe

[57] ABSTRACT

A multipiece interfragmentary fixation assembly for interconnecting bone fragments across a fracture therebetween. The fixation assembly comprises a first axially elongated fastener having external threading for anchoring the first fastener into the bone substance of the first bone fragment. The first fastener defining a coaxial throughbore with internal threading extending along the length thereof. The fixation assembly also includes a second fastener attachable in non-movable relation relative to the second bone fragment. An elongated connector operably interconnects the fasteners such that rotation of the connector draws the fasteners and the bone fragments attached to each into a predetermined compressive relationship relative to each other. A retaining apparatus prevents the connector from inadvertently turning and thereby maintains the predetermined compressive relationship between the fasteners and the bone fragments to promote healing of the fracture.

50 Claims, 39 Drawing Sheets

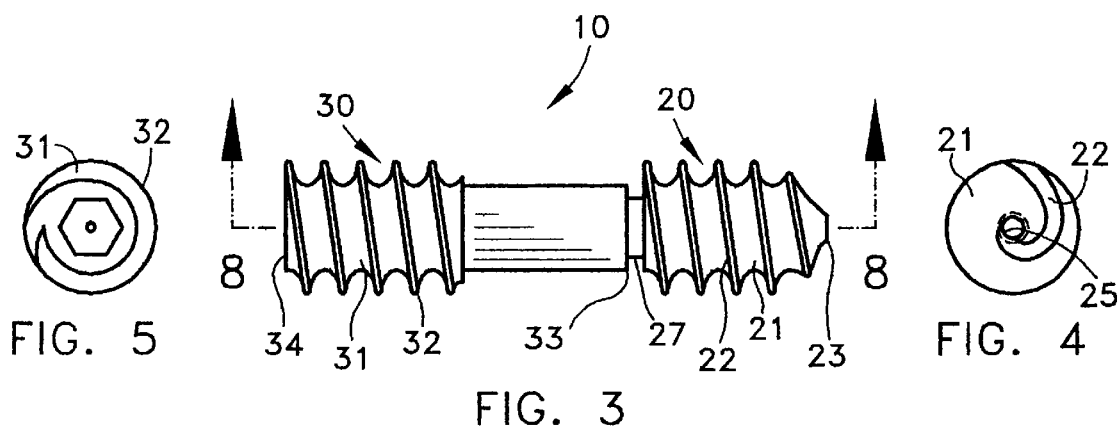
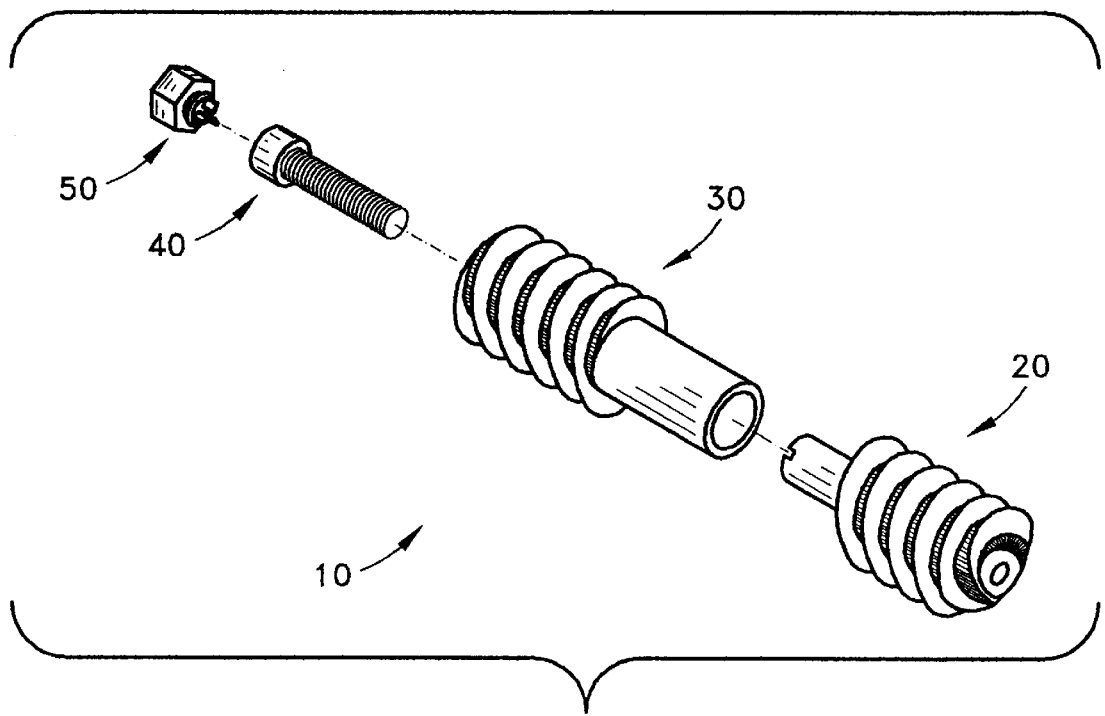

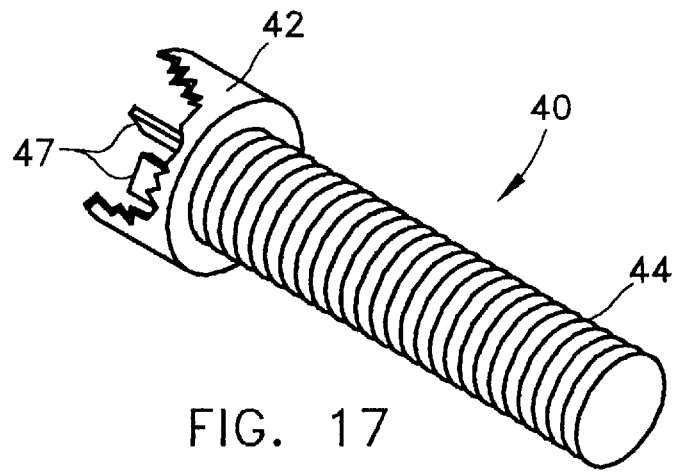
FIG. 17
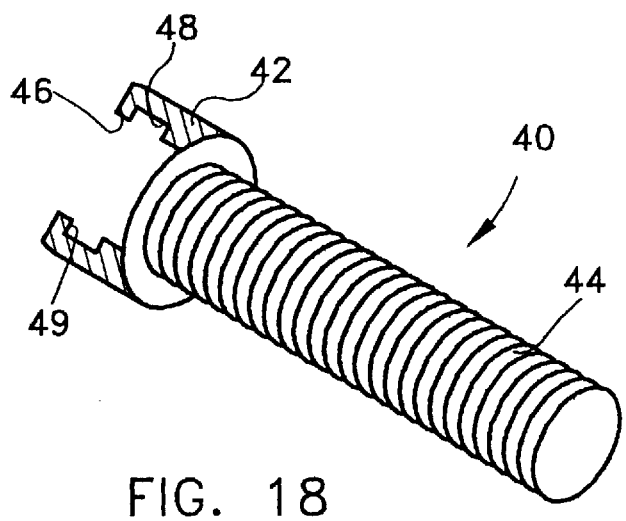
FIG. 18
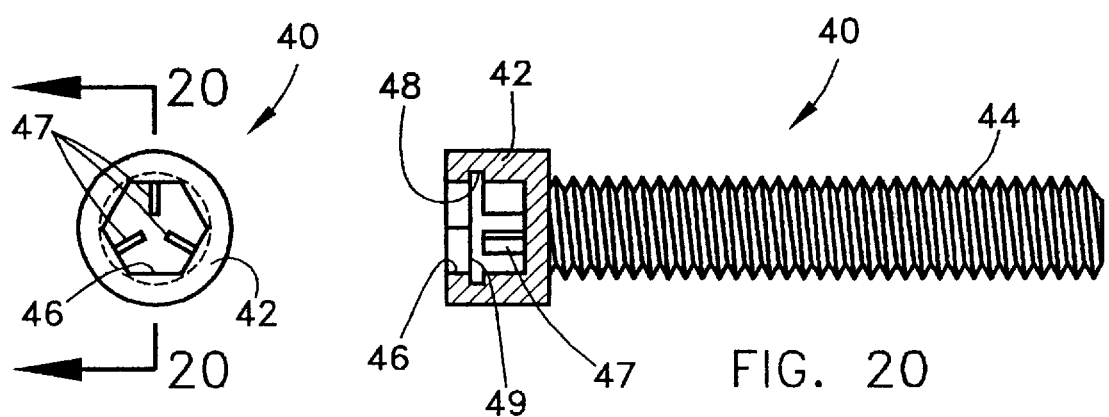
FIG. 19
FIG. 20

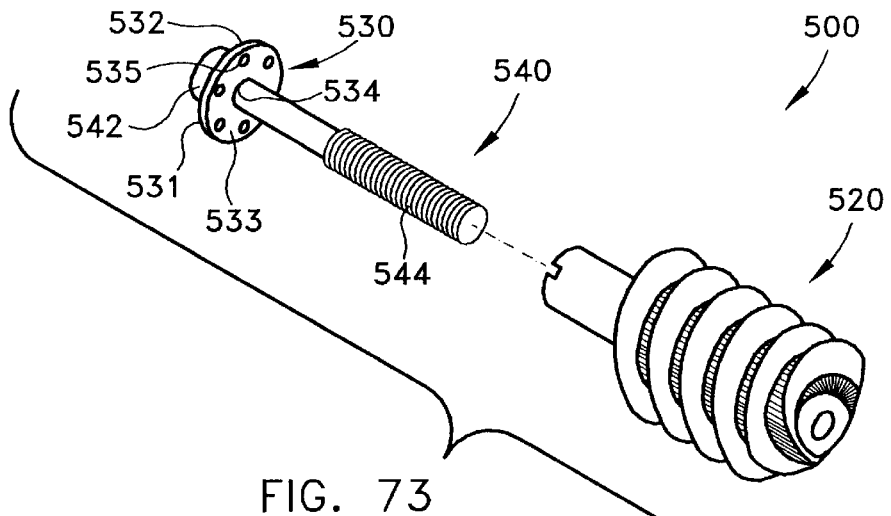
FIG. 73
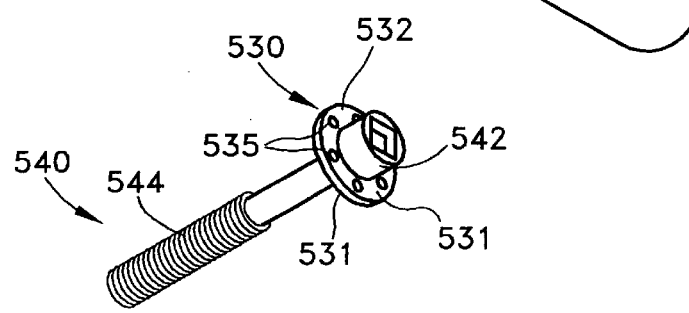
FIG. 74
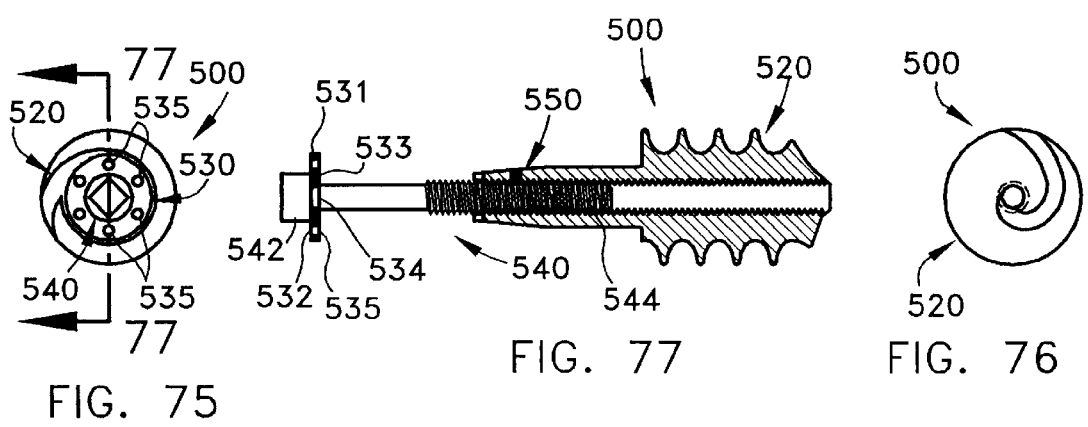
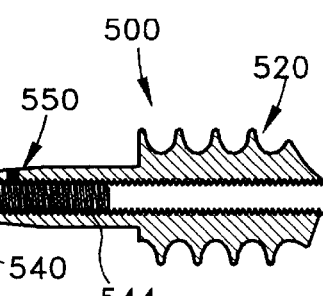
FIG. 75
FIG. 77
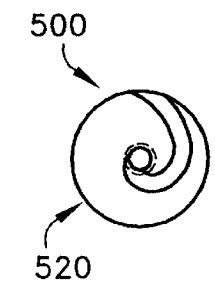
FIG. 76

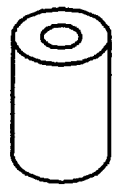
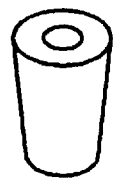
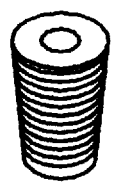
FIG. 91   FIG. 92   FIG. 93
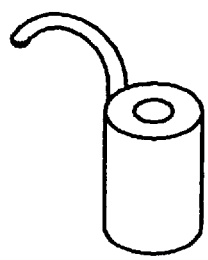
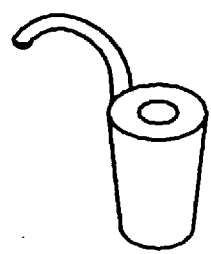
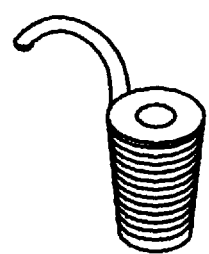
FIG. 94   FIG. 95   FIG. 96
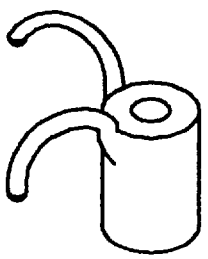
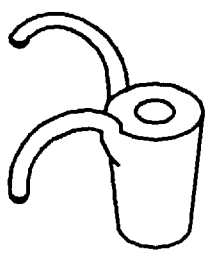
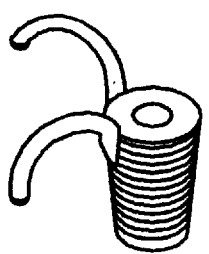
FIG. 97   FIG. 98   FIG. 99

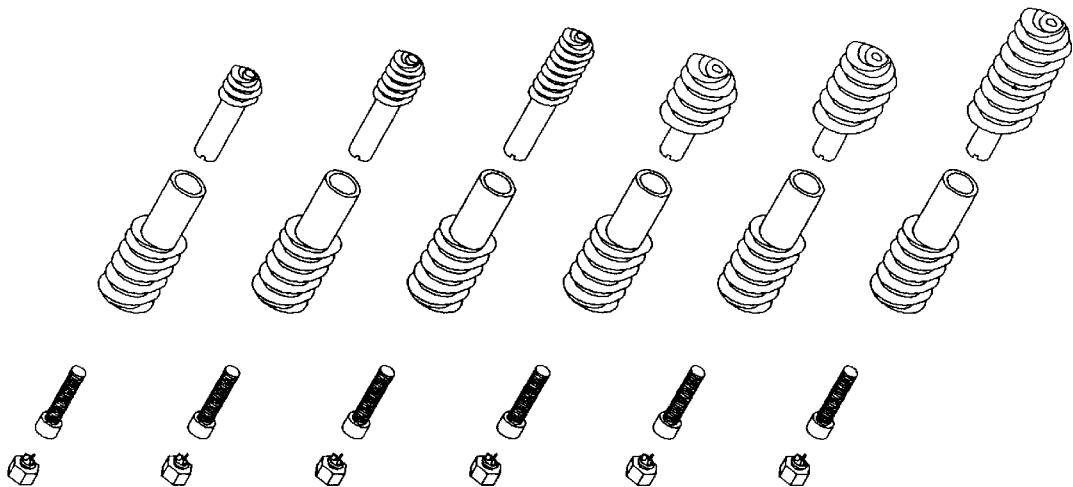
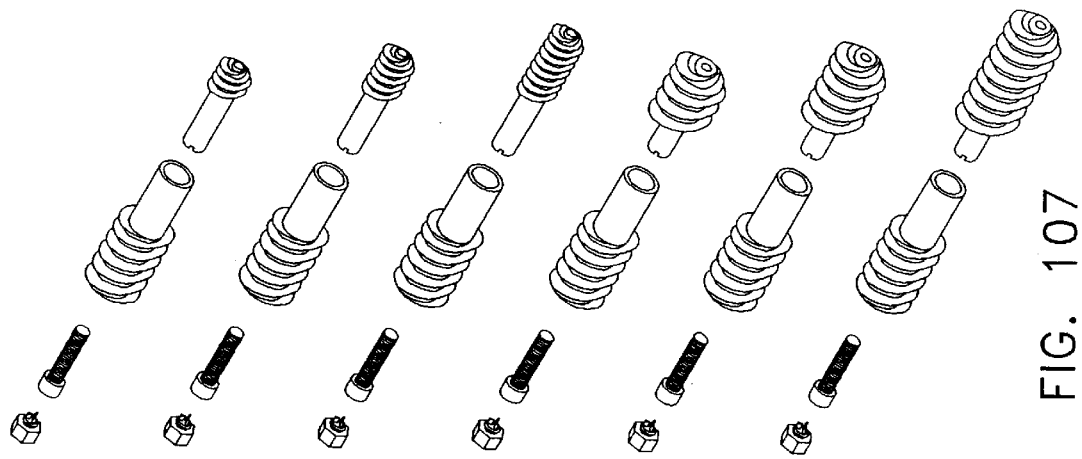
FIG. 107
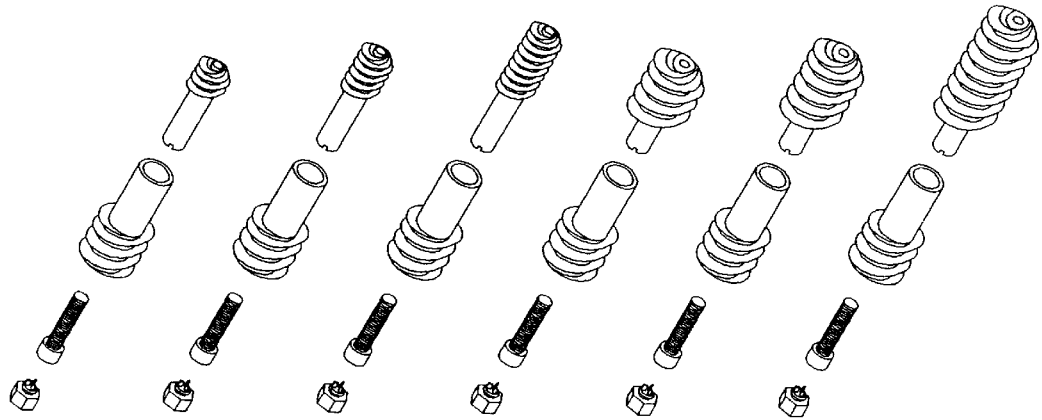

5,827,285

MULTIPIECE INTERFRAGMENTARY FIXATION ASSEMBLY

RELATED APPLICATIONS

This patent application is a continuation-in-part of my patent application Ser. No. 08/576,813 filed Dec. 21, 1996, now abandoned.

FIELD OF THE INVENTION

The present invention generally relates biological medical instruments and, more particularly, to a multipiece fixation assembly for interconnecting two pieces of a fractured bone under a predetermined and substantially constant compressive force to promote optimum healing of the fracture.

BACKGROUND OF THE INVENTION

The scaphoid represents one of the most frequently injured bones of the wrist. Unfortunately, it also represents one of the most frequently missed wrist injuries. Scaphoid fractures commonly result from an acute dorsiflexion stress such as occurs following a fall on an outstretched hand. If the fracture is initially recognized and properly immobilized, healing rates approaching 95% have been documented for acute fractures.

Fractures have historically been divided into three types based on the level of the fracture. The fractures through the middle one-third of the scaphoid are most common and occur approximately 70% of the time. Fractures through the proximal one-third of the scaphoid occur approximately 20% of the time, and are at greater risk for developing avascular necrosis. Fractures of the distal scaphoid are very uncommon, occurring approximately 10% of the time, and have a very high union rate with proper immobilization.

Fractures of the scaphoid have also been classified based on the orientation of the fracture line in relation to the longitudinal axis of the scaphoid. The majority of fractures occur transverse to the longitudinal axis of the scaphoid and will sometimes heal with as little as six weeks of immobilization. Horizontal oblique fractures are the second most common, occurring approximately 35% of the time, with vertical oblique fractures being quite rare. Both horizontal and oblique fractures can require a longer period of immobilization to obtain union between the fractured bone fragments. The vast majority of scaphoid fractures will heal with twelve weeks of immobilization, and anything past four months may be regarded as a delayed union. Fractures that have not healed within six months of immobilization from the time of injury, and that have definite sclerotic margins at the fracture lines, can be considered to be an established non-union of the fractured bone fragments.

Several factors contribute to the ability of the fractured bone fragments to be united with each other. The unique anatomy of the blood supply to the carpal navicular is one factor. The degree of injury to the supporting soft tissues and the degree of displacement of the bone fragments relative to each other are other factors. Associated carpal instability is still another factor that must be considered when evaluating the likelihood of the bone fractures to unite relative to each other. Early detection and proper immobilization of the fractured scaphoid are still further factors that contribute to the development of the non-union of the fractured scaphoid segments.

Scaphoid fractures have been classified as stable based upon a minimal degree of displacement at the fracture site. Fractures that are displaced greater than one millimeter are considered to be unstable and are frequently accompanied by rupture of the supporting ligaments of the scaphoid. Increased displacement is typically associated with a higher incidence of non-union of the fractured bone fragments.

Failure to disclose, to reduce, or to adequately immobilize scaphoid fractures is directly responsible for development of delayed union or non-union. Technetium bone scans have been used both for early detection of scaphoid fractures and for detection of scaphoid pseudarthrosis. Trispiral tomography is helpful both in the initial detection of scaphoid fractures, in evaluating the degree of displacement of the fractured bone fragments relative to each other, and in determining union following bone grafting of a non-union or a prolonged period of cast immobilization.

Significant limitations of wrist motion can occur secondary to a scaphoid non-union. Without intervention, patient's with an established scaphoid non-union have an extremely high likelihood of developing an arthritic wrist. This most commonly follows the pattern of Scapho-Lunate Advanced Collapse (SLAC) with sparing of the radio-lunate joint and radius-proximal scaphoid fragment joint. Patient's with an asymptomatic scaphoid non-union should be advised the development of an arthritic wrist is highly probable.

Surgical fastener assemblies for rejoining and holding fractured or broken bone fragments in place are known in the art. Where cross-fixation of the bone fragments is required, maintaining and holding both bone fragments in compression relative to each other enhances the likelihood of success of the surgical procedure. As will be readily appreciated, a gap or displacement between the adjacent bone fragments is highly undesirable because fibrous tissue will grow therebetween before the fracture can heal with boney unions. Thus delaying the healing process. Space between the bone fragments also tends to allow the bone fragments to shift or displace relative to each other thus adding to the retardation of the healing process. On the other hand, if the surgeon is able to bring the bone fragments into contact relative to each other and maintain the bone fragments in contact with each other, the space between the bone fragments is minimized and the bone fragments are inhibited from shifting, thus promoting the healing process. Moreover, when the bone fragments heal in proper alignment relative to each other, there is a reduction in the risk of the secondary development of arthritis.

In many instances, the entire fastener assembly is wholly arranged or completely buried within the bone substance. Screws commonly used in securing fractured bone fragments to each other typically include an elongated threaded portion that terminates, toward one end, in an enlarged head portion. Certain surgical repair procedures, however, do not lend themselves to use of a headed bone screw. For example, a headed bone screw does not lend itself to those situations wherein there is inadequate bone substance or stock to allow countersinking of the enlarged head portion of the bone screw. Providing a countersunk configuration in the bone substance, however, also often destroys cartilage needed in a joint for its proper functioning.

Moreover, severe problems can result from use of these types of bone screws. That is, after the biological operation has been completed, the bone tissue about the bone screw tends to recede by boney resorption thereby allowing the bone screw to loosen, thus destroying the compressive force that maintains the bone fragments in close proximity relative to each other. Besides those problems mentioned above that can result when the bone fragments are not maintained in close proximity, and as will be appreciated, as the bone screw loosens, it is not uncommon for the head portion to protrude through the skin of the patient having such fracture. This, of course, results in significant additional problems including the possibility of additional surgery requirements to correct the problem. Additional surgery means additional expenses for the patient and loss of employment during the surgical recuperation period.

Responding to the above noted problems, attempts have been made to improve upon bone screws. U.S. Pat. No. 4,175,555 issued Nov. 27, 1979 to T. J. Herbert discloses a bone screw device for interconnecting two bone fragments under compression and which lacks the drawbacks associated with a headed bone screw and allows the bone screw device to be totally or wholly embedded within the bone substance of the patient. The Herbert device has screw threads which are like handed but of different pitch on its leading and trailing ends. More specifically, the pitch of the threads at the leading end exceeds the thread pitch at the trailing end. Thus, the leading end of the screw advances at a slightly faster rate than the trailing end thereby causing the bone fragments to be brought together under some degree of compression.

While offering certain advantages over heretofore known bone screw devices, the Herbert device also has certain drawbacks. Because of the relatively small difference in the thread pitch between the leading and trailing threads, the Herbert device has a limited ability to draw the fractured bone fragments that are not already proximate to each other into compressive relationship relative to each other. Moreover, and because the thread pitch of the leading and trailing threads differs, the diameter of the leading threads must be smaller than the core of the root diameter of the trailing threads to prevent binding of the screw. Accordingly, the leading end of the Herbert screw has a lesser or weaker bone material purchase than does the trailing end. This lesser degree of bone purchase can have an adverse effect on the ability of the bone screw to remain fixed in the bone when subjected to pulling forces applied thereagainst.

The surgeon generally judges the proper compressive force to be applied between the fractured bone components by "feeling" for tightness. The Herbert device, however, does not afford the surgeon this luxury. When the Herbert device is used to secure two bone fragments across the fracture thereof, the trailing threads are not and cannot be tapped into the bone fragment because of thread synchronization problems. Accordingly, during use of the Herbert device, the surgeon feels only the resistance necessary to allow penetration of the trailing threads into the bone thus resulting in the possibility of sub-optimal repairs.

U.S. Pat. No. 4,858,601 to R. R. Glisson discloses a compression screw assembly including a pair of externally threaded members that are interconnected in an axially fixed and abutting relationship relative to each other by a spindle. After insertion of the spindle through both members of the screw assembly, the spindle is fixedly connected to one of the threaded members. By turning the screw assembly in a first direction, the surgeon can thread both screw members and the spindle into the bone substance of the fragments that are to be repaired or joined to each other. Thereafter, one screw member is rotated or turned in an opposite direction and relative to the other screw member to draw the bone fragments toward each other.

Surgical repair of fractured bones involves complicated procedures. The Glisson device only serves to furthermore complicate an already complex surgical procedure. That is, with the Glisson device the surgeon must initially rotate or turn the screw assembly in a first direction and then turn only one screw member of the assembly in a second direction, opposite to the first direction. As will be appreciated by those skilled in the art, initially turning both screws in a first direction and then turning one of the screw members in a second and opposite direction detracts from the ability of the screw assembly to establish and maintain a strong purchase with the bone substance or tissue of fragmented bones that are to be joined to each other. Nothing is provided on the Glisson device, however, for preventing the screw members from rotating relative to each other for a prolonged time period after the screw assembly is initially inserted into the patient. Thus, the setting between the screw members initially selected by the surgeon can readily be lost or destroyed simply by the screw members turning relative to each other. Furthermore, nothing associated with the Glisson device suggests to a person skilled in the art how it could be used to facilitate reattachment of ligamentous tissues to bone fragments.

Frequently, with an acute hyperextension injury to the wrist the scaphoid will not fracture but instead a series of ligamentous damage can occur about the wrist of the patient. The volar wrist ligaments certainly contribute to instability about the wrist. Many are of the opinion, however, that the dorsal scapholunate interosseous ligament is a primary constraining force that, when ruptured, leads to disassociation between the scaphoid and lunate bones. Failure to reconstruct this ligament can lead to the development of progressive arthritis about the wrist.

Various techniques and devices have been proposed to reconstruct the ligaments between the scaphoid and lunate bone. One common technique involves arthroscopy of the wrist and the percutaneous pinning between the scaphoid and lunate that have been manipulated back into the proper positions. With a failure of this technique, which frequently occurs in clinical situations, there is scapholunate instability. A number of soft tissue ligamentous techniques for reconstructing these ligaments have been described, but these known techniques frequently lead to failure, due to the reconstructed ligaments stretching out and losing their degree of stability between the two bones. This can result in progressive loss of the integrity of the reconstructed ligament, resulting in the development of a scapholunate advanced collapse pattern of the wrist. Alternative techniques such as fusing the scaphoid bone to the lunate have been fraught with a high rate of non-union.

Although the Herbert device is not particularly suited for ligament reattachment, alternative anchoring devices have been proposed to attach ligaments to bone. There are a paucity of devices, however, wherein a ligament, with an attached fragment of bone can be readily reattached to a bone using a compression screw. A toggle bolt type mechanism does not allow for adequate reattachment of a bony fragment with sufficient tolerances to enable adequate strength of compression of the bone ligament construct to effect a rigid enough period of compression to heal within the channel created in the scaphoid when a bone ligament bone construct is utilized to reconstruct the scaphoid lunate interosseous ligament.

Thus, there remains a need and a desire for a bone screw assembly that permits first and second bone fragments to be interconnected to each other under compression and wherein the proper compression between the bone fragments is measured by the surgeon's feel of the bone screw. Moreover, there is a clear need for a more universal system for facilitating the reattachment of ligaments to bone fragments.

SUMMARY OF THE INVENTION

In view of the above, and in accordance with the present invention, there is provided a multipiece interfragmentary fixation assembly that is wholly contained within the bone substance such that it can serve a number of useful purposes for dealing with fractures and reconstructive procedures in the field of orthopedic surgery. The interfragmentary fixation assembly of the present invention includes a first axially elongated fastener that defines an elongated axis and has external threading for anchoring the first fastener into a first bone fragment and a second fastener that is attachable in non-movable relation relative to a second bone fragment. The first fastener defines a coaxial opening with internal threading extending along at least a portion of the length thereof. The coaxial opening permits endwise passage of a guide therethrough thus facilitating proper placement and anchoring of the first fastener within the first bone fragment.

To allow the first and second fasteners and thereby the first and second bone fragments to be drawn toward and ultimately into compressive relationship relative to each other, the fixation assembly further includes an elongated connector that interconnects the first and second fasteners and allows the surgeon to adjust the proper compressive force between the bone fragments as a function of "feel." The connector includes a head portion and a shank portion. The head portion of the connector is configured to accommodate a driving tool. The shank portion of the connector includes external threading corresponding to the internal threading on the first fastener. The shank portion of the connector is configured to extend endwise through the second fastener and into threaded engagement with the first fastener while the head portion of the connector operably engages with the second fastener such that rotation of the connector draws the first and second fasteners toward and into compressive relationship relative to each other. The connector is prevented from inadvertently rotating relative to the fastener with which a threaded connection is established thereby maintaining the predetermined compressive relationship between the bone fragments and thereby promoting healing and union therebetween.

In a preferred form of the invention, the first fastener is formed from a bone compatible material form the class of: stainless steel, titanium, or a cobalt chromium molybdenum alloy. The external threading on the first fastener has a substantially uniform pitch. To promote engagement with bone substance, a leading end of the first fastener preferably has a pointed end configuration. A trailing end of the first fastener is configured to accommodate a driving tool capable of turning the first fastener such that the external threading thereon threadably engages and anchors the first fastener within the bone fragment. In a most preferred form of the invention, the first fastener has a reduced diameter portion axially extending from the terminal end of the threading. The reduced portion of the first fastener has an axially tapering configuration along an outer surface thereof.

According to one aspect of the present invention, the second fastener has an axially elongated configuration with external threading for anchoring the second fastener within the bone substance of the second bone fragment. The external threading on this preferred form of the invention has a substantially uniform pitch along the length thereof that corresponds to the pitch on the external threading of the first fastener. The second fastener is formed from a bone compatible material from the class including: stainless steel, titanium, or a cobalt chromium molybdenum alloy. In this embodiment of the invention, the second fastener has a coaxial opening extending endwise therethrough for allowing the second fastener to be initially guided into generally axial alignment and operable relationship with said first fastener. The trailing end of this embodiment of the second fastener is configured to accommodate a driving tool capable of turning the second fastener such that the external threading threadably engages and anchors the second fastener into the bone substance of the second bone fragment.

In a most proffered form of the present invention, the axial bore defined by the second fastener has a first lengthwise portion that opens to a trailing end of the second fastener and a second lengthwise portion that opens to a leading end of the second fastener. The second lengthwise portion of the second fastener has a configuration that is specifically sized such that only the threaded shank portion of the connector can endwise extend therethrough. Moreover, the second portion of the axial bore in the second fastener is specifically configured to coact with the axially tapering extension on the first fastener. Preferably, the configuration of the axial bore defined by the second fastener has an axially tapering configuration that complements the tapered configuration on the first fastener whereby effecting axially alignment of the fasteners and thereby the fractured bone fragments relative to each other thus promoting the healing process.

According to another aspect of the present invention, the second fastener comprises a member configured with a generally concave shaped section that is generally centralized between multiple prongs extending radially away from the central section. An apertured hemi-spherically shaped element is adapted to be seated for rocking movement within the central section of the member. The shank portion of the connector is configured to endwise extend through the member and the element into threaded engagement with the first fastener. The head portion of the connector being operably engagable with the element such that rotation of the connector draws the member and the first fastener and the respective bone fragments engaged by each toward and into compressive relationship relative to each other such that minimal tissue growth is effected between the fractured bone fragments whereby enhancing union of the bone fragments to each other. In this preferred form of the invention, the central section of the member defines an enlarged opening that permits the member to rock relative to the connector and the element thereby enhancing the attachment of the prongs to the second bone fragment.

To promote the attachment of ligament pieces to bone fragments, another aspect of the present invention configures the second fastener as an apertured disk. The apertured disk fits about the shank portion of the connector and operably engages an underside of the head portion of the connector to permit relative rotation therebetween. The disk has a series of apertures that permit the second bone fragment to be secured thereto as with stitches, sutures, or the like.

Still another aspect of the present invention concerns configuring the second fastener to maintain the second bone fragment in a hole or bore provided by the surgeon in the first bone fragment. To accomplish such ends, the second fastener is configured as an elongated member having first and second ends and an axial bore for allowing the shank portion of the connector to extend endwise through the second fastener and into threaded engagement with the first fastener. In this embodiment of the invention, the member of the second fastener further includes a rigid bone fragment retainer extending radially away from the elongated member. In a most preferred form of the invention, the elongated member has a generally cylindrical configuration between opposite ends thereof. Alternatively, the elongated member of the second fastener has a frusto-conical configuration between opposite ends thereof.

The interfragmentary fixation assembly of the present invention can also be utilized for arthrodesis of small joints.

An alternative variation for use in a joint where flexion is desired, such as a proximal interphalangeal or metacarpal joint, involves alternatively configuring the second fastener as a plate-like member that fixedly attaches to the second bone fragment. The plate-like member has upper and lower generally parallel surfaces with an indentation or depression having a closed margin defined by the periphery of the plate-like member and including a wall depending at an acute angle relative to the upper surface of the plate-like member. The indentation or depression fits into a recess formed in the bone fragment to which the plate-like member is attached to allow smooth gliding of tendons overlying the second fastener. The wall defined by the indentation is apertured to allow the shank portion of the connector to endwise extend into threaded engagement with the internal threading on said first fastener. The wall of the indentation maintains the head portion of the connector on an opposite side of the plate from the first fastener. Moreover, in a preferred form of the invention, the upper and lower surfaces of the plate-like member have a generally convex configuration that generally parallels the outer surface configuration of the bone fragment to which this second fastener is attached.

In the preferred form of the invention, the enlarged head portion of the connector operably engages with the second fastener thus causing the second fastener to move toward and, ultimately, into a compressive relationship with the first fastener in response to its threaded engagement with and rotation of the connector relative to the first fastener. The free end of the connector's head portion is preferably configured with a socket for releasably accommodating a driving tool.

According to the present invention, the connector is inhibited from inadvertently rotating relative to the fastener with which a threaded connection is established. In one form of the invention, a retaining apparatus or element having a cross-sectional configuration that complements the cross-sectional configuration of the first portion of the axial bore defined by the second fastener and opening to the trailing end of the second fastener serves to engage with the connector in a manner preventing rotation of the connector relative to the fastener with which the connector has a threaded engagement. Moreover, in this form of the invention, the element or retainer apparatus is releasably coupled to the head portion of the connector thereby preventing rotation of the connector and, thus, maintaining substantially constant predetermined compressive force initially established by the surgeon between the first and second fasteners so as to promote the healing process.

Alternatively, the retaining apparatus of the present invention comprises a non-metal insert preferably arranged lengthwise along the internal threading of the first fastener. In this embodiment of the invention, as the connector threadably engages and moves along the length of the internal threading on the first fastener it likewise engages with the non-metal insert thereby inhibiting inadvertent rotation of the connector after the surgeon establishes that degree of compression desired between the first and second fasteners. Because the insert prevents inadvertent rotation of the connector, the first and second fasteners are maintained under the predetermined compressive force established by the surgeon thus maintaining the fractured bone pieces not only in compression but also in close proximity thereby enhancing the healing process.

In still another form of the invention, an internal locking thread form is defined within the fastener with which the connector is threadably fastened so as to prevent the connector from inadvertently rotating relative to the fastener. That is, the internal locking thread form coacts with the conventional external threading on the connector to prevent inadvertent rotation of the connector thereby maintaining the predetermined compression between the fasteners and, thus, the bone fragments, as a function of the surgeon's "feel". Moreover, the use of an internal locking thread form simplifies the design of the fixation assembly.

According to another aspect of the present invention, there is provided an interfragmentary compression kit. The kit includes a collection of first axially elongated fasteners. Each fastener in the collection has a different length from other like fasteners in the collection. Each fastener in the collection can be further distinguished by the diameter of the threaded portion. The different shapes and sizes of the fasteners in the collection allows the surgeon to chose which particular fastener has the desired maximum purchase with the particular bone fragment being repaired. The kit further includes a series of second fasteners. To provide the surgeon with the appropriate fastener, each fastener in the series of second fasteners is different from other fasteners in the series of fasteners to provide the surgeon with the maximum ability to interchange fasteners and select the best for the particular bone fragment being repaired. Moreover, a set of elongated connectors are likewise arranged in the kit. The connectors in the kit have different configurations from other connectors in the set. Suffice it to say, the kit of the present invention allows the surgeon to chose the appropriate fasteners and connectors for the particular surgical procedure and patient.

The present invention advantageously provides a biological fixation assembly that is wholly embedded within the bone substance of the patient and permits the bone fragments to be interconnected to each other with abutting surfaces of the bone fragments arranged in close proximity and under a predetermined level of compression relative to each other. The interfixation assembly further includes a retaining apparatus that maintains that predetermined level of compression between the bone components thus promoting healing. Moreover, the fixation assembly of the present invention prevents the connector from inadvertently becoming unthreaded thus eliminating the problem of the connector backing out of the bone and potentially protruding through the skin of the patient. In that embodiment of the invention wherein both fasteners are threaded, the fixation assembly has equal pull out strength on opposite sides of the fracture. Another important feature of the present invention is that the level of compression is adjustable to provide the surgeon with the proper "feel" of tightness.

These and other objects, aims and advantages of the present invention will become readily apparent from the following detailed description, appended claims, and the following drawings.

DETAILED DESCRIPTION OF THE DRAWINGS

FIG. 3 is an enlarged elevational view of that embodiment of the multipiece interfragmentary fixation assembly shown in FIG. 2;

FIG. 4 is a right end view of the multipiece interfragmentary fixation assembly illustrated in FIG. 3;

FIG. 5 is a left end view of the multipiece interfragmentary fixation assembly illustrated in FIG. 4;

FIG. 6 is a perspective view of components of the fixation assembly illustrated in longitudinally spaced relation relative to each other;

FIG. 17 is a perspective view, with sections being broken away, of a connector forming part of the present invention;

FIG. 18 is another perspective view, with sections being broken away, of the connector illustrated in FIG. 17;

FIG. 19 is a left end view of the connector illustrated in FIGS. 17 and 18;

FIG. 20 is an elevational view of the connector with a head portion thereof being shown in section as seen along line 20—20 of FIG. 19;

FIG. 57 is a longitudinal sectional view of the fixation assembly of the present invention with component parts, including the fastener shown in FIG. 56, illustrated in axially spaced relation relative to each other and with;

FIG. 73 is a perspective view of another alternative embodiment of the interfragmentary fixation assembly with component parts thereof shown in axially spaced relation relative to each other;

FIG. 74 is a perspective view of the alternative embodiment of a second fastener used in combination with the fixation assembly schematically illustrated in FIG. 73;

FIG. 75 is a left end view of the alternative embodiment of fixation assembly shown in FIG. 73;

FIG. 76 is a right end view of the fixation assembly illustrated in FIG. 73;

FIG. 77 is a partial sectional view taken along line 77—77 of FIG. 75;

FIGS. 91 through 99 are perspective views of alternative embodiments of the second fastener similar to that illustrated in FIG. 87;

FIG. 107 is an illustration of an interfragmentary fixation kit according to one aspect of the present invention.

DETAILED DESCRIPTION OF THE PRESENT INVENTION

Figure 1:
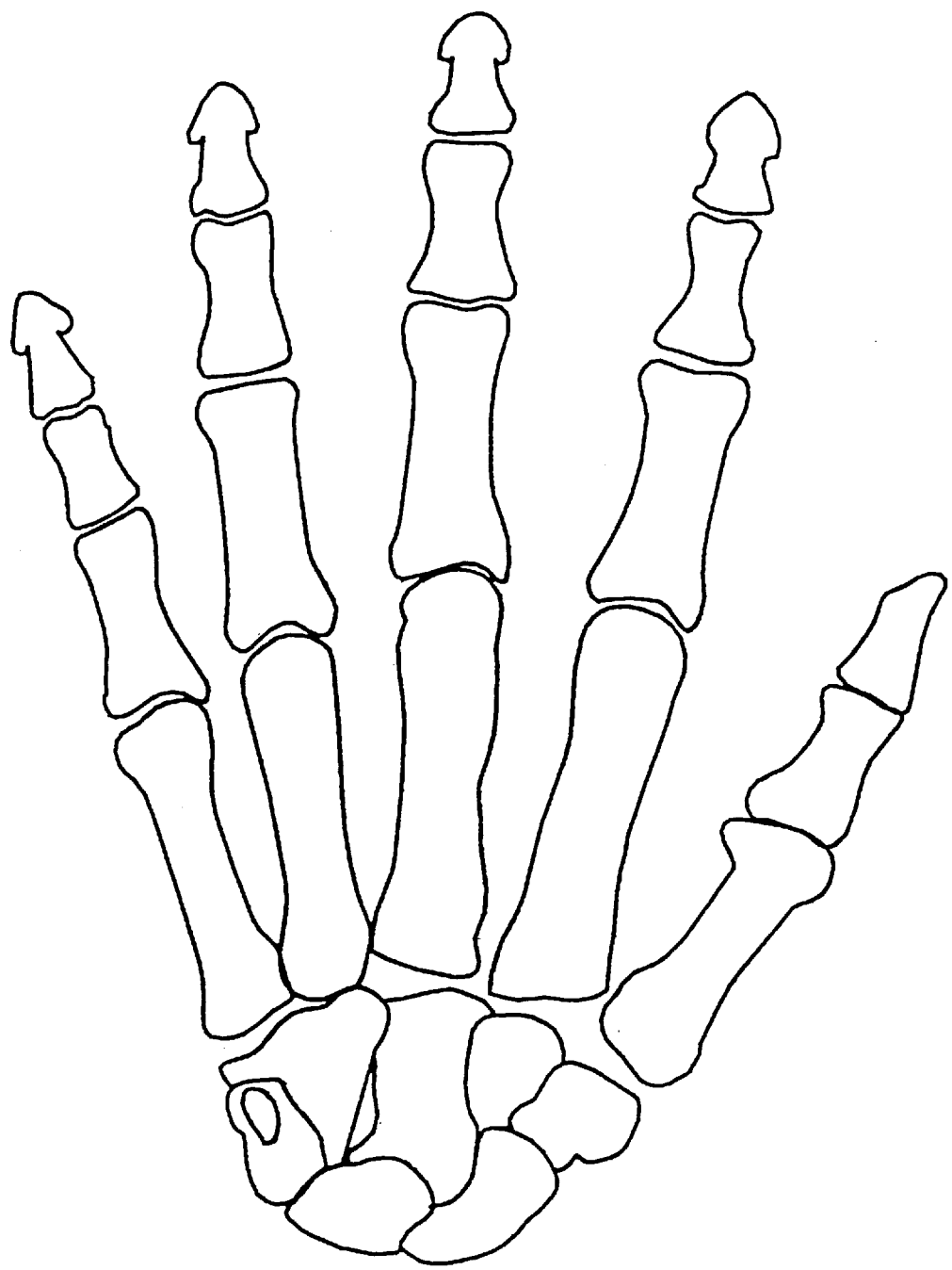
FIG. 1 is a schematic representation of the various bones contained in the hand of a patient.

While the present invention is susceptible of embodiment in various forms, there are shown in the drawings and will hereinafter be described preferred embodiments of the invention with the understanding that the present disclosure is to be considered as setting forth exemplifications of the invention which are not intended to limit the invention to the specific embodiments illustrated.

Referring now to the drawings, wherein like reference numerals refer to like parts throughout several views, in FIG. 1, there is schematically represented a scaphoid which is fractured into two fragments. The scaphoid fracture is used as a model wherein the interfragmentary fixation assembly of the present invention can be utilized to compress the bone fragments under a predetermined force selected by the surgeon to enhance healing thereof. As would be appreciated, the present invention is equally applicable to other situations beyond repair of the scaphoid as will be described below.

Figure 2:
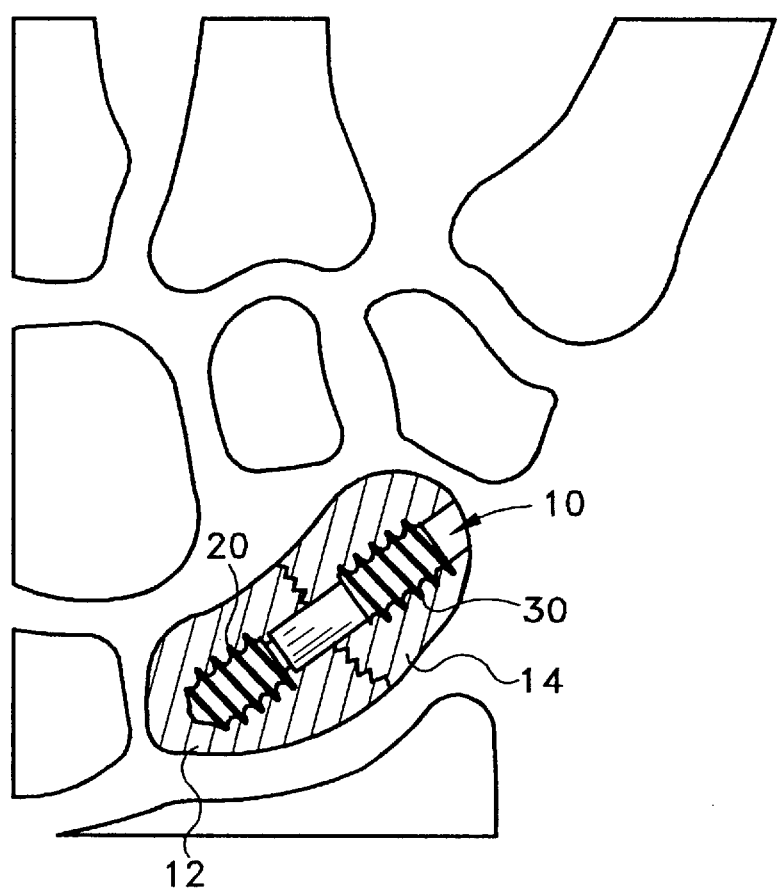
FIG. 2 is an enlarged cross section view similar to FIG. 1 showing an embodiment of a multipiece interfragmentary fixation assembly according to the present invention wholly embedded within a fractured scaphoid.

One embodiment of the multipiece interfragmentary fixation assembly is shown in FIG. 2 as being wholly embedded within the scaphoid and is represented in its entirety by reference numeral 10. As illustrated in FIG. 2, a leading portion of the fixation assembly 10 is secured or attached to the bone substance of the proximal fragment 12 of the scaphoid while a trailing portion of the fixation assembly 10 is secured or attached to the bone substance of a distal fragment 14 of the scaphoid.

As shown in FIG. 3, the multipiece interfragmentary fixation assembly 10 includes first and second fasteners 20 and 30, respectively. Returning to FIG. 2, the first fastener 20 is attachable in nonmovable relation to the first bone fragment 12 and the second fastener 30 is attachable in nonremovable relation to the second bone fragment 14.

As shown in FIGS. 3 and 4, the first fastener 20 comprises an elongated member 21 having external threading 22 extending axially rearwardly from a generally pointed end 23 thereof. In this preferred form of the invention, the first fastener 20 has a trailing end 24 that cooperates and combines with the second fastener 30 to affect alignment of the fractured bone fragments 12 and 14 (FIG. 2).

Turning to FIGS. 3 and 5, in this illustrated embodiment of the invention, the second fastener 30 comprises an elongated member 31 having external threading 32 extending axially forwardly from a trailing end 34 thereof. In this preferred form of the invention, the second fastener 30 has a leading end 33 that combines with the first fastener 20 to affect alignment of the fractured bone fragments 12 and 14 (FIG. 2).

Figure 7:
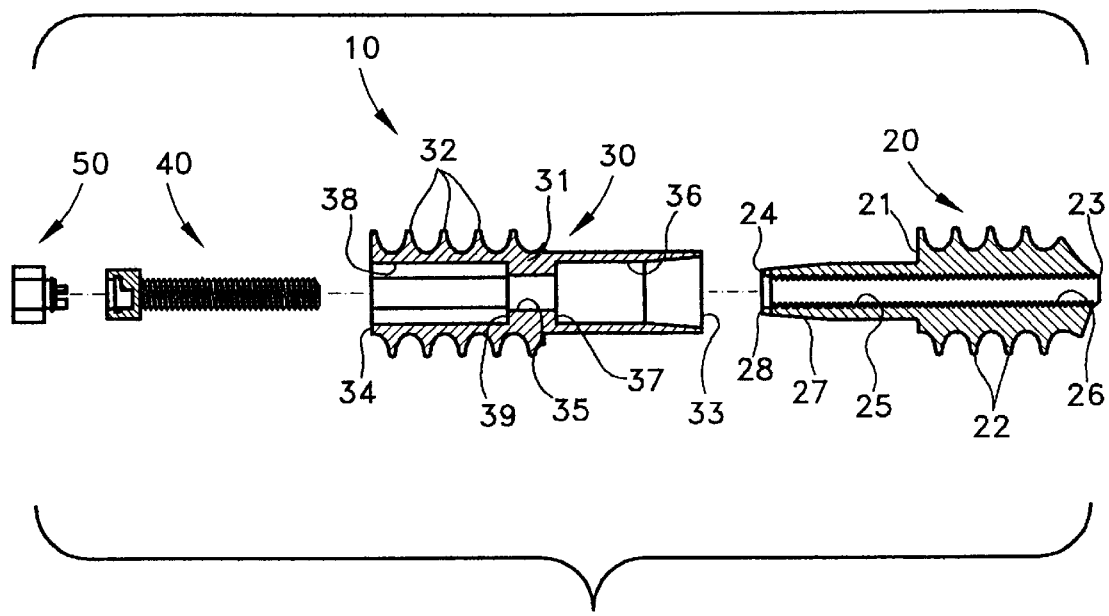
FIG. 7 is a longitudinal sectional view of component parts of the present invention shown in separated relation relative to each other.
Figure 8:
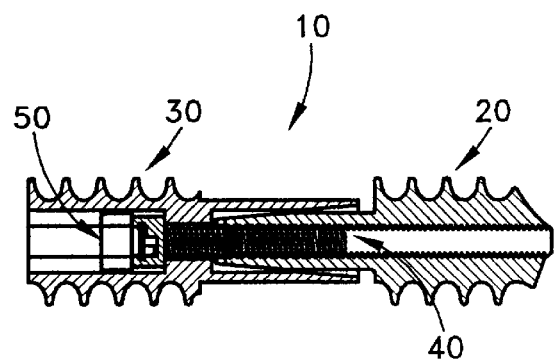
FIG. 8 is a sectional view taken along line 8—8 of FIG. 3.

As shown in FIGS. 6, 7 and 8, the multipiece interfragmentary fixation assembly 10 further includes any elongated threaded connector 40 and an apparatus 50 for inhibiting inadvertent or free turning rotation of the connector 40. The connector 40 serves to operably interconnect the first and second fasteners 20 and 30, respectively, under a predetermined compressive force selected by the surgeon. Notably, the compressive force selected by the surgeon is developed as a result of the surgeon's "feel" as the first and second fasteners 20 and 30, respectively and the bone fragments 12 and 14 connected to each fastener are drawn into confronting relation relative to each other. The fixation assembly 10 is further configured to maintain the compressive force between the first and second fasteners 20 and 30, respectively, and the bone fragments attached to each thereby preventing inadvertent turning movement of the connector so as to promote union between the bone fragments and healing of the fracture.

Figure 9:
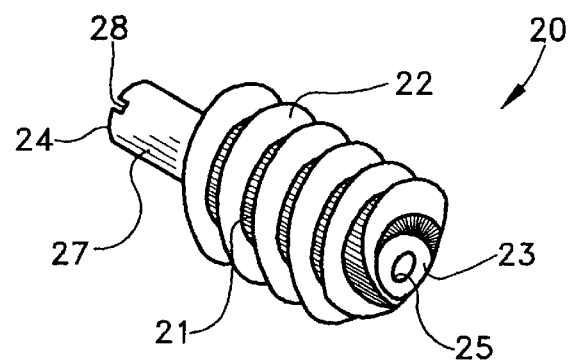
FIG. 9 is a perspective view of one component fastener forming part of the present invention.

Turning to FIG. 9, the elongated member 21 of the first fastener 20 is preferably fabricated from a biocompatible material selected from a class comprised of: titanium, stainless steel, or a cobalt chromium molybdenum alloy. The external threading 22 extends axially lengthwise of member 21 and has a uniform pitch between leading and trailing ends thereof. In the illustrated embodiment of the fastener 20, the external threading 22 axially extends for a distance equal to about one-half the distance between the proximal and distal ends 23 and 24, respectively, of member 21.

Figure 10:
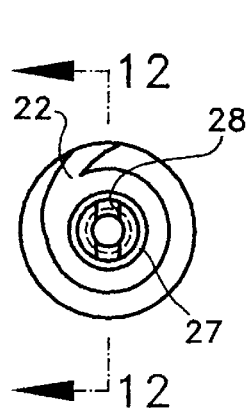
FIG. 10 is a left end view of the component fastener illustrated in FIG. 9.
Figure 12:
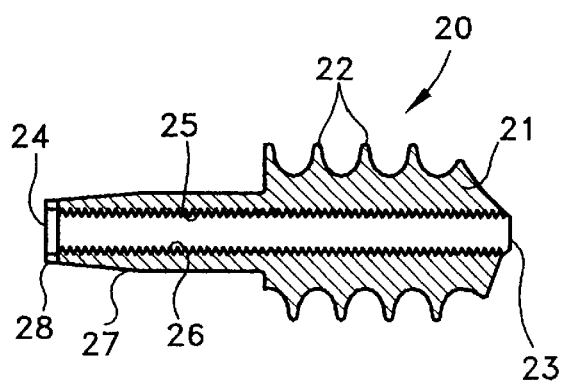
FIG. 12 is a sectional view taken along line 12—12 of FIG. 10.
Figure 11:
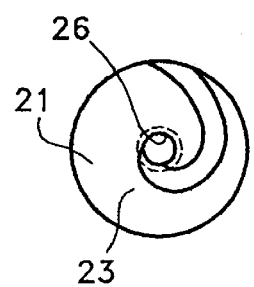
FIG. 11 is a right end view of the component fastener illustrated in FIG. 9.

As shown in FIGS. 9 through 12, member 21 defines an axial bore 25 that extends through member 21 and opens to the leading and trailing ends 23 and 24, respectively, thereof. For at least a portion and preferably for the entire length thereof, bore 25 defines conventional internal threading 26 which is preferably of uniform pitch. The internal threading 26 axially extends from the trailing end 24 toward the leading end 23 for at least a portion of the length of the axial bore 25. In a most preferred form of the invention, the internal threading 26 extends along the entire axial length of bore 25. As shown in FIGS. 9, 10 and 12, in this preferred form of fastener 20, member 21 further defines an axial lengthwise section or portion 27 having a diameter which is less than or reduced from the diameter of the threaded portion 22 and extending axially and forwardly from the trailing end 24 of the fastener 20. Moreover, this reduced diameter portion 27 of fastener 20 has an axially tapered configuration. In the illustrated embodiment, the diameter of the reduced portion 27 of member 21 increases as a function of the distance measured from the trailing end 24 of the fastener 20.

Fastener 20 is further configured to allow a suitable driving tool (FIG. 34) to be releasably connected to the fastener 20 to affect the rotation thereof. In the illustrated embodiment shown in FIGS. 9, 10 and 12, the trailing end 24 of member 21 is configured with a transverse slot 28 that releasably accommodates a flat tip of a screwdriver or other suitable tool. As will be appreciated, other tool receiving configurations would likewise suffice as long as such configurations are capable of releasably accommodating a driving tool capable of turning the first fastener 20 such that the external threading 22 threadably engages with the respective bone fragment thereby anchoring the fastener to the respective bone fragment.

Figure 13:
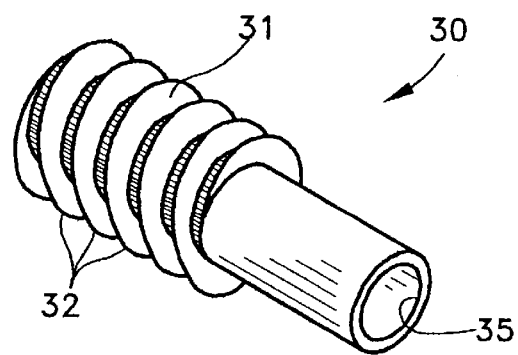
FIG. 13 is a perspective view of another component fastener forming part of the present invention.

Turning to FIG. 13, the elongated member 31 of the second fastener 30 is preferably fabricated from a biocompatible material preferably selected from the class comprised of: titanium, stainless steel, or a cobalt chromium molybdenum alloy. As shown in FIGS. 13 through 16, member 31 of the second fastener defines an axial bore 35 that extends through member 31 and opens to the leading and trailing ends 33 and 34 thereof. Notably, the external threading 32 extending along the axial length of member 31 has a uniform pitch between leading and trailing ends thereof. It is also important to note, the external threading 32 extending axially along the length of the second fastener 30 is like-handed and generally corresponds to the pitch of the threading of the external threading 22 extending axially along the first fastener 20. In the illustrated embodiment of the second fastener 30, the external threading 32 axially extends for a distance equal to about one-half the length between distal and proximal ends 33 and 34, respectively, of the second fastener 30. Suffice it to say, that the external threading 22, 32 on the fasteners 20, 30, respectively, has a relatively course pitch such that a substantive holding force or purchase will be developed when the fasteners are threadably secured within the respective bone fragments.

Figure 16:
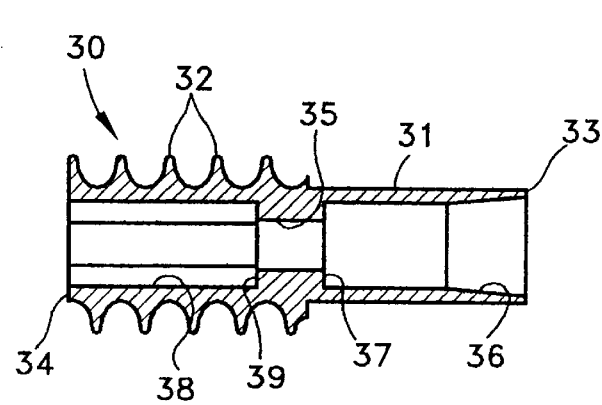
FIG. 16 is a longitudinal sectional view taken along line 16—16 of FIG. 14.
Figure 15:
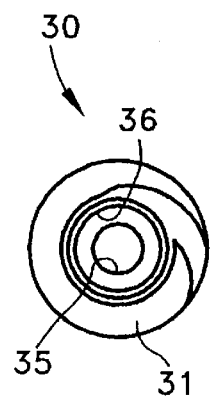
FIG. 15 is a right end view of the component fastener illustrated in FIG. 13.

As shown in FIGS. 15 and 16, the axial bore 35 defined by member 31 includes a counterbore portion 36 extending axially away from the proximal or leading end 33 of fastener 30. As shown in FIG. 16, in this embodiment of the second fastener 30, the counterbore portion 36 has a larger inside diameter than is the inside diameter of bore 35 thus defining an annular shoulder 37 axially spaced a predetermined distance inwardly from the leading end 33 of fastener 30. Moreover, the counterbore portion 36 of bore 35 has an inside diameter generally equal to the outside diameter of the reduced diameter portion 27 of the first fastener 20. In a most preferred form of the second fastener, the counterbore portion 36 has an axially tapering configuration that compliments the axially tapering configuration on the reduced diameter portion 27 of the first fastener 20.

Figure 14:
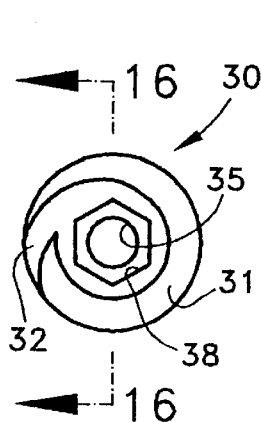
FIG. 14 is a left end view of the component fastener illustrated in FIG. 13.

As shown in FIGS. 14 and 16, the axial bore 35 defined by member 31 also includes a counterbore portion 38 extending axially inwardly from the distal or trailing end 34 of fastener 30. In this preferred form of the second fastener 30, the counterbore portion 38 has a specific cross-sectional shape extending the axial length thereof. In this particular embodiment of the second fastener, the counterbore portion 38 has a generally hexagonal cross-sectional shape extending inwardly from the distal or trailing end 34 of the second fastener 30. The cross-sectional shape of the counterbore 38, of course, could be other than hexagonal, such as triangular, square, octagonal or pentagonal without detracting from the spirit and scope of the present invention. Amongst other features described below, the counterbore portion 38 is configured to allow a suitable driving tool (FIG. 36) to be releasably connected to the fastener 30 such that the driving tool is capable of turning the second fastener 30 such that the external threading 32 threadably engages with the second bone fragment 14 of the scaphoid. Because of the different cross-sectional configurations of bore 35 and counterbore 38, however, a shoulder 39 (FIG. 16) is defined therebetween.

One form of connector 40 is illustrated in FIGS. 17 through 20. As shown, the connector includes an enlarged head portion 42 and an axially elongated externally and conventionally threaded shank portion 44. The external threading on the shank portion 44 of connector 40 has a pitch that corresponds to the pitch of the internal threading 26 extending along at least a portion of the bore 25 defined by the first fastener 20. In the embodiment of the connector 40 shown, the diameter of the shank portion 44 is specifically sized to fit endwise through the smallest diameter portion of the axial bore 35 defined by the second fastener 30 so as to allow the proximal end of the shank portion 44 of connector 40 to threadably engage with the internal threading 26 of the axial bore 25 of the first fastener 20. Moreover, the head portion 42 is sized to endwise move through the counterbore portion 38 of the second fastener and engage the shoulder 39 that acts as a stop for the connector 40.

As shown in FIG. 19, the head portion 42 of connector 40 defines a blind socket 46 that opens to a distal end of the head portion 42 of connector 40 and is configured to releasably accommodate a driving tool (FIG. 43) capable of imparting turning movement to the connector 40. In a most preferred form, the blind socket 46 of connector 40 has a hexagonal cross-sectional configuration although other like configurations would equally suffice.

In the illustrated form, the head portion 42 of the connector 40 includes at least one finger 47 that axially projects through the blind socket 46 and toward the open end thereof. In a most preferred form of the connector 40, and as shown in FIG. 19, three equally spaced and axially extending fingers 47 are provided in the blind socket 46 and project toward the open end thereof.

The head portion 42 of the connector 40 preferably further includes an annular channel 48 having a diameter that is greater than the blind socket opening 46. Notably, the annular channel 48 defines an outer surface 49 that is spaced a predetermined distance from the blind or closed end of cavity 46.

The means for retaining the connector 40 against rotation and thereby maintaining the predetermined compressive relationship between the fasteners 20, 30 and, thus, the bone fragments secured to each, can take a myriad of different forms. The retainer apparatus 50 is arranged in operable combination with and holds the connector 40 against rotation thereby maintaining the predetermined compressive relationship between the fasteners 20, 30. One form of retainer apparatus 50 is illustrated in FIGS. 21 through 24. As shown, the retainer apparatus 50 includes an element 52 formed from a biocompatible material selected from the class comprised of: nylon or an ultra high molecular weight polyethylene. In its illustrated form, element 52 of retainer apparatus 50 includes a body portion 54 with a cross-sectional configuration that generally corresponds to the cross-sectional configuration of the counterbore 38 in the second fastener 30. Suffice it to say, the body portion 54 of element 52 has a cross-sectional configuration that operates in combination with the cross-sectional configuration of the counterbore 38 to prevent rotation of the element 52 relative to the second fastener 30.

Figure 21:
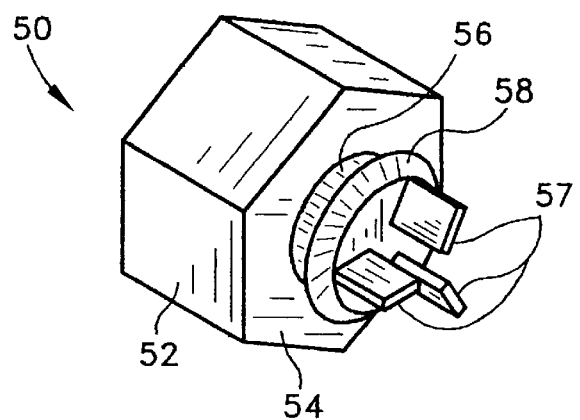
FIG. 21 is a perspective view of one embodiment of a retainer apparatus forming part of the present invention.
Figure 22:
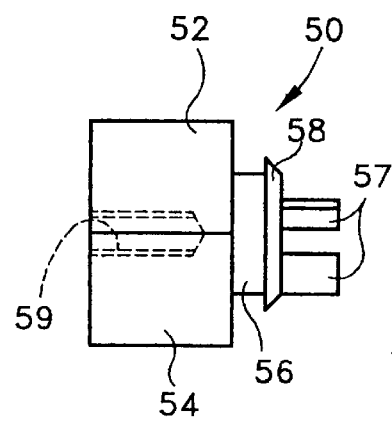
FIG. 22 is an elevational view of the retainer apparatus illustrated in FIG. 21.
Figure 24:
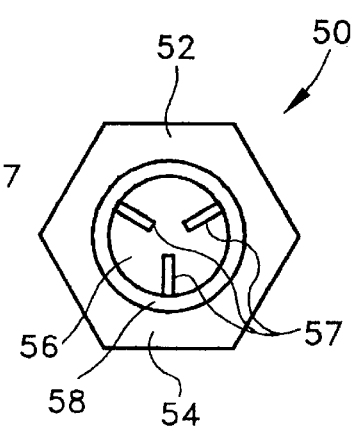
FIG. 24 is a right end view of the retainer apparatus illustrated in FIG. 22.

In the illustrated embodiment of the retainer apparatus 50 shown in FIGS. 21, 22 and 24, element 52 further includes an axial extension 56 that projects from a proximal end thereof. At its free end, the axial extension 56 defines at least one finger 57 that is adapted to cooperate and combine with finger 47 defined in the blind socket 46 of the connector 40. In a most preferred form of the invention, and as shown in FIG. 24, the axial extension 56 of element 52 includes three equally spaced fingers 57 that project from the free end of the axial extension 56.

Figure 23:
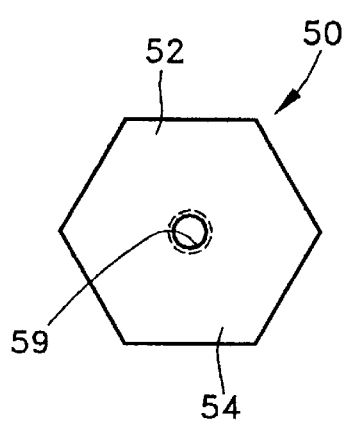
FIG. 23 is a left end view of the retainer apparatus illustrated in FIG. 22.

In this particular illustrated form of the retainer apparatus 50, the axial extension 56 furthermore includes an annular ring 58 having an outside diameter that is generally equal to the inside diameter of the channel 48 of connector 40. Preferably, the annular ring 58 on the axial extension 56 is formed from a pliable material that is biocompatible with the bone and tissue substance wherein the fixation assembly of the present invention is adapted for use. Suffice it to say, the annular ring 58 is formed of a material that allows the ring to compress and subsequently snap into the channel 48 and combine with surface 49 of channel 48 to prevent inadvertent axial displacement of the element 52 toward the trailing end 34 of the second fastener 30. As shown in FIGS. 22 and 23, element 52 further defines a threaded bore 59 for purposes to be described hereinafter.

Figure 25:
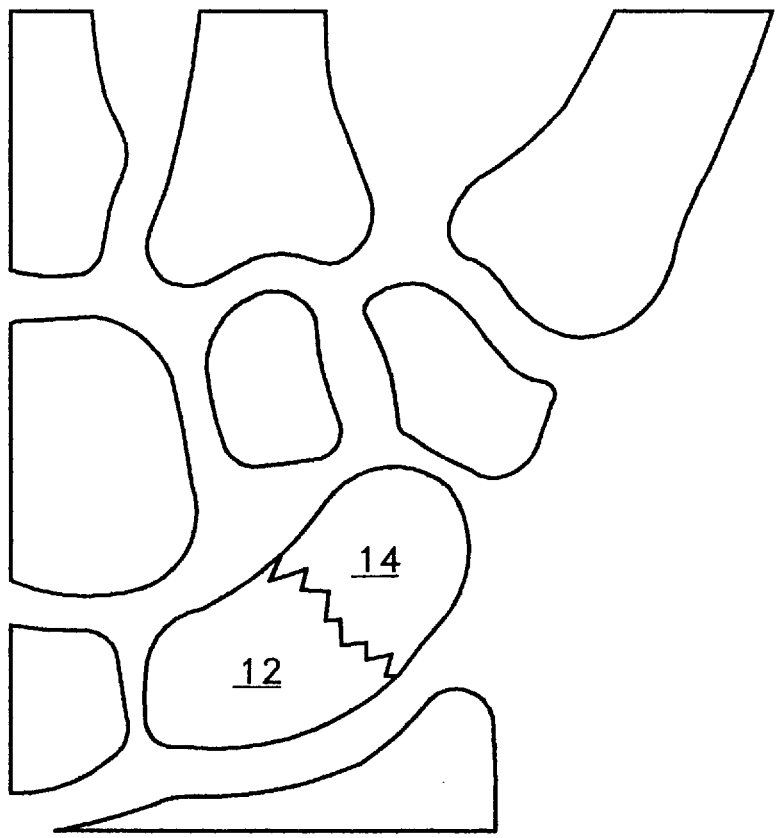
FIG. 25 is an enlarged schematic view of a fractured scaphoid bone.
Figure 26:
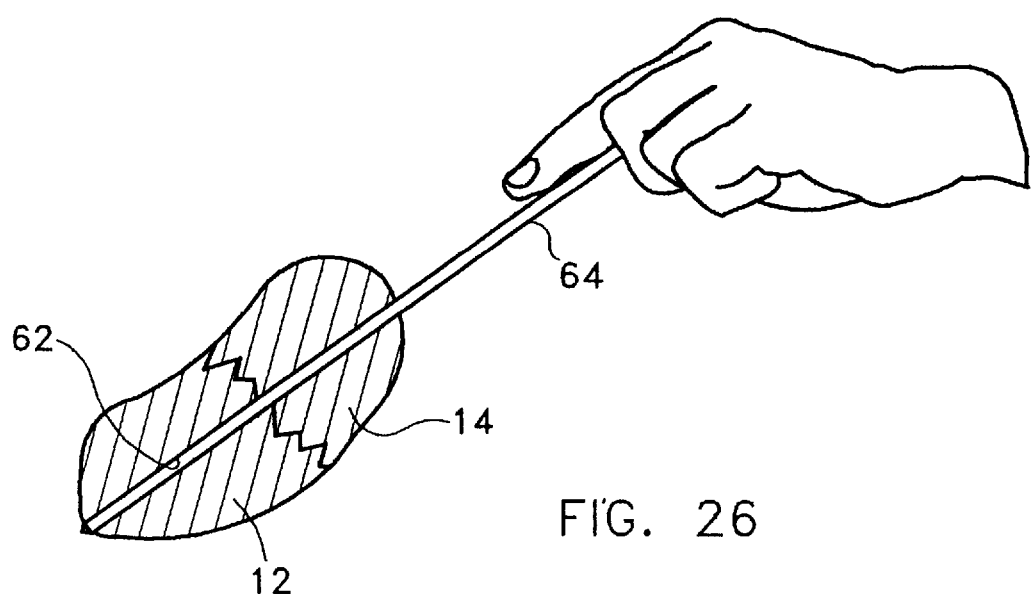
FIG. 26 is a cross section of a fractured scaphoid having a guide passing through both scaphoid fragments.

Turning to FIG. 25, the proximal and distal bone fragments 12 and 14, respectively, of scaphoid 10 are schematically shown with a fracture extending generally transverse to the longitudinal axis of the scaphoid 10. Next, and as schematically shown in FIG. 26, the bone fragments 12 and 14 are drilled to define a bore 62 extending through both fragments and a guide 64 is tightly inserted into the bore 62.

Figure 27:
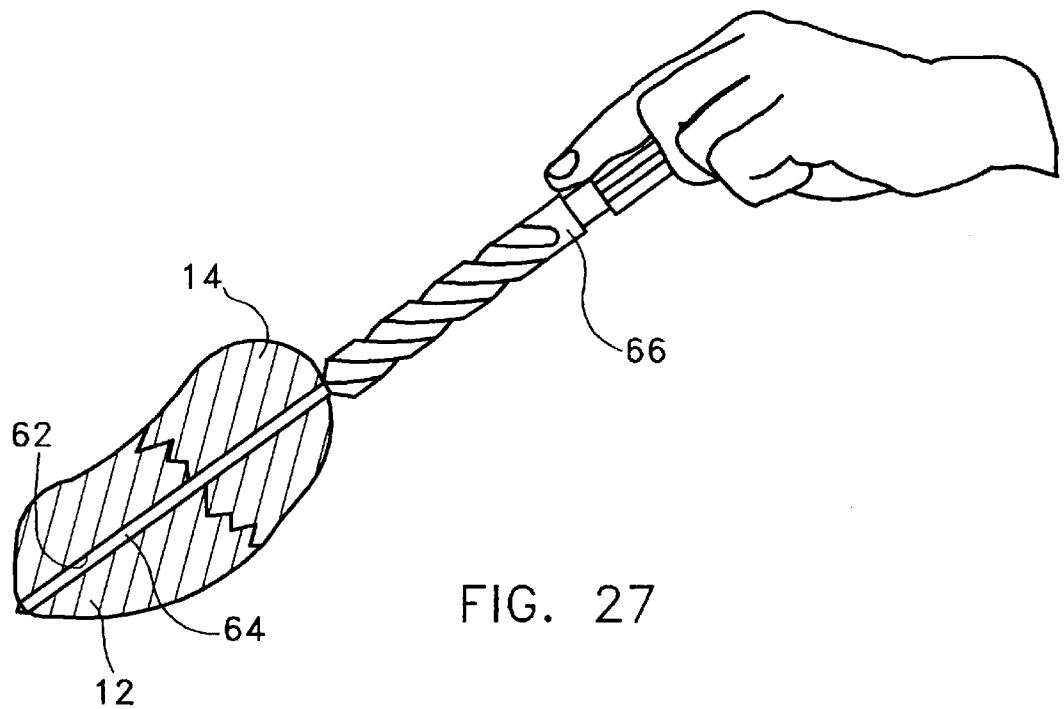
FIG. 27 is a cross section of a fractured scaphoid showing a cannulated drill arranged along and about the guide.
Figure 28:
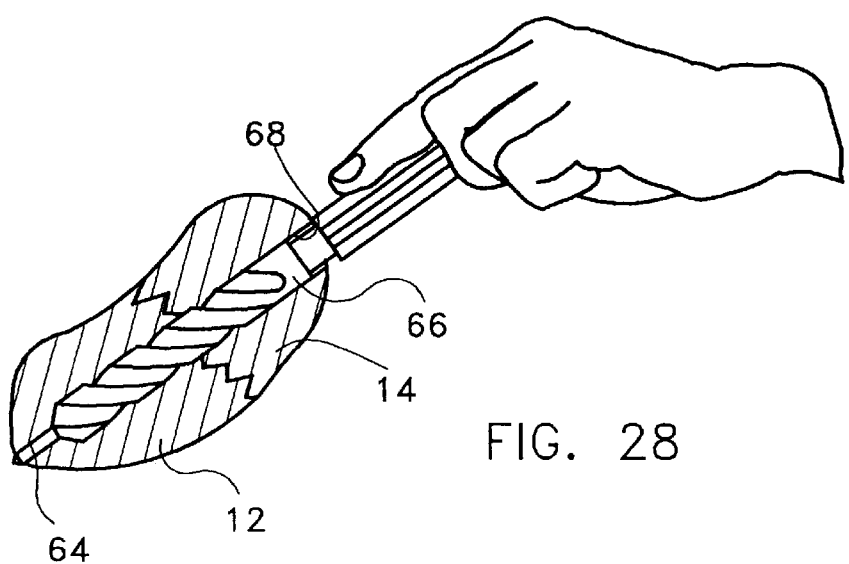
FIG. 28 is a cross section of a fractured scaphoid showing the cannulated drill passing downwardly through the fractured scaphoid bone.
Figure 29:
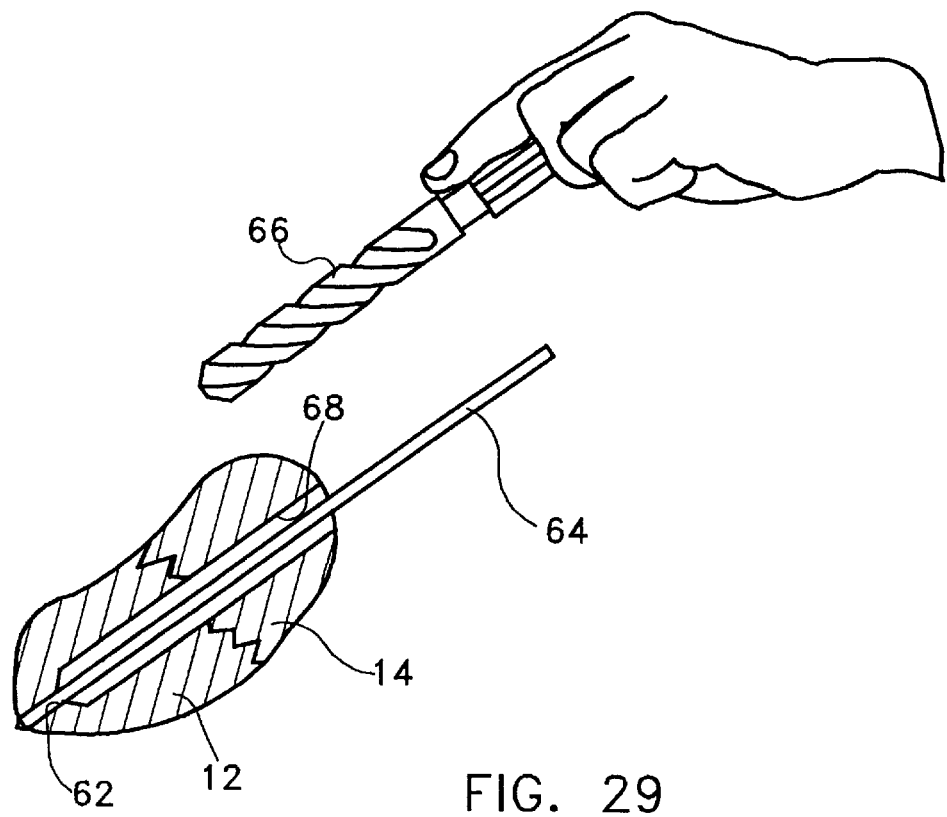
FIG. 29 is a cross section of the fractured scaphoid bone fragments after the cannulated drill is removed therefrom.

As shown in FIG. 27, a conventional cannulated drill 66 is axially fitted over and slides along the guide 64. As shown in FIG. 28, the drill 66 is operated to provide a bore 68 that passes through the bone substance of fragment 14 and for a substantial distance into the bone substance of fragment 12. Because the drill 66 moves endwise along guide 64, that portion of bore 68 defined by fragment 14 is axially aligned with that portion of bore 68 defined by fragment 12. After the bore 68 is provided, drill 66 is removed from the guide 64 as shown in FIG. 29.

Figure 30:
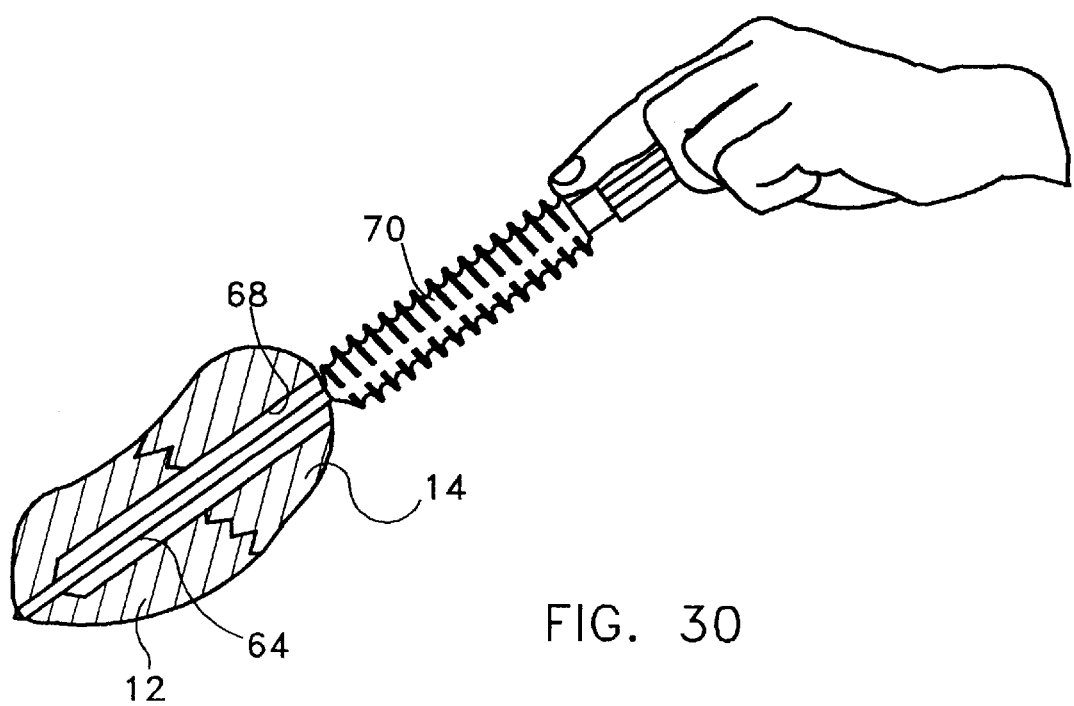
FIG. 30 is a cross section of the fractured scaphoid showing a cannulated tap arranged along and about the guide for insertion into a drilled bore formed by the cannulated drill.
Figure 31:
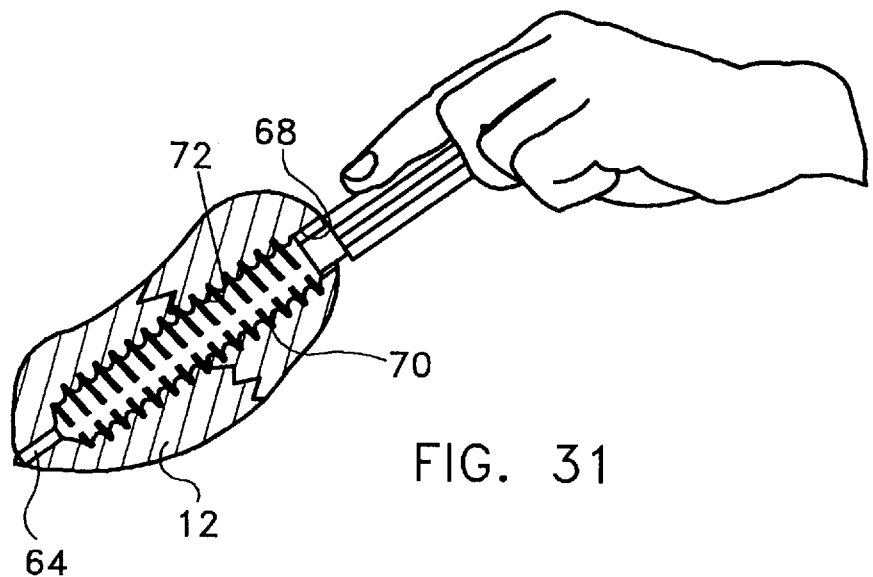
FIG. 31 is a cross section of the fractured scaphoid showing the tap fully inserted therein.
Figure 32:
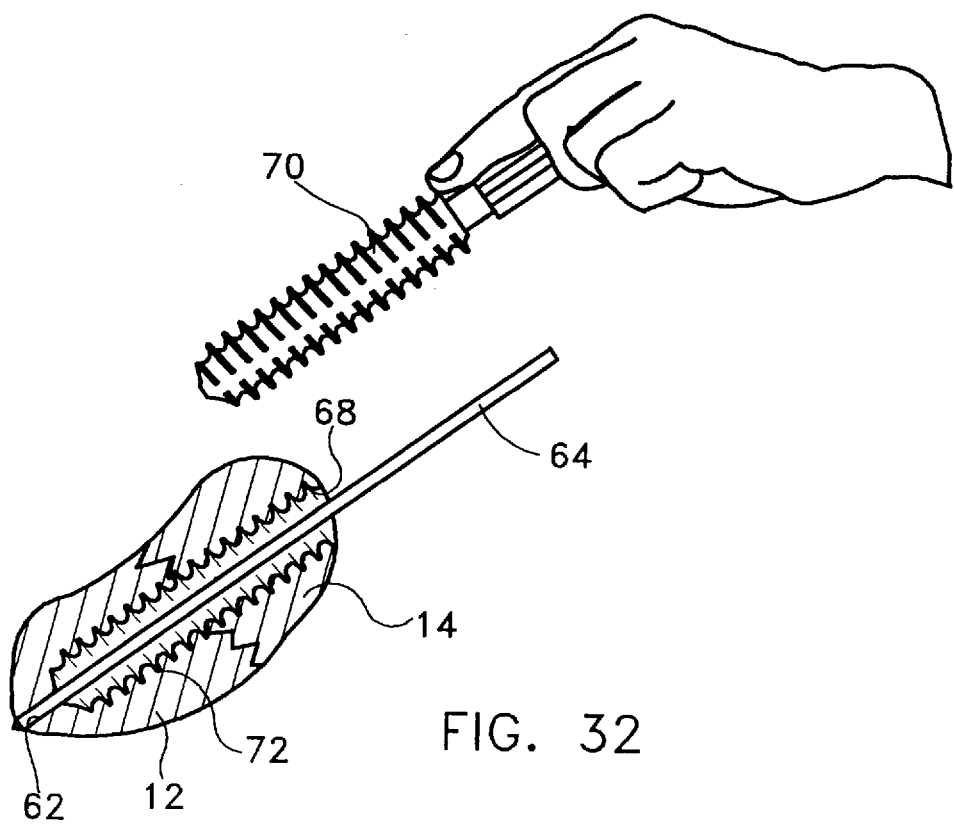
FIG. 32 is a cross section of the fractured scaphoid with the tap being removed therefrom.

Next, a conventional cannulated tap 70 is arranged along the guide 64 as shown in FIG. 30. As is typical, tap 70 is passed along the guide 64, as shown in FIG. 31, to provide internal threading 72 to the bore 68. Notably, the internal threading 72 extends through the bone substance of fragment 14 and for a substantial axial distance of bone fragment 12. Also, it is to be noted, that the internal threading 72 provided by tap 70 is of like hand and corresponds to the external threading 22 and 32 provided on fasteners 20 and 30, respectively. After the tapping operation is complete, the tap 70 is removed from the bore 68 as shown in FIG. 32.

Figure 33:
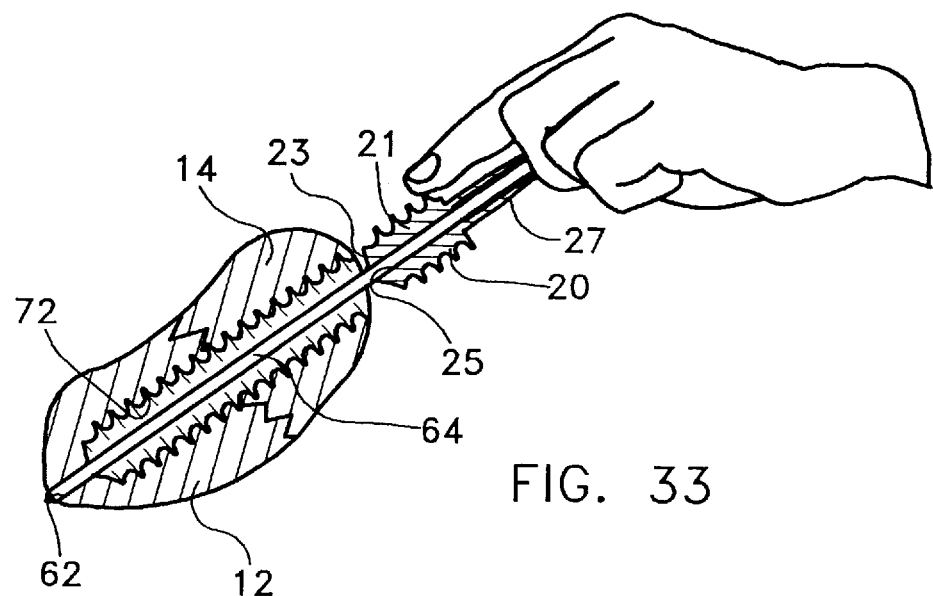
FIG. 33 is a cross section of the fractured scaphoid showing a fastener similar to that illustrated in FIGS. 9 through 11 being arranged for sliding movement over and along the guide.
Figure 34:
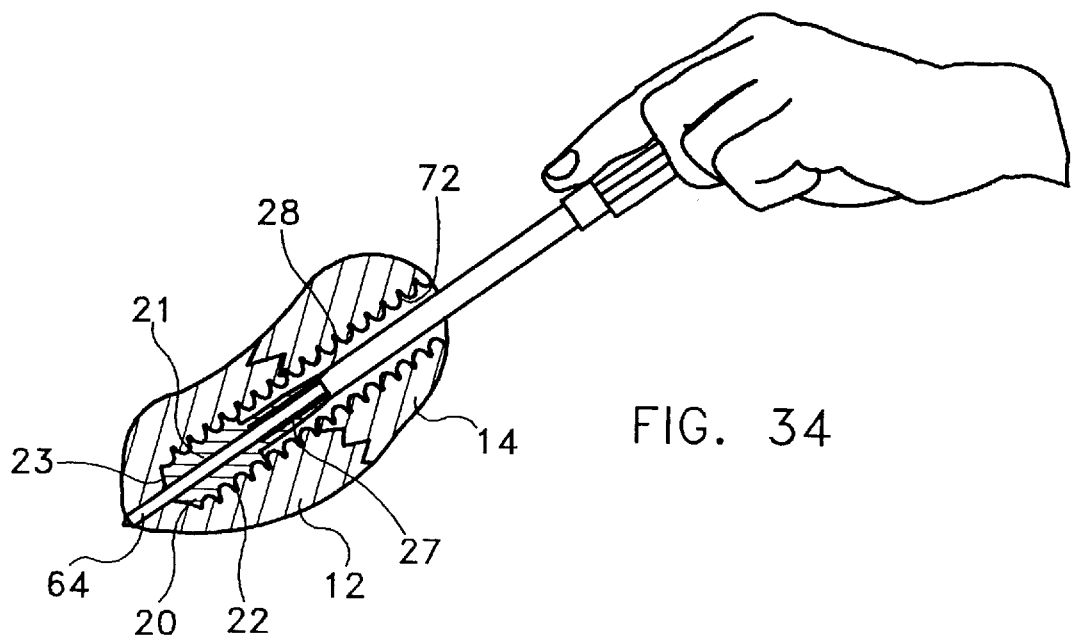
FIG. 34 is a cross section of the fractured scaphoid showing the first fastener fully inserted in one of the bone fragments and wherein the trailing end of the first fastener is rotated by a driving tool.

The first fastener 20 is next inserted into the fractured scaphoid. As shown in FIG. 33, the bore 25 in the elongated member 21 allows fastener 20 to be guided and vertically positioned proximate to the end of fragment 14. Thereafter, a suitable tool is used to engage the transverse slot 28 at the distal end of member 21. The surgeon rotates the fastener 20 with the tool whereby the external threading 22 of member 21 engages and follows the interior threading 72 in the bone fragments 12 and 14. As shown in FIG. 34, the surgeon rotates the first fastener 20 until the entire fastener 20 is thready buried within the bone substance of the first fragment 12. Then, the surgeon removes the tool used to drive the first fastener 20.

Figure 35:
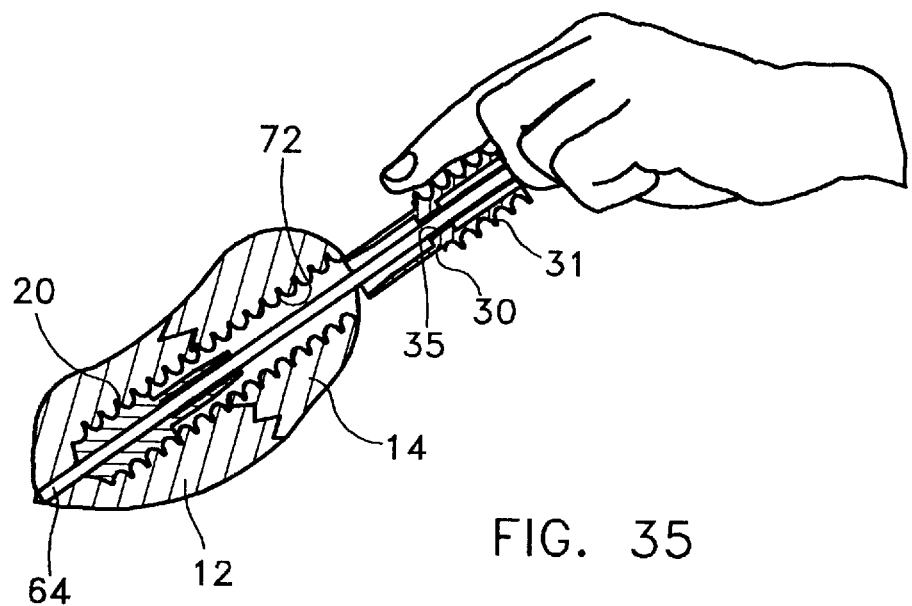
FIG. 35 is a cross section of the fractured scaphoid showing a second fastener similar to that illustrated in FIGS. 13 through 16 being arranged for guided sliding movement over and along the guide.
Figure 36:
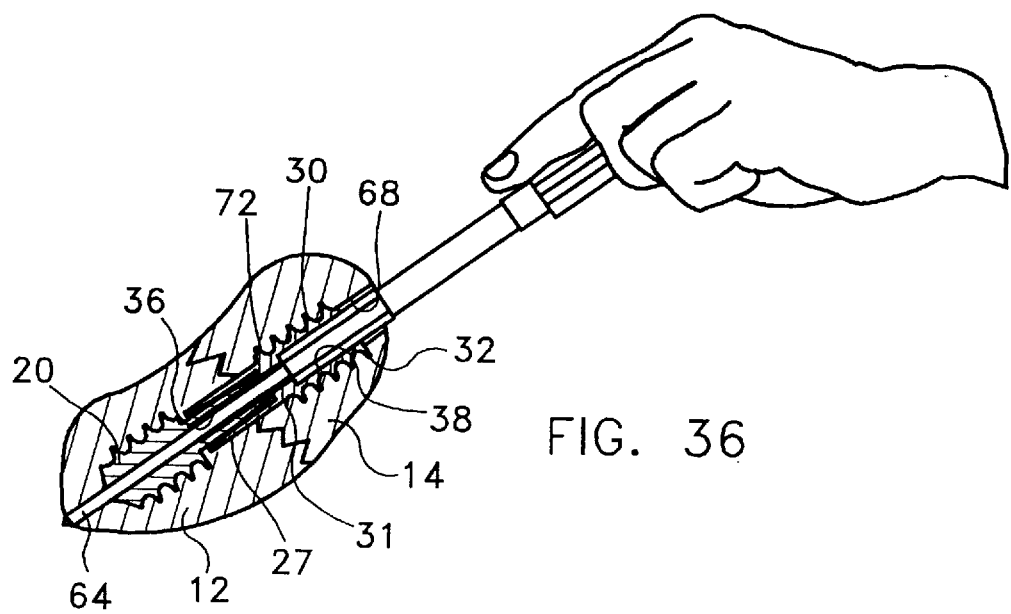
FIG. 36 is a cross section of the fractured scaphoid showing the second fastener fully inserted in the second scaphoid bone fragment and wherein the second fastener is rotated by a driving tool.
Figure 37:
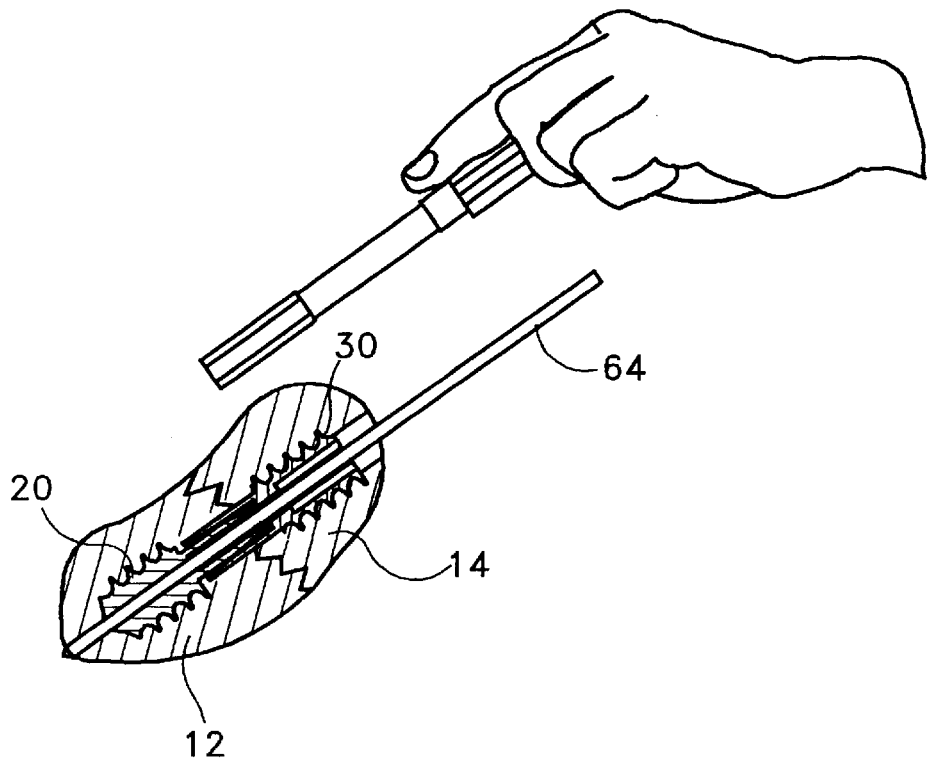
FIG. 37 is a cross sectional view similar to FIG. 36 but showing the driving tool for the second fastener being removed therefrom.

Next, the second fastener 30 is inserted into the fractured scaphoid and into operable combination with the first fastener 20. As shown in FIG. 35, the bore 35 in the elongated member 31 allows the fastener 30 to be vertically guided and positioned proximate the end of fragment 14. Thereafter, and as shown in FIG. 36, a suitable tool is inserted into the cross-sectioned counterbore 38 of fastener 30 at the distal end thereof. The surgeon rotates the fastener 30 with the tool whereby the external threading 31 engages and follows the internal threading 72 in bone fragment 14 until the entire fastener 30 is thready buried within the bore substance of the second fragment 14. Thereafter, the surgeon removes the tool used to drive the second fastener 30 as shown in FIG. 37.

Figure 38:
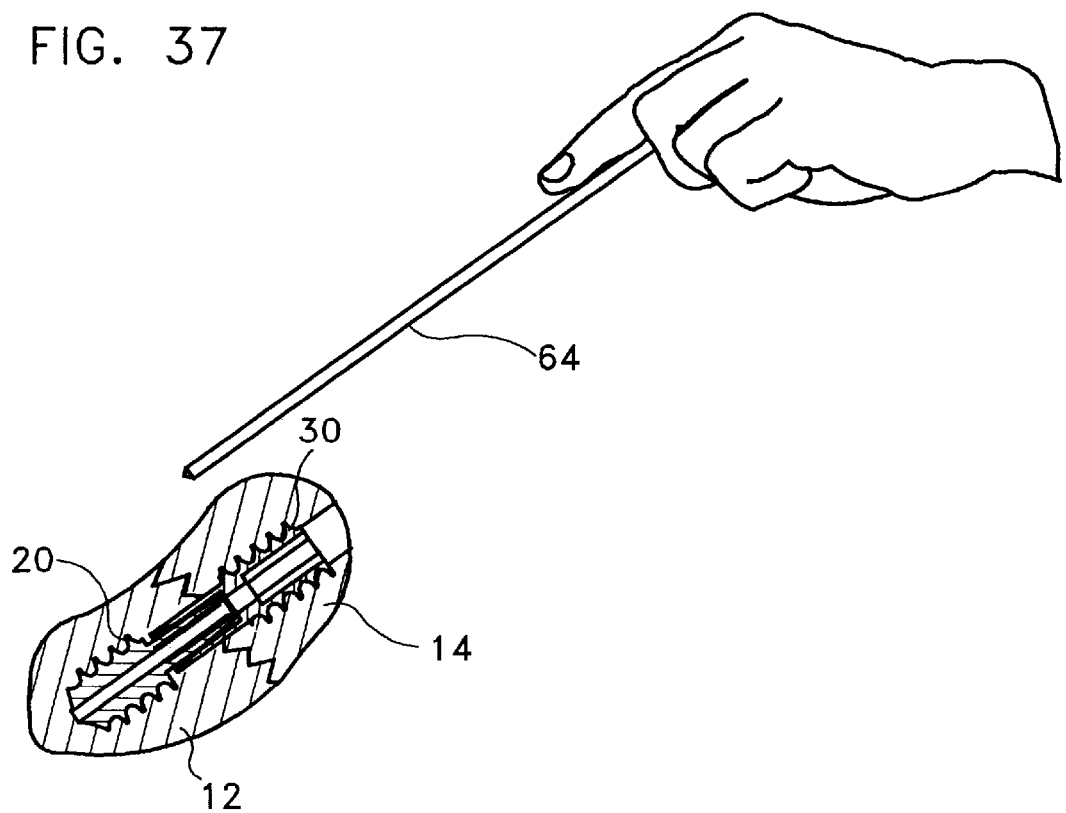
FIG. 38 is a cross section of the fractured scaphoid showing the guide removed from the scaphoid.

With the first and second fasteners 20 and 30, respectively, secured or buried in the bone fragments 12 and 14, the surgeon removes the guide 64 as shown in FIG. 38.

Figure 39:
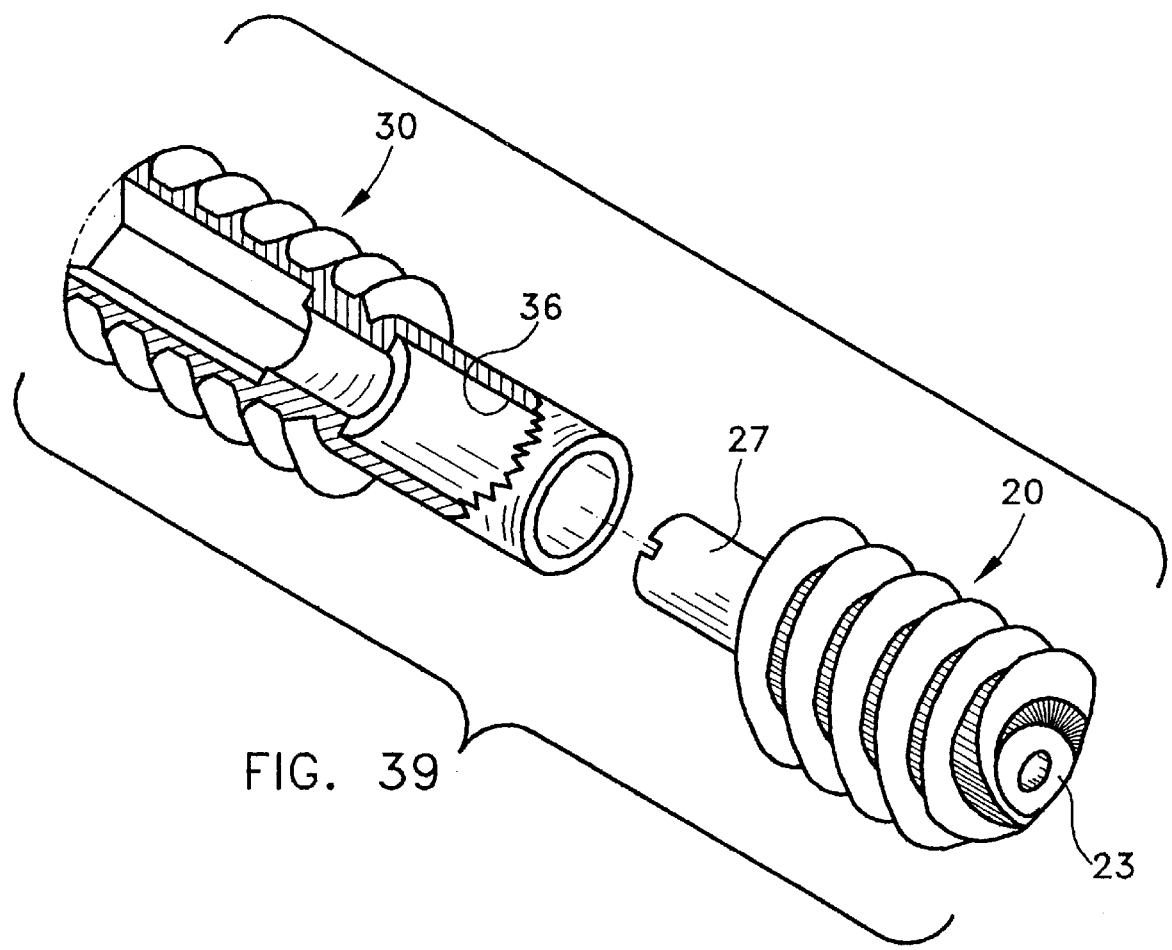
FIG. 39 is a perspective view, partly in section, showing the first and second fasteners of one embodiment of the present invention in axially spaced relation relative to each other.

FIG. 39 schematically represents the axial alignment of the first and second fasteners 20 and 30, respectively. As shown in FIGS. 33, 34 and 39, when the first fastener 20 is threadably inserted into the bone substance of the scaphoid, the pointed end 23 is arranged to initially engage the internal threading 72 in the bone substance thereby facilitating threaded engagement of the fastener 20 within the bone substance and with the reduced diameter portion 27 preferably projecting axially toward the open end of bore 68. As shown in FIG. 39, the open ended counterbore portion 36 of the second fastener 30 is then inserted first into the bore 68 in the bone fragment.

Figure 40:
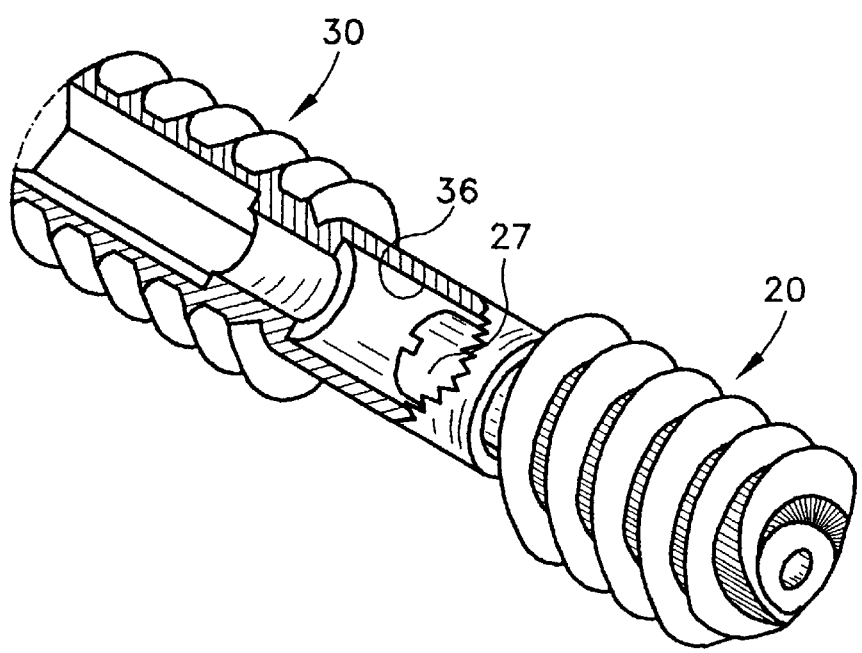
FIG. 40 is a perspective view similar to FIG. 39, and partly shown in section, showing the first and second fasteners in partially overlapping relation relative to each other.

Turning to FIGS. 36 and 40, and as mentioned above, as the second fastener 30 is threaded into the bore 68, the counterbore portion 36 of fastener 30 fits over and into operable combination with the reduced diameter portion 27 of fastener 20 to effect axial alignment of the fasteners 20 and 30 and the bone fragments 12 and 14. As will be appreciated, the axially tapering configuration on the reduced diameter portion 27 of fastener 20 cooperates with the complimentary tapered configuration at the leading end of the counterbore portion 36 to facilitate and act as a cam to effect axial alinement of the first and second fasteners 20 and 30 and the bone fragments 12 and 14 fastened thereto, respectively. Moreover, it is within the spirit and scope of the present invention that the configurations at the trailing and leading ends of the first and second fasteners 20 and 30, respectively, could be reversed without detracting or departing from the spirit and scope of the present invention.

Figure 41:
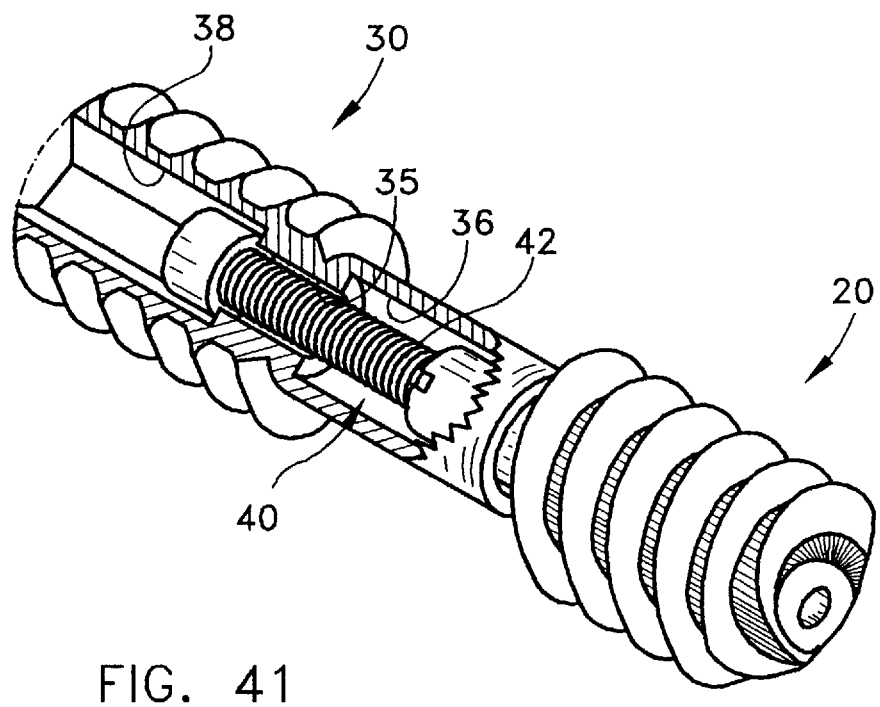
FIG. 41 is a perspective view, partly broken away, showing a connector similar to that illustrated in FIGS. 17 through 20 passing partially endwise through the second fastener and into threaded engagement with a trailing end of the first fastener.
Figure 42:
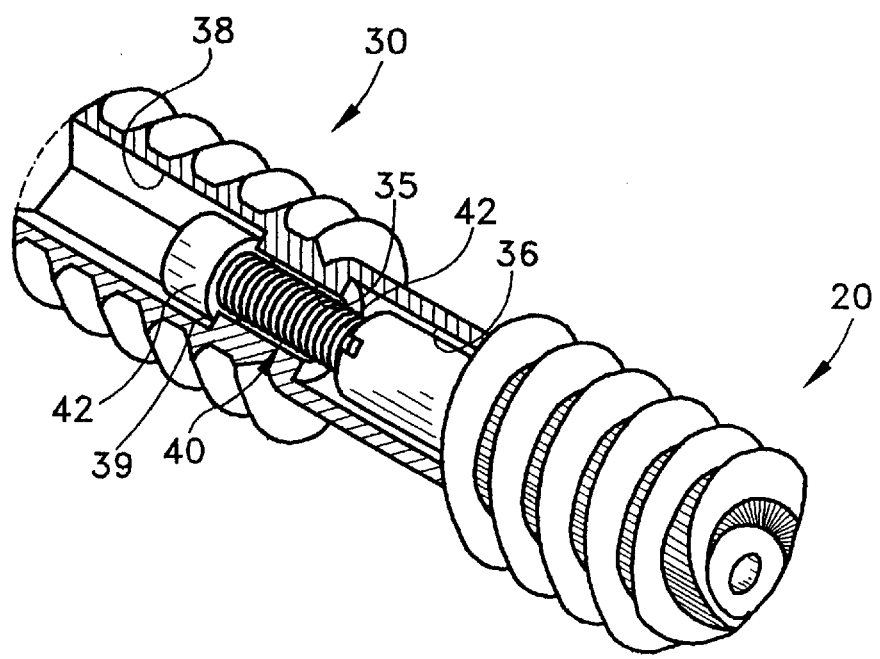
FIG. 42 is a perspective view, partly in section, showing the connector as it serves to draw the second fastener into compressed axial relationship relative to the first fastener.
Figure 43:
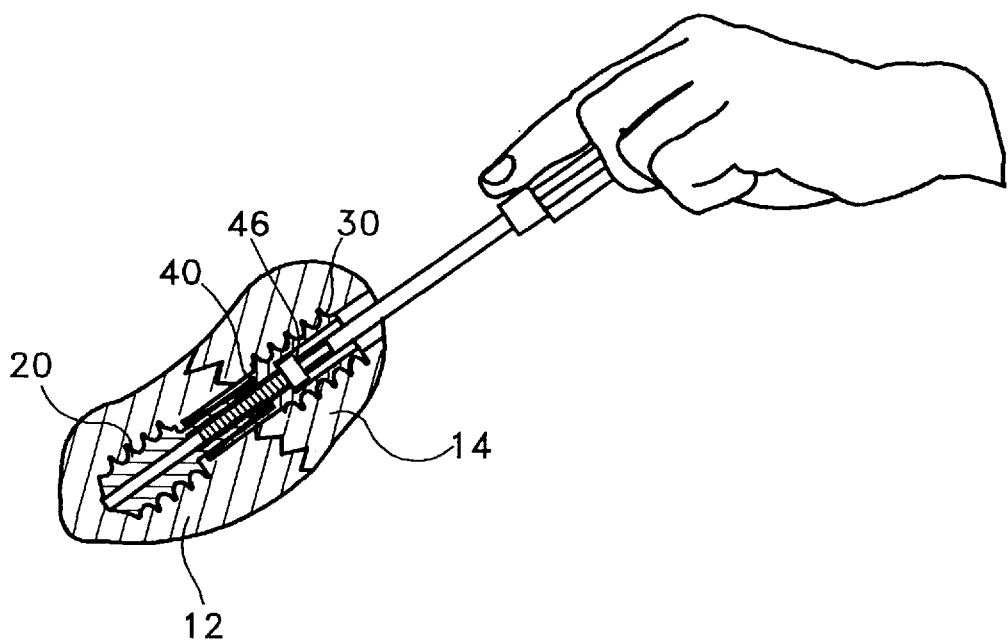
FIG. 43 is a cross section of the fractured scaphoid showing a tool for rotating the connector into threaded engagement with the first fastener.

Turning now to FIGS. 41 and 42, after the first and second fasteners 20 and 30, respectively, are threaded into the bone substance of the scaphoid, the connector 40, as shown in FIGS. 17 through 20, is inserted into combination with the fasteners 20, 30. As shown, the shank portion 42 of connector 40 endwise passes first through the counterbore portion 38, then through bore 35, and finally through the counterbore portion 36 of fastener 30 and, ultimately, into threaded engagement with the internal threading 26 axially extending along a least portion of the length of the bore 25 of fastener 20. As shown in FIG. 43, a suitable tool releasably fits into the open end of the blind socket 46 to turn the connector 40 relative to the first and second fasteners 20 and 30.

It will be appreciated at this point in the procedure some degree of gap or separation may exist between the bone fragments 12 and 14. Notably, and as schematically illustrated in FIG. 42, the head end or portion 42 of connector 40 is larger than bore 35 defined by fastener 30 thus preventing passage of the head portion 42 past the shoulder 39 defined by the second fastener 30. Any gap or separation existing between the bone fragments 12, 14 is narrowed by the surgeon rotating the connector 40. That is, with the head portion 42 of connector 40 in operable engagement with the shoulder 39 of the second fastener 30, continued rotation of the connector 40 will cause and result in the first and second fasteners 20 and 30, respectively, and the bone fragments attached to each being drawn toward each other. Ultimately, the bone fragments 12, 14 are preferably drawn into abutting relationship under a predetermined compression relative to each. Since the fasteners 20 and 30 are already fixed in the bone substance, the ability to rotate the connector 40 allows the surgeon an appropriate "feel" when the bone fragments 12, 14 are drawn into a predetermined and proper compressive relationship relative to each other.

Figure 44:
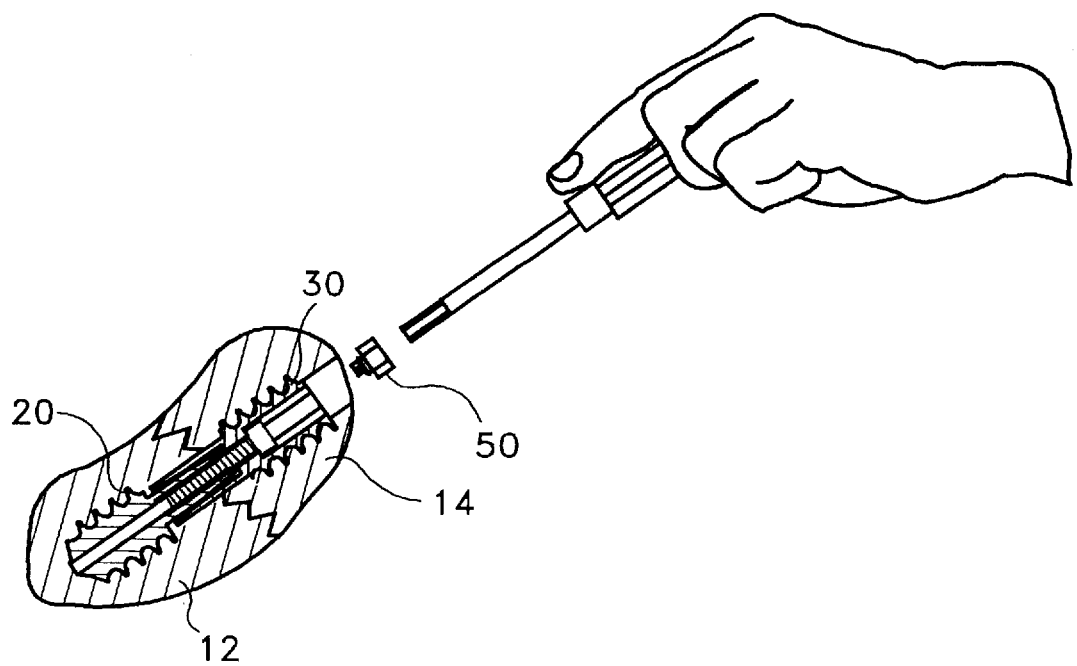
FIG. 44 is a cross section of the fractured scaphoid showing a retainer apparatus similar to that illustrated in FIGS. 21 through 24 being inserted into operable engagement with other components of the fixation assembly of the present invention.
Figure 45:
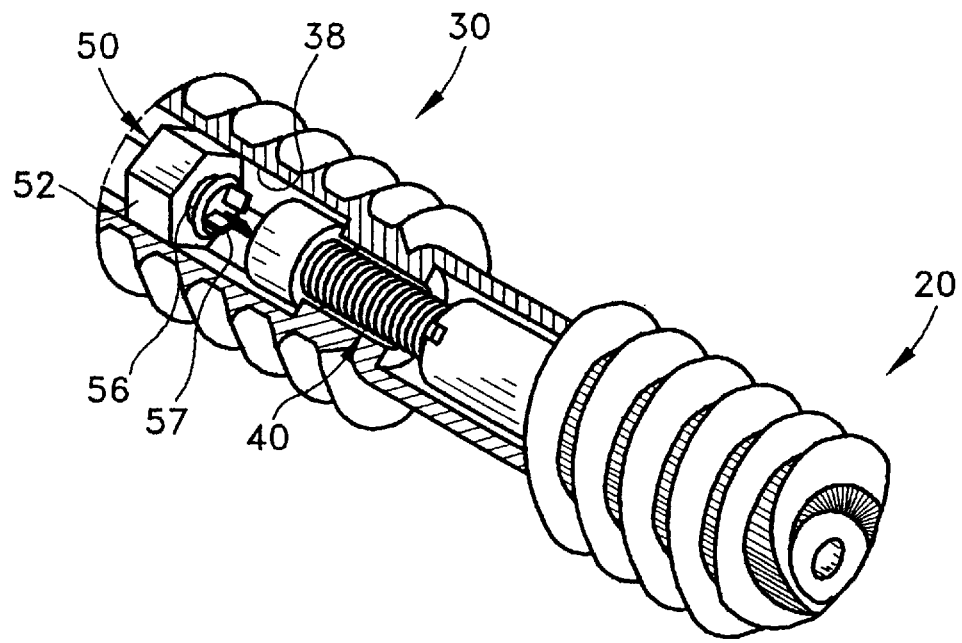
FIG. 45 is a perspective view, partly in section, and similar to FIG. 44 but enlarged to show the retainer apparatus being inserted into operable association with other components of the fixation assembly of the present invention.
Figure 47:
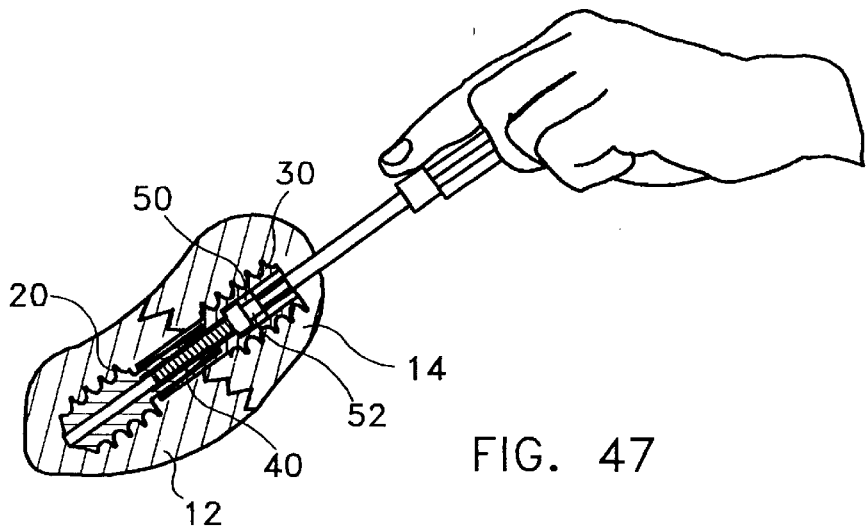
FIG. 47 is a cross section of the fractured scaphoid showing a tool for inserting the retainer apparatus into operable engagement with the other components of the fixation assembly of the present invention.
Figure 48:
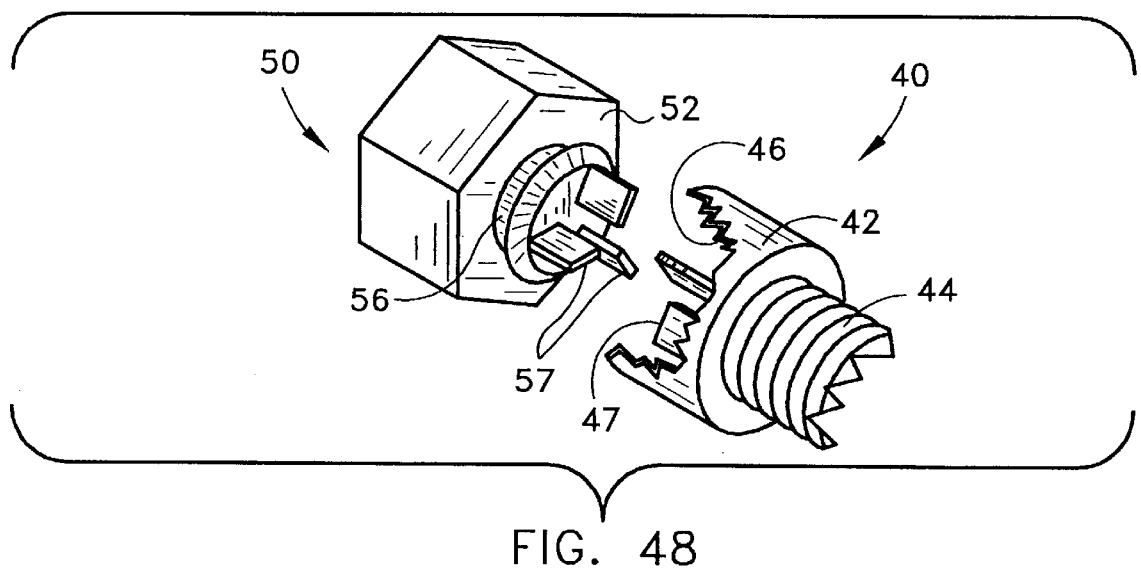
FIG. 48 is an enlarged perspective view showing the retainer apparatus and the headed end of the connector in axially spaced relation relative to each other with parts broken away to show detail.
Figure 49:
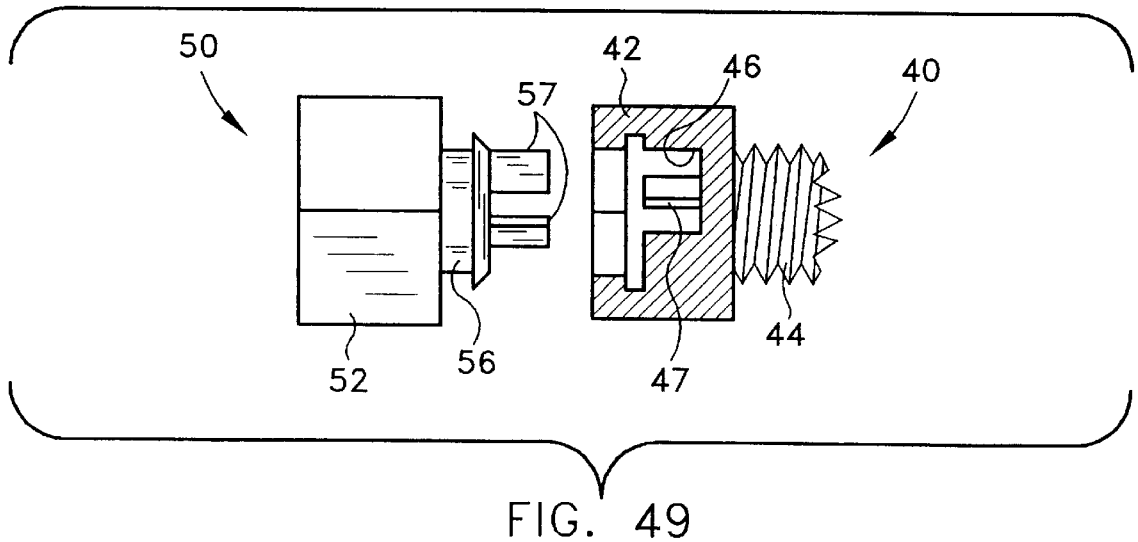
FIG. 49 is an elevational view, partially in section, of the retainer apparatus and connector shown in FIG. 48.

Next, and as shown in FIG. 44, a preferred form of retainer apparatus 50 is placed in operable combination with the fastener 30 to maintain the predetermined and proper level of compression between the fasteners 20, 30 and the bone fragments 12, 14 to promote the healing process. As shown in FIG. 45, the element 52 of the retainer apparatus 50 is initially and slidably positioned into the counterbore portion 38 of the fastener 30 with the axial extension 56 and fingers 57 directed toward the connector 40. As shown in FIG. 47, a suitable tool is releasably connected to the element 52 to facilitate axial placement of the retainer apparatus 50 into combination with the fastener 30 and connector 40. As shown in FIGS. 48 and 49, the fingers 57 of this preferred form of retainer apparatus 50 are initially spaced from the fingers 47 in the blind socket 46 defined by the head portion 42 of connector 40.

Figure 46:
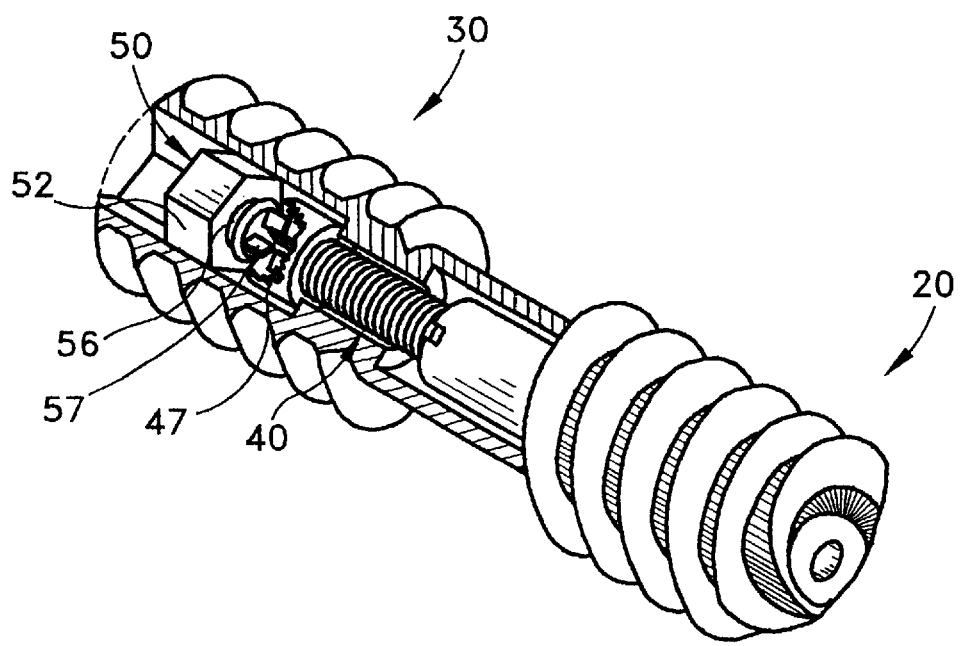
FIG. 46 is a view similar to FIG. 45, and partly in section, showing the fastener apparatus inserted further into operable engagement with components of the fastener assembly of the present invention.
Figure 50:
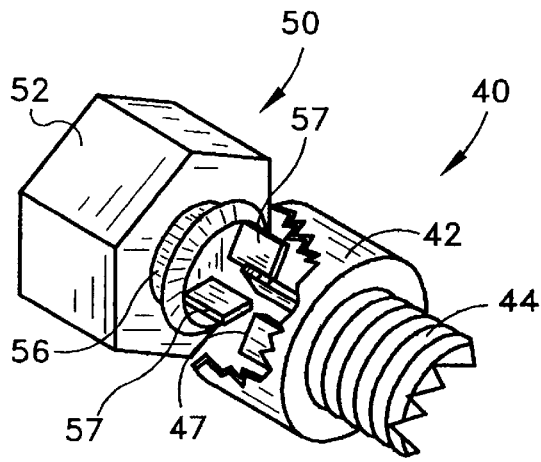
FIG. 50 is an enlarged perspective view showing the retainer apparatus and the headed end of the connector, partially in section, arranged in partial combination relative to each other.
Figure 51:
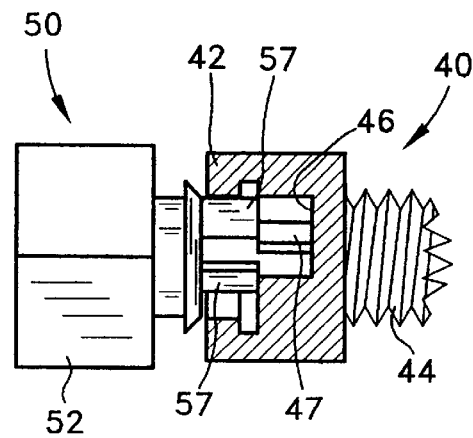
FIG. 51 is an elevational view, partly in section, showing one form of retainer apparatus and connector in partial operable combination relative to each other.

Turning now to FIG. 46, the element 52 of the retainer apparatus 50 is slidably moved toward the connector 40 such that the fingers 57 on the axial projection 56 of element 52 operably engage with the fingers 47 in the blind cavity 46 of the head portion 42 of connector 40. The relationship of the fingers 47 on the connector to the fingers 57 on the retaining apparatus is further illustrated in FIGS. 50 and 51.

Figure 52:
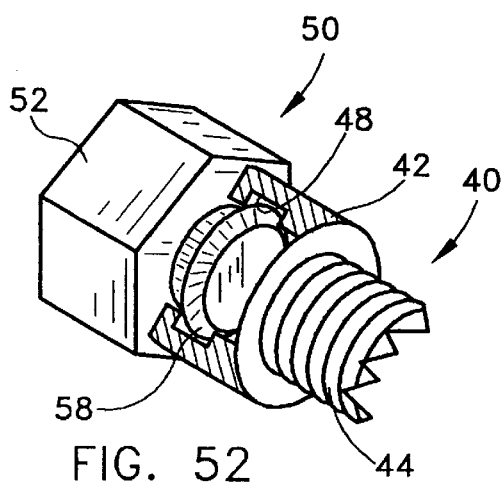
FIG. 52 is an enlarged perspective view, partly in section, showing the retainer apparatus arranged in full engagement with the headed end of the connector.
Figure 53:
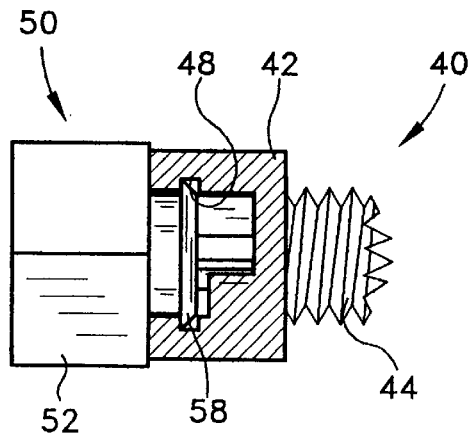
FIG. 53 is an elevational view, partly in section, showing the retainer apparatus schematically illustrated in FIG. 52 in full engagement with the headed end of the connector.

As illustrated in FIGS. 52 and 53, the element 52 of retainer apparatus 50 is further axially moved toward the connector until the annular ring 58 resiliently snaps into the channel 48 defined by the head portion 42 of the connector 40. When the retainer ring 58 snaps into the channel 48, the retainer apparatus 50 is prevented from inadvertently moving away from the connector 40 while concomitantly preventing the connector 40 from turning thereby maintaining the predetermined level of compression between the fasteners 20 and 30 and the fragments 12 and 14, respectively, carried thereby to promote the healing process.

Figure 54:
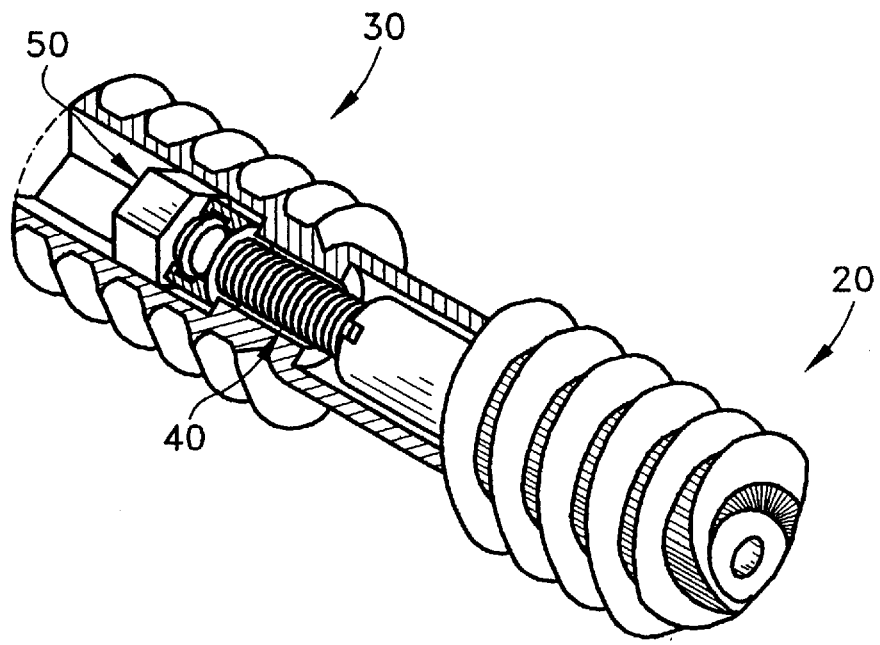
FIG. 54 is a perspective view, with parts broken away, showing one form of retainer apparatus in operable combination with the connector.
Figure 55:
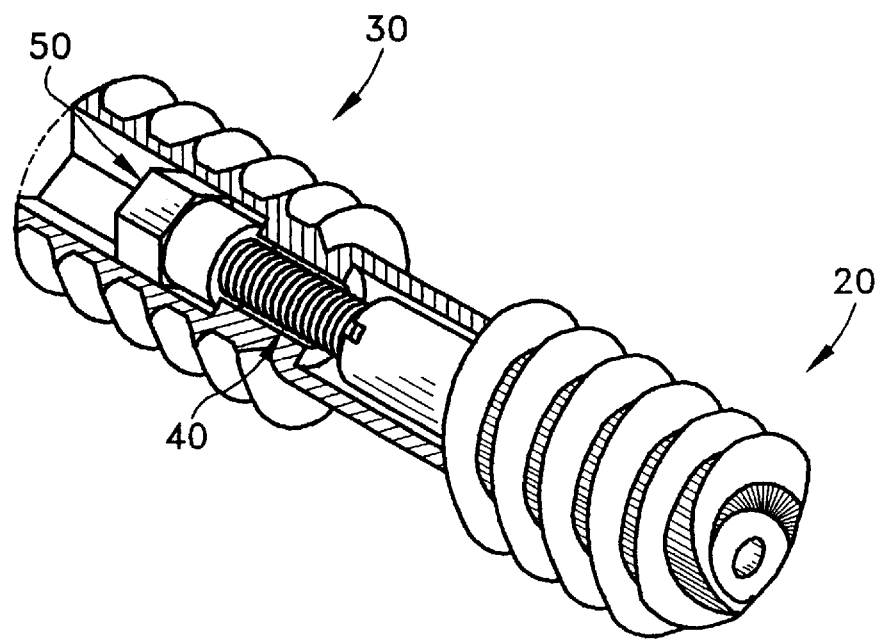
FIG. 55 is a perspective view, similar to FIG. 54, showing one form of retainer apparatus arranged in operable combination with the connector.

The retainer apparatus 50 is maintained in operable combination with the connector 40, as shown in FIGS. 54 and 55, until a suitable tool is used to purposefully remove the retainer apparatus 50. To affect removal of the retainer apparatus 50 from operable combination with the connector 40, in the illustrated form of the invention, the releasable tool used to position the retainer apparatus 50 is threadably engaged with the threaded bore 59 (FIGS. 22 and 23) defined by the element 52. Forcible retraction of the tool will likewise cause the retainer ring 58 to disengage from the channel 48 and thereby allow the retainer apparatus 50 to be removed from operable association with the connector 40.

Figure 56:
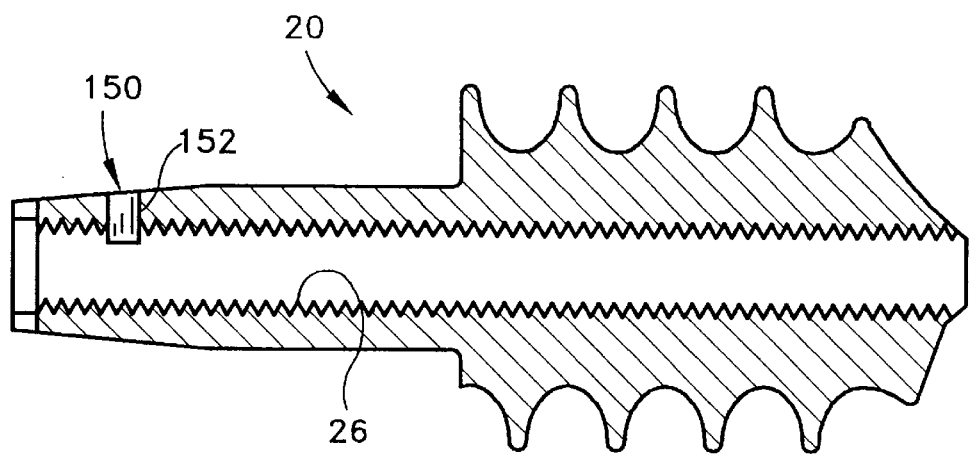
FIG. 56 is a sectional view similar to FIG. 12 but showing an alternative embodiment of retainer apparatus.

FIG. 56 schematically illustrates an alternative form of retainer apparatus 150. As shown, this alternative retainer apparatus 150 comprises an insert 152 arranged axially along and in combination with the internal threading 26 of the first fastener 20. The insert 152 is formed from a biocompatible material preferably chosen from the class consisting of: nylon, or an ultra high molecular weight polyethylene.

Figure 57:
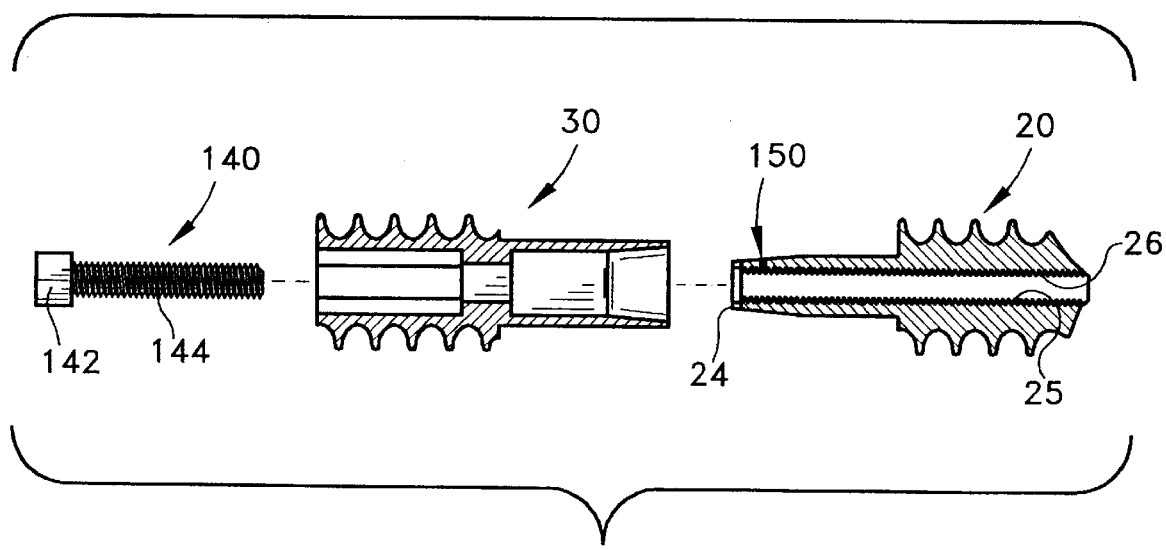
Figure 58:
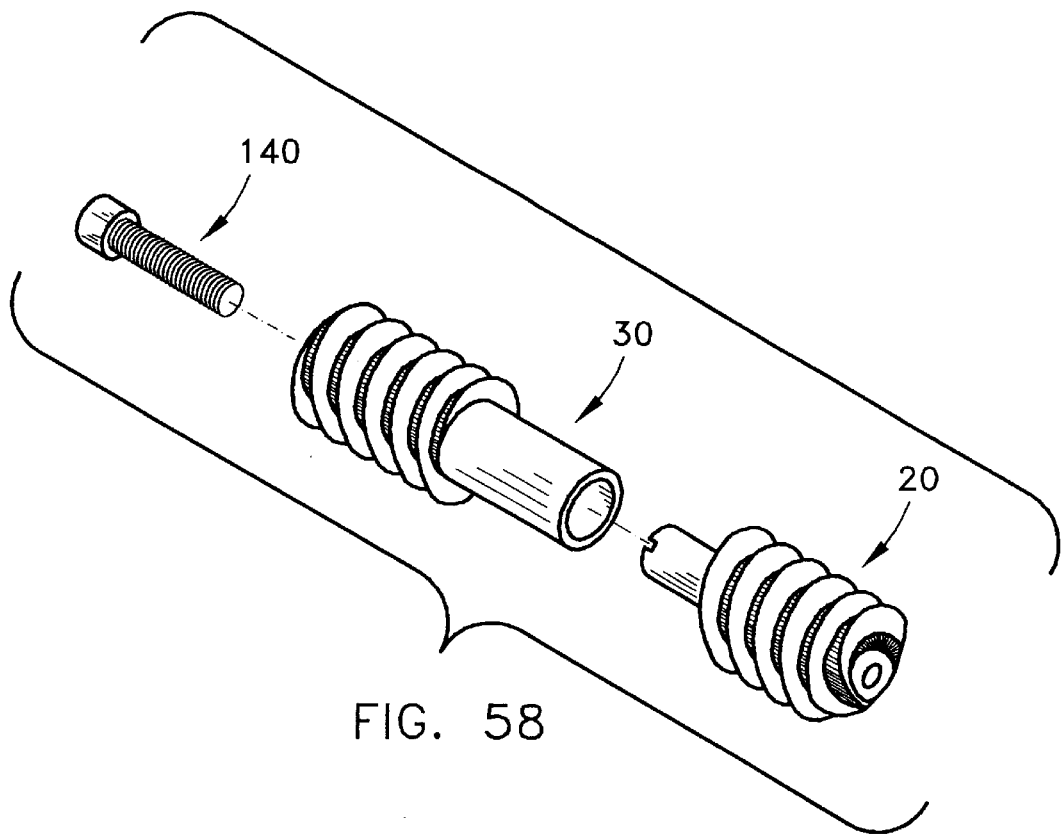
FIG. 58 is a perspective view of the fixation assembly schematically illustrated in FIG. 57.

Turning to FIG. 57, the alternative form of retainer apparatus is preferably positioned proximate to the trailing end 24 of the first fastener 20 and in combination with a trailing end of the internal threading 26. As shown in FIGS. 57 and in 58, the second fastener 30 of the multi-piece interfragmentary fixation assembly of the present invention remains substantially the same as discussed above.

Figure 59:
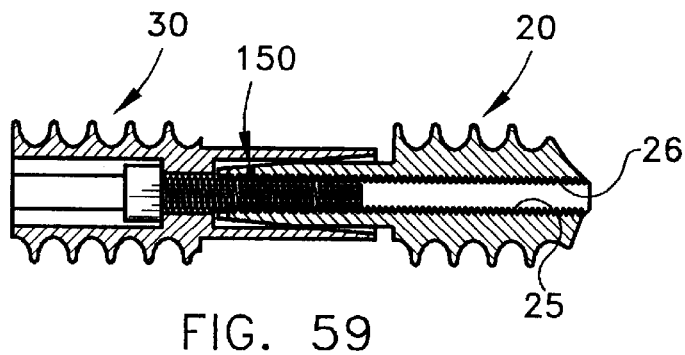
FIG. 59 is a longitudinal sectional view of the fixation assembly of the present invention with component parts, including the fastener shown in FIG. 56, illustrated in assembled relation relative to each other.

As schematically in shown in FIGS. 57 and 59, the alternative retainer apparatus 150 allows a conventional socket headed screw or connector 140 to be used in combination with the fasteners 20 and 30. That is, the connector 140 incudes an enlarged head 142 and a shank portion 144 with external conventional threading that corresponds to the internal threading 26 extending along the axial bore 25 of the first fastener 20. The connector 140 functions in an analogous manner to that described above with respect to connector 40. As the connector 140 passes inwardly along the internal threading 26 of the first fastener 20, the external threading on the shank portion 144 of fastener 140 engages with the retainer apparatus 150 in a manner preventing inadvertent turning of the connector 140 and thereby maintaining the compressive force preselected by the surgeon between the fasteners 20 and 30 to promote the healing process.

Figure 60:
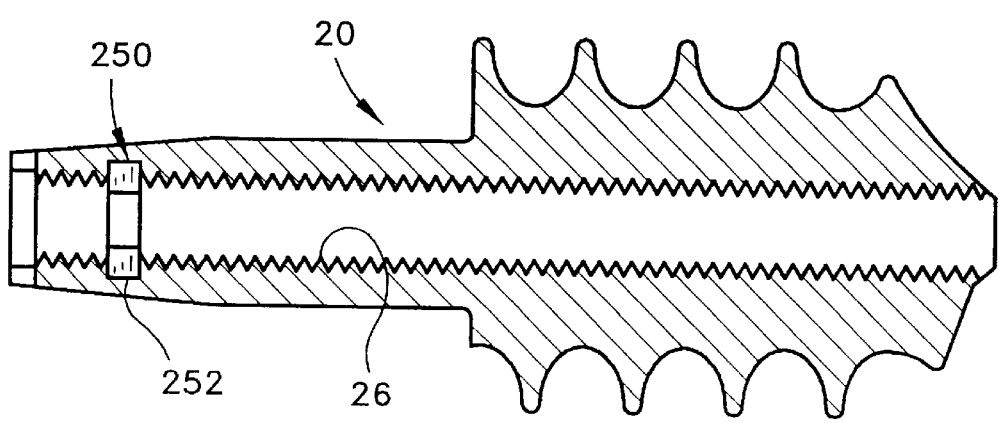
FIG. 60 is a view similar to FIGS. 12 and 56 but showing another alternative embodiment of retainer apparatus.

FIG. 60 schematically illustrates another alternative form of retainer apparatus 250. As shown, this alternative retainer apparatus 250 comprises an annular insert 252 arranged axially along and in combination with the internal threading 26 of the first fastener 20. The annular insert 252 is preferably formed from a biocompatible material preferably chosen from the class consisting of: nylon, or an ultra high molecular weight polyethylene. The retainer apparatus 250 functions in an analogous manner to that described above regarding the alternative form of retainer apparatus 150. Thus, no further detailed description need be provided therefor for a complete understanding of its function and operation.

Figure 61:
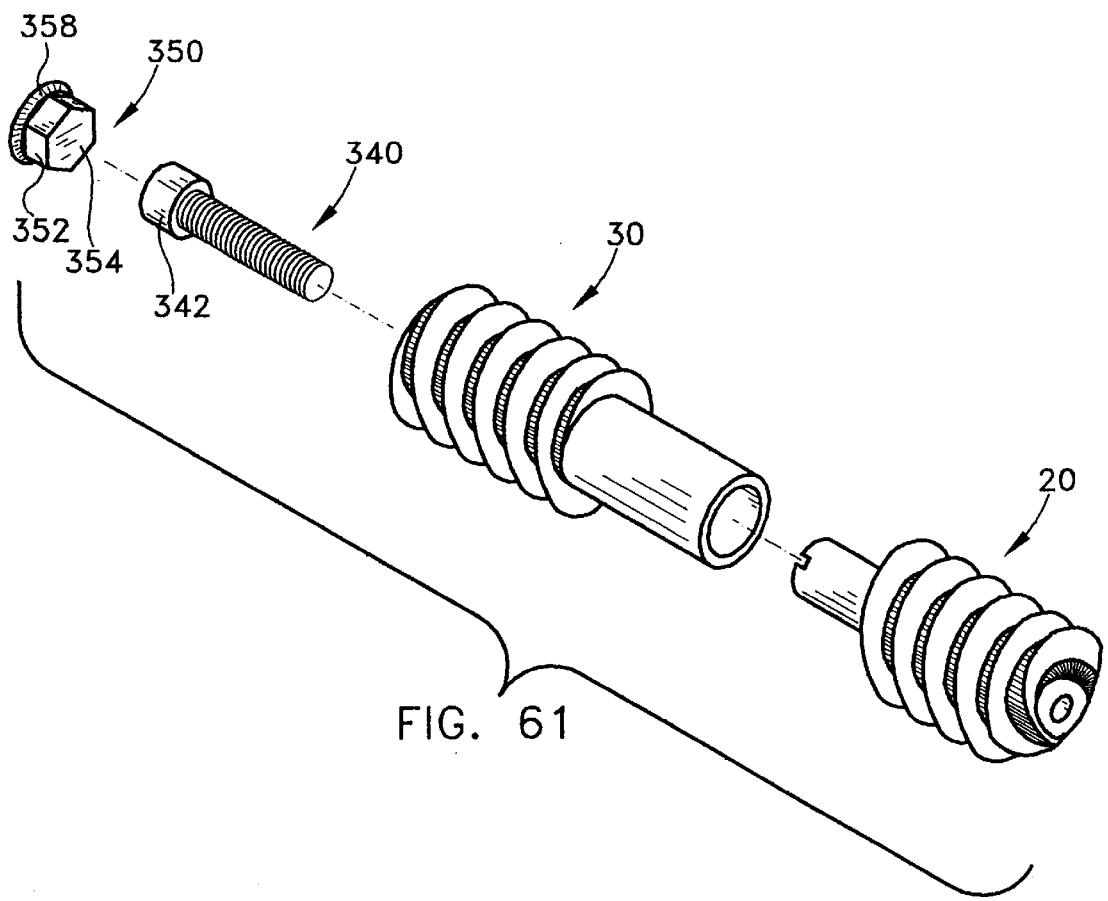
FIG. 61 is a perspective view of a fixation assembly according to the present invention having an alternative embodiment of a retainer apparatus.
Figure 62:
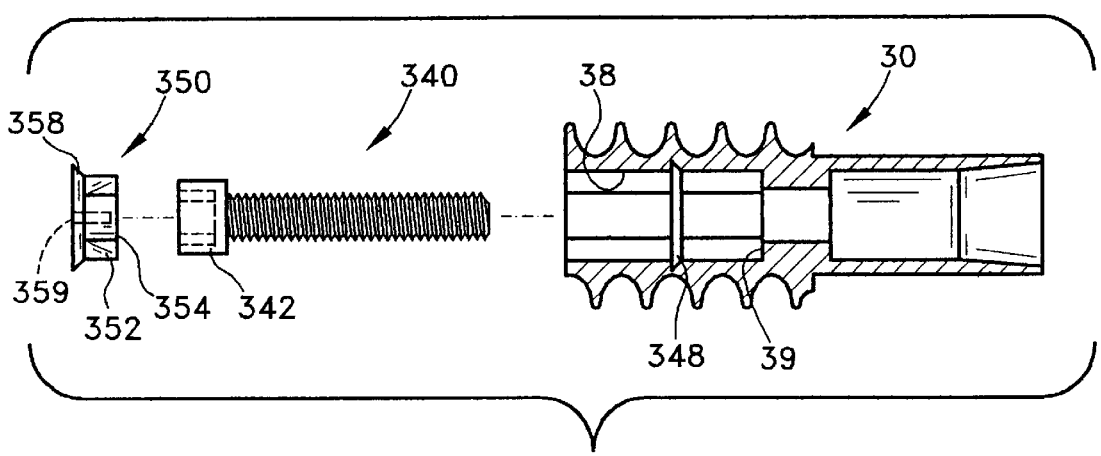
FIG. 62 is an elevational view showing a second fastener, a connector, and the alternative embodiment of a retainer apparatus as schematically illustrated in FIG. 61.
Figure 63:
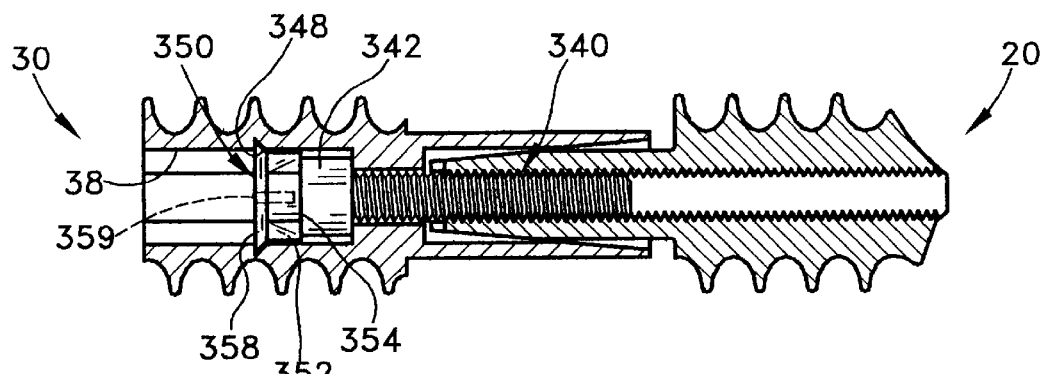
FIG. 63 is a longitudinal sectional view of the fixation assembly illustrated in FIG. 61.

Still another form of retainer apparatus 350 is schematically illustrated in FIGS. 61 through 63. In this embodiment, the retainer apparatus 350 comprises an element 352 including a body portion 354 with a cross-sectional configuration generally corresponding to the cross-sectional configuration of the counter bore 38 in the second fastener 30. Suffice it to say, the body portion 354 of element 352 has a cross-sectional configuration that operates in combination with the cross-sectional configuration of the counterbore 38 to prevent rotation of the element 352 relative to the second fastener 30. In this embodiment, element 352 of the retainer apparatus 350 includes a retaining ring 358 that is carried by the body 354 of element 352.

This alternative form of retainer apparatus 350 is adapted to operate in combination with a conventional socket headed screw or connector 340. The connector 340 functions in an analogous manner to that discussed above with respect to connector 40 except that connector 340 does not require the specifically shaped blind socket portion as does connector 40.

As schematically illustrated in FIGS. 62 and 63, the second fastener 30 defines an annular channel 348 that is spaced a predetermined distance from the shoulder 39 defined by the second fastener. The predetermined distance separating channel 348 and shoulder 39 is equal to the axial length of the headed portion 342 of connector 340 and the axial length the ring 358 is disposed from a leading edge of the body portion 354 of element 352. Preferably, the annular ring 358 on the element 352 is formed from a pliable material that is biocompatible with the bone and tissue substance wherein the fixation assembly of the present invention is adapted for use. Suffice it to say, the annular ring 358 is formed from a material that allows the ring 358 to compress and subsequently snap into and combine with the channel 348 in a manner preventing inadvertent axial displacement of the element 352 toward the trailing end of the fastener 30. Accordingly, once the surgeon selects the predetermined level of compression between the fasteners, the retainer apparatus 350 is inserted until the annular ring 358 snaps into the annular channel 348 thereby preventing the fastener 30 from turning with the second fastener 30 and thereby maintaining the predetermined level of compression between the fasteners 20 and 30.

As shown in FIGS. 62 and 63, element 352 of retainer apparatus 350 further defines a threaded bore 359. As will be appreciated, the retainer apparatus 350 is maintained in operable combination with the second fastener 30 and prevents inadvertent rotation of the fastener 340 until a suitable tool removes the retainer apparatus 350 from association with the connector 340. To effect the removal of retainer apparatus 350, in this illustrated form of the invention, a releasable tool is threadably engaged with the threaded bore 359 defined by the element 352. Forcible retraction of the tool will likewise cause the retainer ring 358 to disengage from the channel 348 and thereby allow the retainer apparatus 352 to be removed from the interfragmentary fixation assembly 10.

Figure 63A:
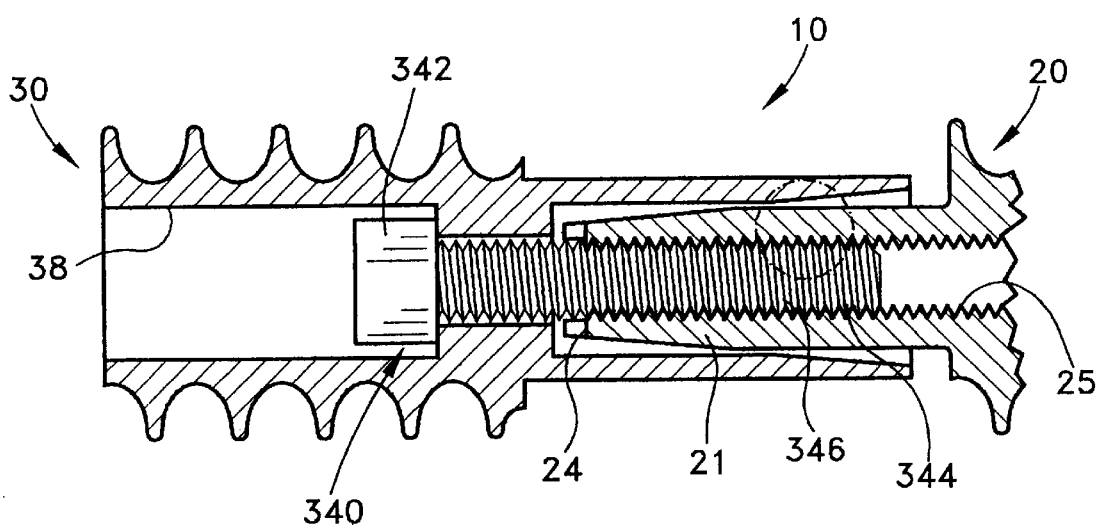
FIG. 63A is a fragmentary and enlarged longitudinal sectional view of an alternative form of fixation assembly according to the present invention.

FIG. 63A illustrates still another alternative configuration for retaining the fasteners 20 and 30 of the fixation assembly 10 in a preset or predetermined compressive relationship relative to each other. This alternative configuration includes the conventional socket headed screw or connector 340 mentioned above. As mentioned above regarding connector 140, the connector 340 includes an enlarged head portion 342 and a shank portion 344 with conventional external threading 346 extending axially therealong. The connector 340 functions in an analogous manner to that described above with respect to connectors 40 and 140.

In this embodiment of the invention, an internal locking thread form 326 (FIG. 63B) is defined along at least a portion of the axial length of the bore 25 defined by the first fastener 20. In a preferred form of the invention, the internal locking thread form 326 extends an axial lengthwise distance from the trailing end 24 of member 21 and along the bore 25 of fastener 20. It should be appreciated, the internal locking thread form 326 can extend the entire or a distance somewhat less than the entire length of bore 25. In a most preferred form of the invention, the internal locking device 326 is sold under the trademark SPIRALOCK by Detroit Tool Industries and offers preload locking between the connector and threadably interconnected fastener through a unique internal thread configuration.

Figure 63B:
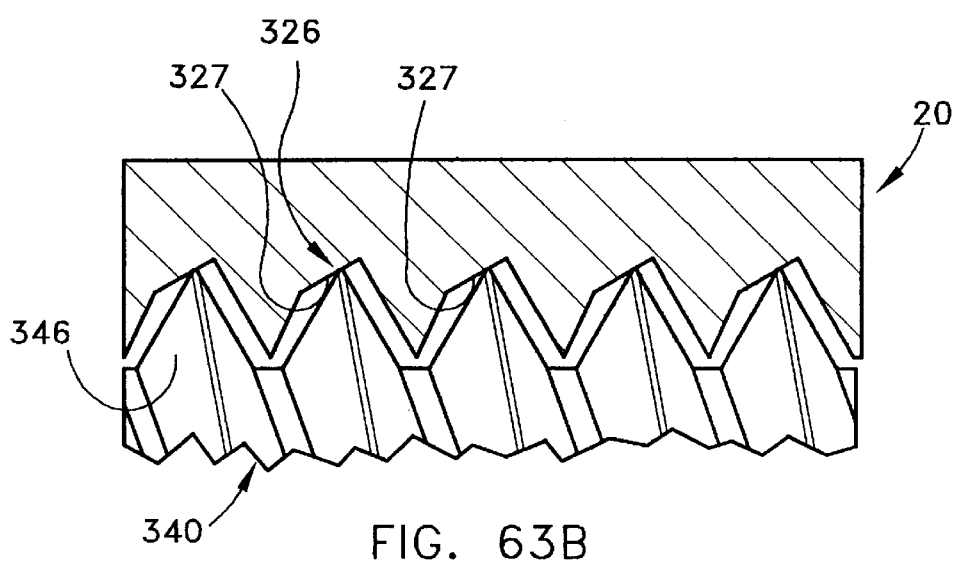
FIG. 63B is an enlarged sectional view of the area encircled in FIG. 63A.

As shown in FIG. 63B, and in the illustrated form of the invention, the unidirectional internal thread form 326 has an added 30° wedge ramp 327 at the root of each internal thread defined by fastener 20. The internal thread from 326 still mates with the standard or conventional 60° threading on the external threading 346 of the shank portion 344 of connector 340.

When a clamp load is applied to the connector 340 thereby drawing the fasteners 20 and 30 into predetermined compressive relationship relative to each other, the internal thread form or configuration 326 defined by fastener 20 locks the standard or conventional male threading 346 extending along the length of shank 344 of fastener 340 tightly against the wedge ramp 327 thereby preventing movement of the connector 340 relative to fastener 20 and thereby maintaining the predetermined compressive relationship between the fasteners 20, 30. At this point, the crests of the conventional external threading 346 are drawn tightly against the ramp surfaces 327 of the thread form 326 thus eliminating radial clearances and creating a continuous spiral, line contact along the entire length of thread engagement. This continuous line contact spreads the clamp force more evenly over all the engaged threads thus reducing fatigue failure and increasing the integrity of the threaded connection between connector 340 and fastener 20. Moreover, the internal thread form 326 for preventing the connector 340 from rotating following establishment of the predetermined compressive relationship between fastener 20, 30 furthermore yields the surgeon with the ability to "feel" the proper relationship n the identical fashion the surgeon is accustomed to working with using other arrangements. As will be appreciated, other internal thread forms could likewise be used along the length of axial bore 25 and the external threading 346 of connector 340 without detracting or departing from the spirit and scope of the present invention.

The use of an internal thread form or configuration 326 for preventing inadvertent rotation of the connector used to join the fasteners of the present invention offers several benefits. First, the internal thread form 326 is a tested and proven technique which works well under severe conditions. Second, the internal thread form 326 simplifies the fixation assembly design. Notably, when the internal thread form 326 is utilized, a conventional connector 340 is used to draw the fasteners 20, 30 into a predetermined compressive relationship relative to each other. Moreover, when a thread form 326 is used in connection with the present invention, the design of fastener 30 is simplified. That is, the counterbore 38 defined by fastener 30 is a simplified counterbore having no specific cross-sectional configuration thereto. For these and other reasons, an internal thread form is preferably used to inhibit rotation of the connector 340 relative to the fasteners thereby maintaining the preselected compressive force between the fasteners 20, 30 and, thus, the bone fragments secured to each fastener.

Not all types of bone fractures will necessarily lend themselves to the embodiment of the invention schematically illustrated in FIGS. 3 through 8 wherein two axially elongated fasteners are maintained in a compressive and end-to-end relationship relative to each other. Accordingly, the present invention contemplates alternative forms of the multipiece interfragmentary fixation assembly.

An alternative form of the multipiece interfragmentary fixation assembly is illustrated in FIGS. 64 through 68 and is generally designated by reference numeral 400. As with the first embodiment of the invention, the multipiece interfragmentary fixation assembly 400 functions to maintain bone fragments 412 and 414 in compressive relationship relative to each other. The elements of this alternative embodiment of the fixation assembly 400 that are identical or functionally analogous to those in earlier embodiments discussed above are designated by reference numerals identical to those used above with the exception that this alternative embodiment reference numerals are in the 400 series.

Figure 68:
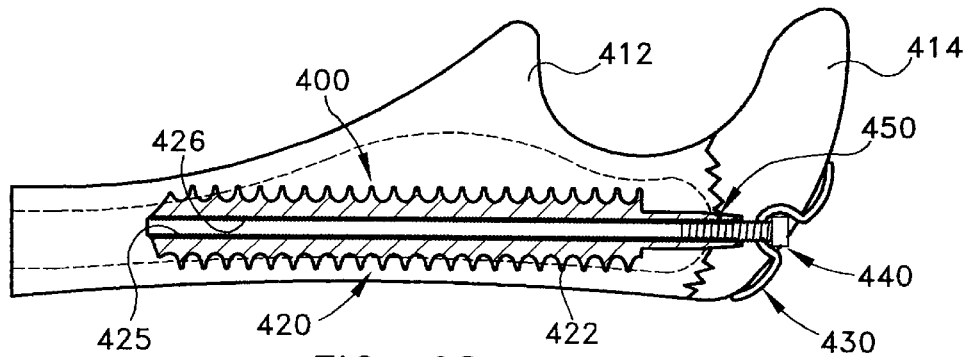
FIG. 68 is a cross sectional view of a fractured bone showing the alternative embodiment of the interfragmentary fixation assembly illustrated in FIGS. 65 through 67 arranged in operable combination therewith.

As shown in FIG. 68, this alternative embodiment of the fixation assembly 400 includes a first axially elongated fastener 420 secured to bone fragment 412, a second fastener 430 that is secured to bone fragment 414, a connector 440 that serves to maintain the first and second fasteners 420 and 430 and the bone fragments 412 and 414 attached to each, respectively, in compressive relationship relative to each other, and an apparatus 450 for maintaining the compressive relationship between the first and second fasteners 420 and 430, respectively, and the bone fragments attached to each. Suffice it to say, the first fastener 420 and the connector 440 are substantially similar to that embodiment of the invention illustrated in FIGS. 56 through 59. Moreover, this alternative embodiment of the fixation assembly further includes a retainer apparatus similar to that illustrated in FIGS. 56 or 60. It should be appreciated, however, the apparatus 450 for holding the connector 440 against rotation could involve an internal thread form similar to that disclosed in FIGS. 63A and 63B and discussed above in detail. Accordingly, no further detailed description need be provided therefor for a complete understanding of those features of the invention.

Figure 65:
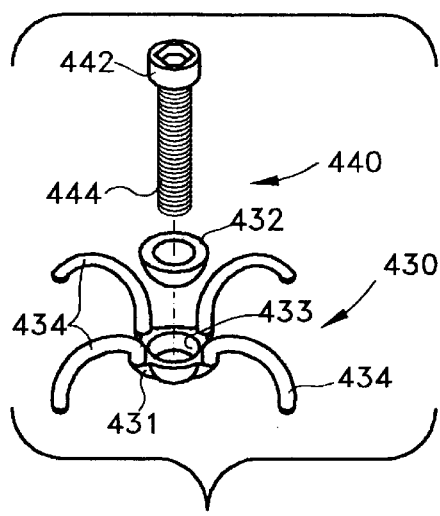
FIG. 65 is a perspective view of an alternative embodiment of a second fastener and connector for the fixation assembly of the present invention.
Figure 66:
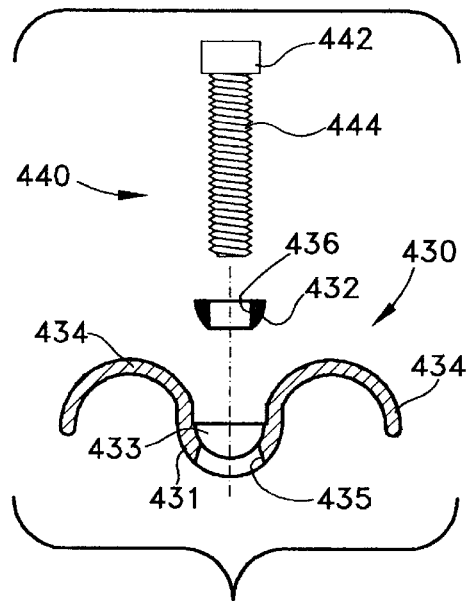
FIG. 66 is a partial sectional view of the alternative embodiment of the second fastener illustrated in FIG. 65, with components of the second fastener being shown in spaced relation relative to each other and showing the connector adapted to pass endwise therethrough.
Figure 67:
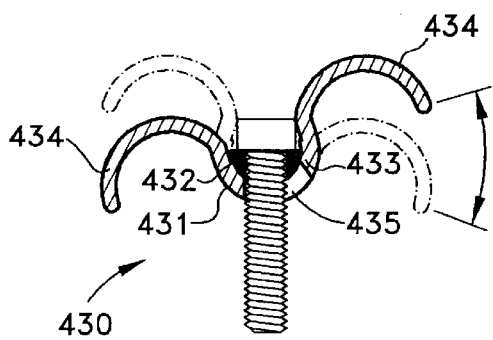
FIG. 67 is a view similar to FIG. 66 showing the component parts of the second fastener arranged in operable combination with each other and with the connector passing therethrough; with the phantom lines showing the range of motion of the second fastener.

The alternative embodiment of the second fastener 430 is best illustrated in FIGS. 65 through 67. The second fastener 430 comprises a member 431 and element 432 arranged in operable combination relative to each other. Member 431 of a fastener 430 is configured with a generally concave shaped and apertured section 433 that is generally centralized between a plurality of prongs 434 that project radially outward and away from the central section 433. Although the second fastener 430 is illustrated as having four prongs 434 extending therefrom, it will be readily appreciated by those skilled in the art that less than four prongs could radially extend away from the central section 433 of the fastener without departing or detracting from the spirit and scope of the present invention. As shown, the central section 433 defines a hemi-spherical shaped recess with an aperture 435 opening thereto. Element 432 likewise has a hemi-spherical shape that complements the concave shaped section 433. Moreover, element 432 defines an aperture 436 and element 432 is sized to permit the externally threaded shank portion 444 of fastener 440 to pass endwise therethrough while preventing the enlarged headed portion 442 of fastener 440 to pass endwise therethrough.

In an assembled relationship as shown in FIGS. 67, element 432 sits within the apertured central section 433 of member 431 and is permitted to rockingly move within the socket defined by element 431. Returning now to FIG. 68, the first fastener 420 is initially threaded into the bone substance of bone fragment 412 and the external threading 422 fixedly maintains the fastener 420 in place. The connector 440 is then passed endwise through the element 432 and member 431 of the second fastener and into threaded engagement with the internal threading 426 axially extending along at least a portion of the length of the bore 425 of fastener 420.

At this point in the procedure, some degree of gap or separation may exist between the bone fragments 412 and 414. Notably, and as illustrated in FIGS. 66 and 67, the head end 442 of connector 440 is larger than the bore 436 defined in element 432 of fastener 430. Any gap or separation existing between the bone fragments 412 and 414 is narrowed by the surgeon rotating the connector 440. That is, with the head portion 442 of connector 440 in operable engagement with the element 432 of the second fastener 430, continued rotation of the connector 440 will cause and result in the first and second fasteners 420 and 430, respectively, and the bone fragments attached to each being drawn toward each other. Ultimately, the bone fragments 412 and 414 are preferably drawn into abutting relationship under predetermined compression relative to each other. The ability to rotate the connector 440 allows the surgeon an appropriate "feel" when the bone fragments 412, 414 are drawn into a predetermined proper compressive relationship relative to each other. The predetermined and proper compressive relationship between the fasteners 420 and 430 and, thereby, the fragments 412 and 414 relative to each other is maintained by preventing the connector 440 from inadvertently turning as through a retainer apparatus similar to that described in detail above.

Figure 64:
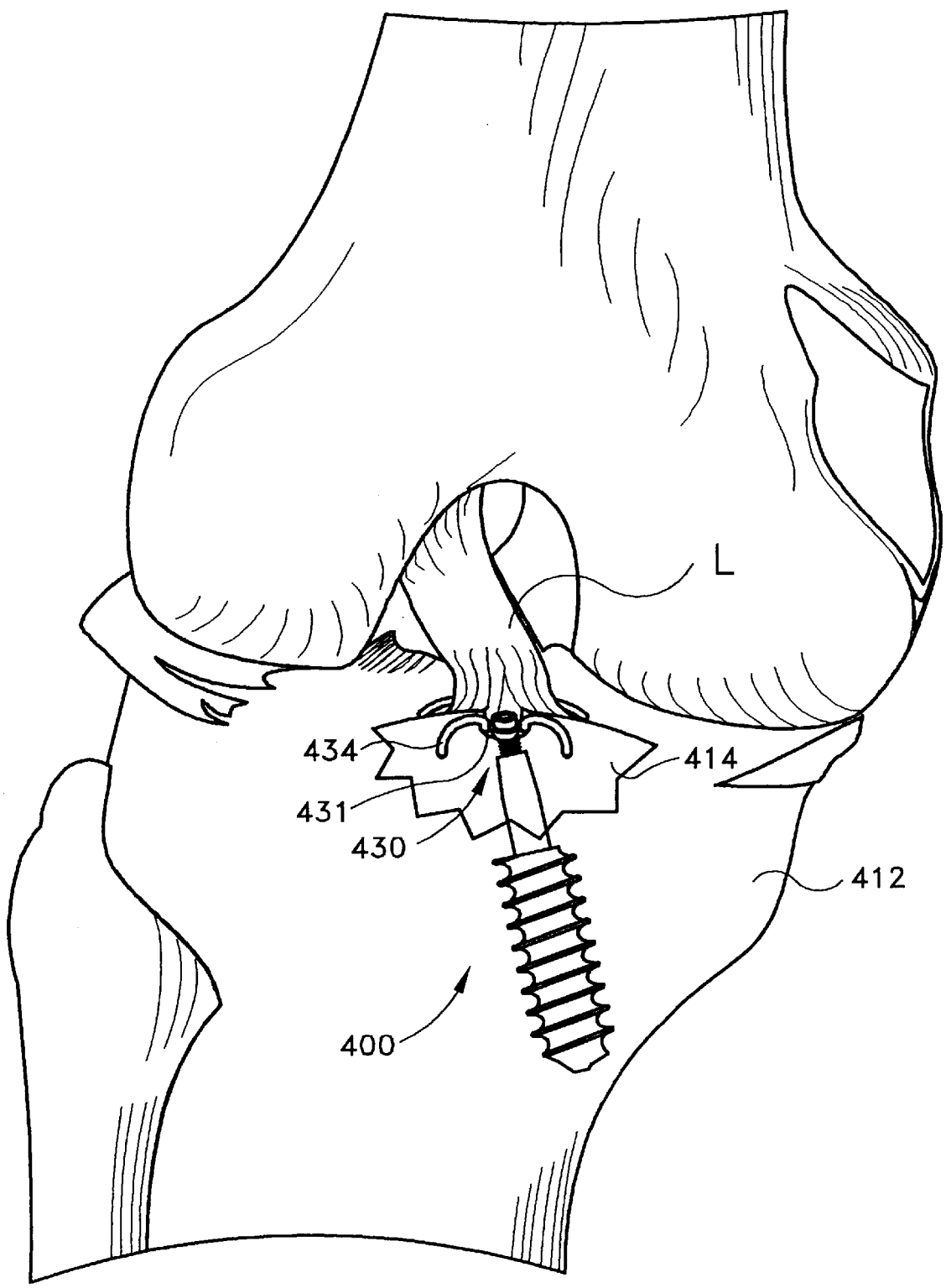
FIG. 64 is a perspective view of another embodiment of the interfragmentary fixation assembly of the present invention.

Notably, the aperture 435 in member 431 is sized and configured such that the member 431 of the second fastener 430 is permitted to rock about the elongated axis of connector 440. As such, the prongs 434 extending radially outwardly from the central section 431 of member 430 are better able to graspingly secure to the bone fragment 414. Moreover, and as shown in FIG. 64, the prong configuration of member 431 readily lends itself to having a ligament L attached thereto.

Frequently, with an acute hyperextension injury to the wrist, the scaphoid will not fracture but instead a series of ligamentous damage can occur about the wrist. The volar wrist ligaments certainly contribute to instability about the wrist. The dorsal scapholunate interosseous ligament is a primary constraining force that when ruptured leads to disassociation between the scaphoid and lunate bones. Failure to reconstruct this ligament can lead to the development of progressive arthritis about the wrist. Another alternative embodiment of the fixation assembly of the present invention readily lends itself to replacement and/or repair of ligaments between adjacent bones. Although a bone-ligament-bone graft is hereinafter illustrated in combination with lunate and scaphoid bones, it should be appreciated that other bones in a patient's body are equally susceptible to the present invention and the present invention should not be limited to that shown for exemplary purposes.

Figure 69:
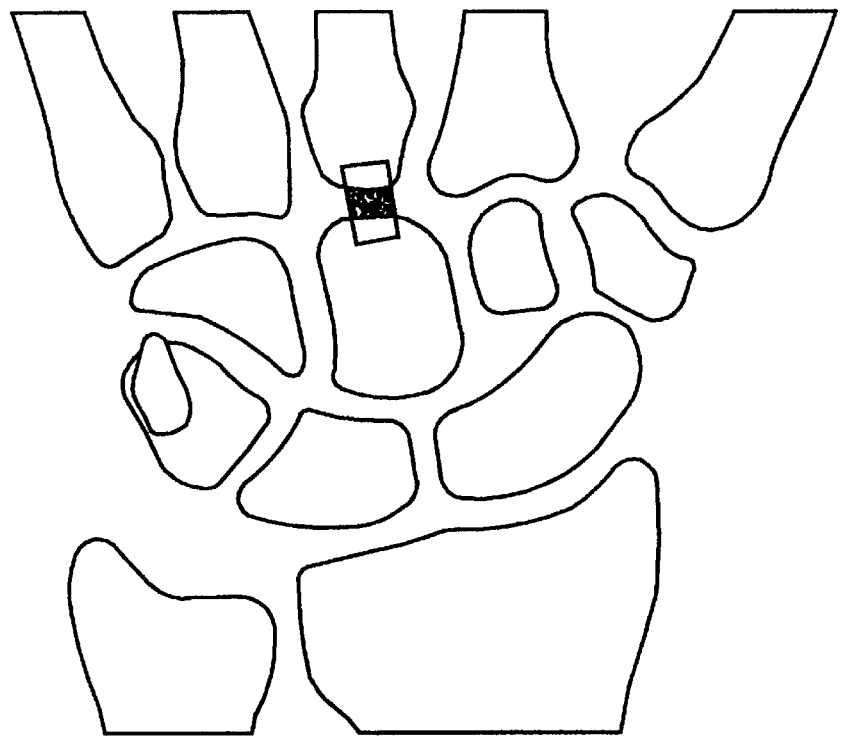
FIG. 69 is a schematic representation of the bones in a patient's hand with a particular area shown for harvesting a section of bone-ligament-bone for grafting.
Figure 70:
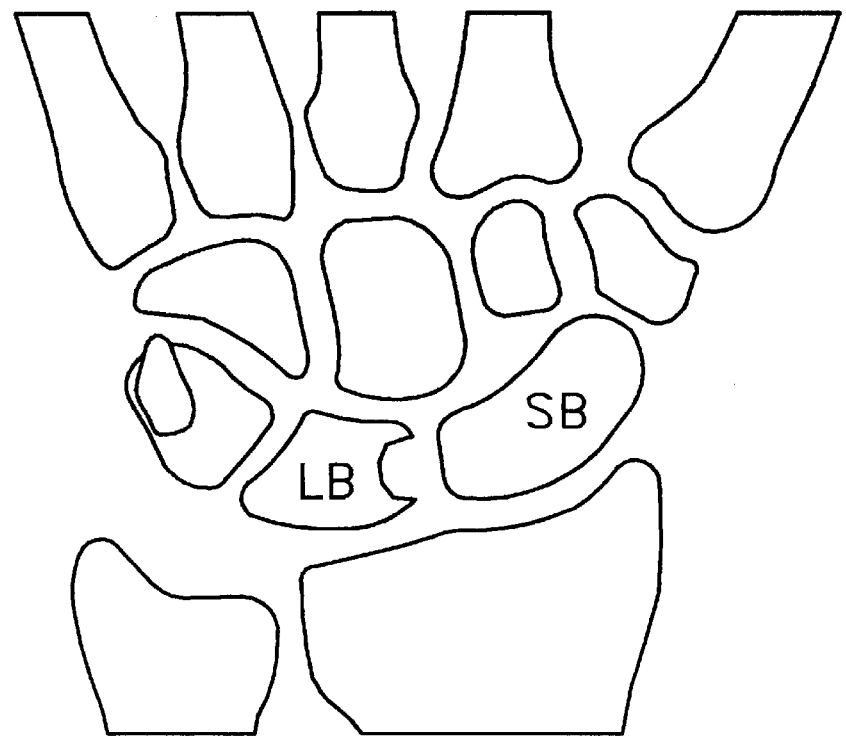
FIG. 70 is a schematic view similar to FIG. 69 but showing a lunate bone channeled to accept a bone-ligament-bone graft.
Figure 71:
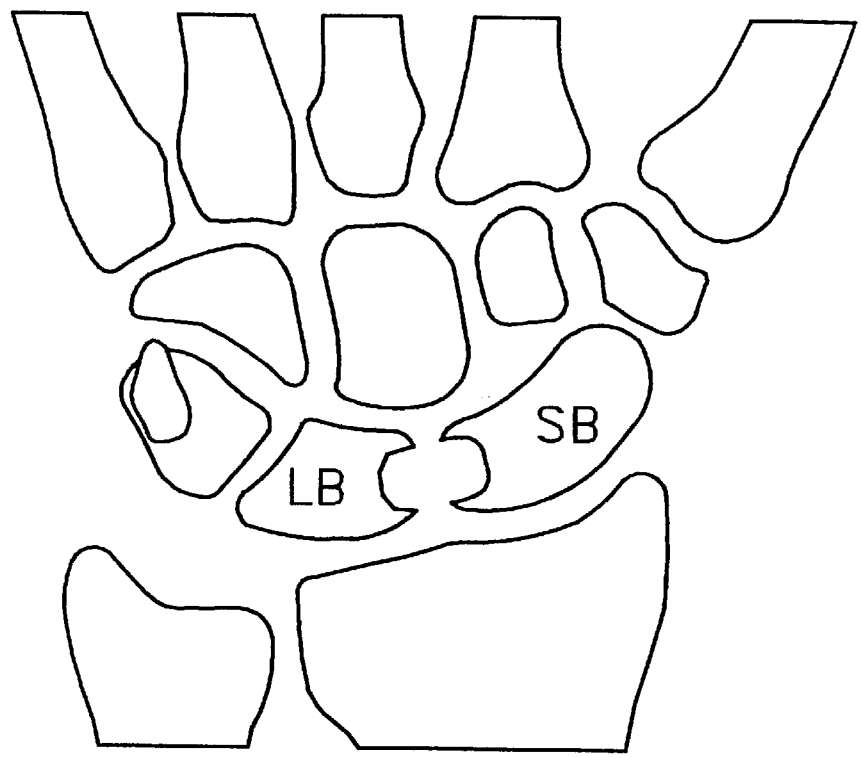
FIG. 71 is a schematic view similar to FIG. 70 but showing a lunate and scaphoid bone channeled to accept a bone-ligament-bone graft.
Figure 72:
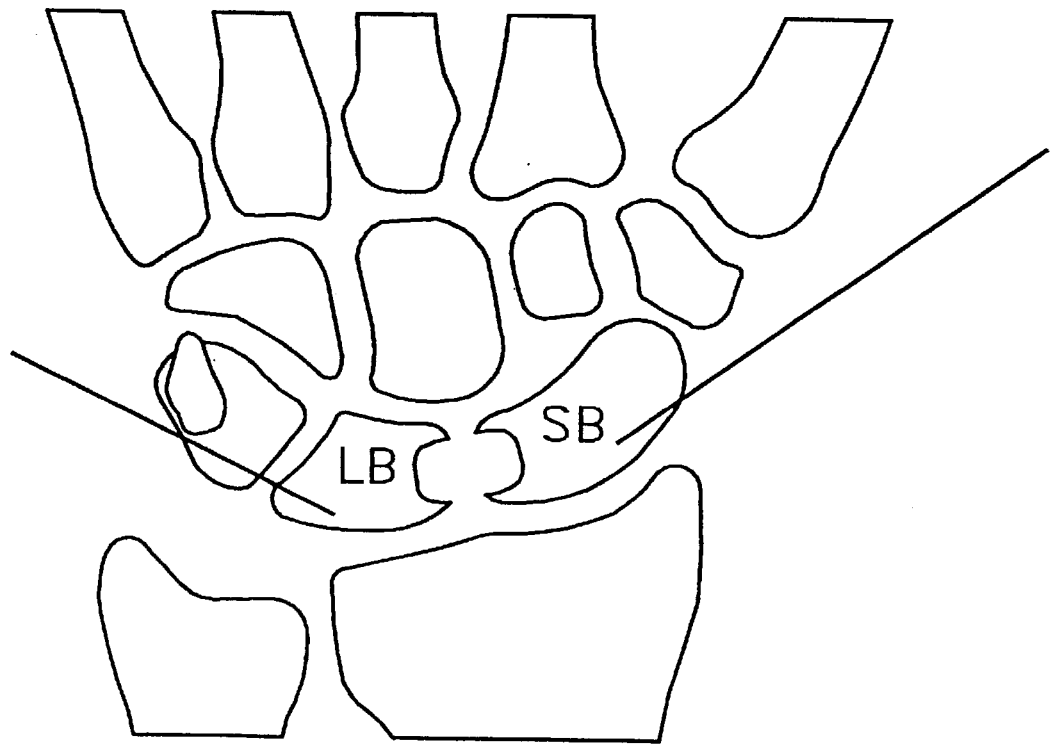
FIG. 72 is a schematic view similar to FIG. 71 but showing K-wires inserted into lunate and scaphoid bones for movement control.

FIG. 69 shows the bones of a patient's hand with a particular area shown for harvesting a bone-ligament-bone for grafting. After the bone-ligament-bone section is harvested, the surgeon configures the lunate bone LB to accept the graft as shown in FIG. 70. The surgeon then conditions or configures the scaphoid bone SB to accept the graft as shown in FIG. 71. As shown in FIG. 72, conventional K-wires are then inserted into the lunate bone and scaphoid bone for movement control.

Another embodiment of the fixation assembly according to the present invention is illustrated in FIGS. 73 through 77 and is designated generally by reference numeral 500. The fixation assembly 500 functions to secure the bone-ligament-bone graft to the lunate bone LB and the scaphoid bone SB. The elements of this alternative embodiment of the fixation assembly 500 that are identical or functionally analogous to other components mentioned above are designated by reference numerals identical to those used above with the exception that this embodiment reference numerals are in the 500 series.

As shown in FIG. 73, this alternative embodiment of the fixation assembly 500 includes a first axially elongated fastener 520, a second fastener 530, a connector 540 and a retaining apparatus 550 (FIG. 77). The first fastener 520, the connector 540 and the retaining apparatus 550 may each be similar to those similar components illustrated in FIGS. 56 through 59 and discussed in detail above. Alteratively, an internal thread form similar to that disclosed in FIGS. 63A and 63B and discussed in detail above could likewise be used to prevent rotation of the connector 540 without detracting or departing from the spirit and scope of the present invention. Thus, no further detailed description need be provided therefor at this time.

This alternative embodiment of the second fastener 530 is best illustrated in FIGS. 73, 74 and 77. The second fastener 530 is formed from a biocompatible material to the bone tissue wherein the fastener is used and preferably from the class consisting of: titanium, stainless steel, or a cobalt chromium molybdenum alloy. As shown, the second fastener 530 comprises a generally planar member 531 having upper and lower generally parallel surfaces 532 and 533. The planar member 531 also defines a preferably centralized through bore 534 that permits a shank portion 544 of connector 540 to pass endwise therethrough and is specifically sized to prohibit the head portion 542 of the connector 540 from passing therethrough. The second fastener 530 is further provided with a plurality of holes or apertures 535 arranged in a generally circumferential relation relative to the centralized through bore 534.

Figure 78:
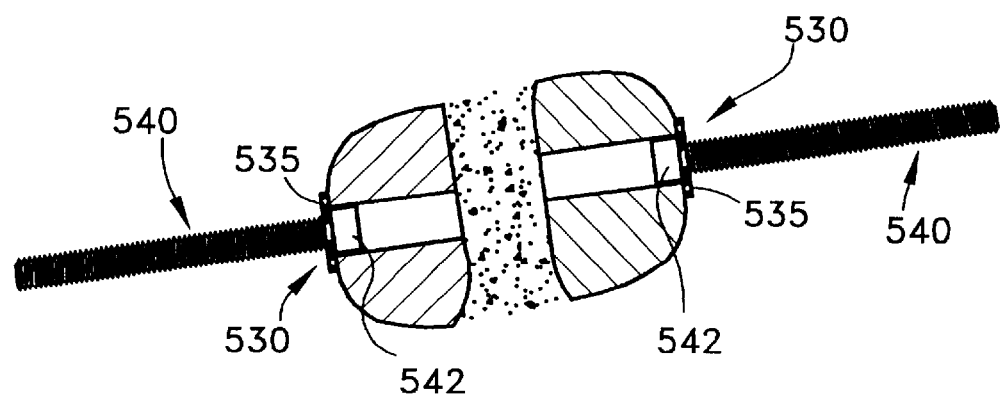
FIG. 78 is a schematic view of a bone-ligament-bone graft shown secured to components parts of alternative embodiments of the second fastener.

Turning now to FIG. 78, the bone-ligament-bone graft is fixedly attached to the second fastener 530. As shown, a bore is provided in each bone fragment of the bone-ligamentbone graft such that access is provided to the head portion 542 of each connector 540. Notably, sutures or other suitable fastening apparatus passes through the apertures 535 in the second fastener and about the bone of the bone-ligament-bone graft thereby securing a bone fragment to the second fastener.

Figure 79:
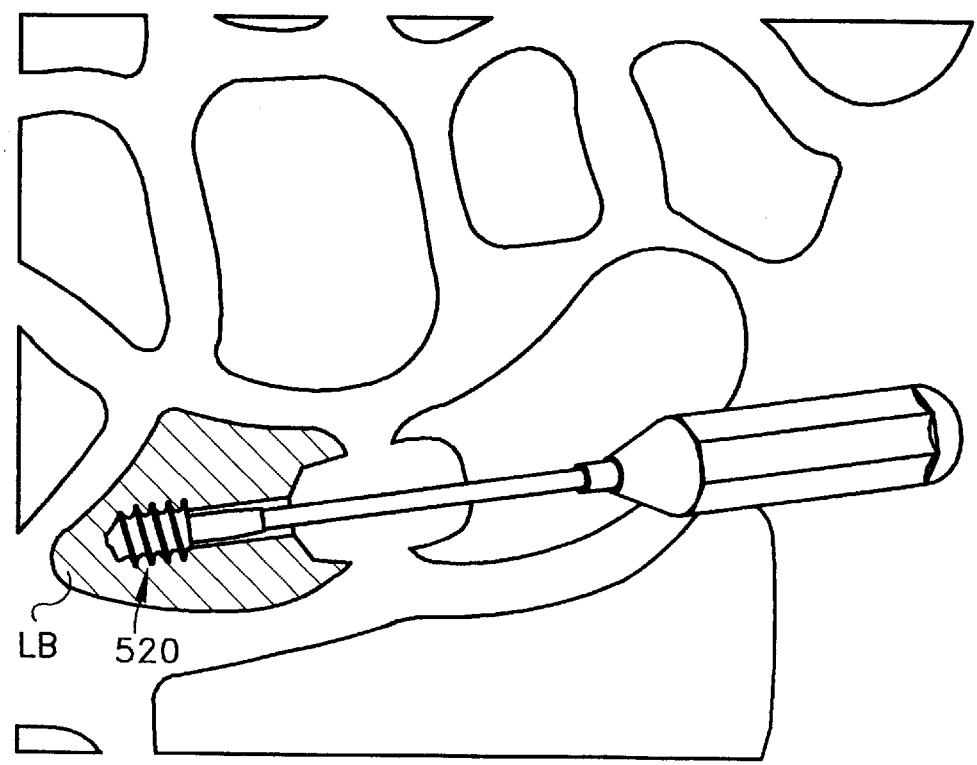
FIG. 79 is a schematic view similar to FIG. 72 (with K-wires omitted for clarity), but showing a first fastener of the interfragmentary fixation assembly inserted into a lunate.
Figure 80:
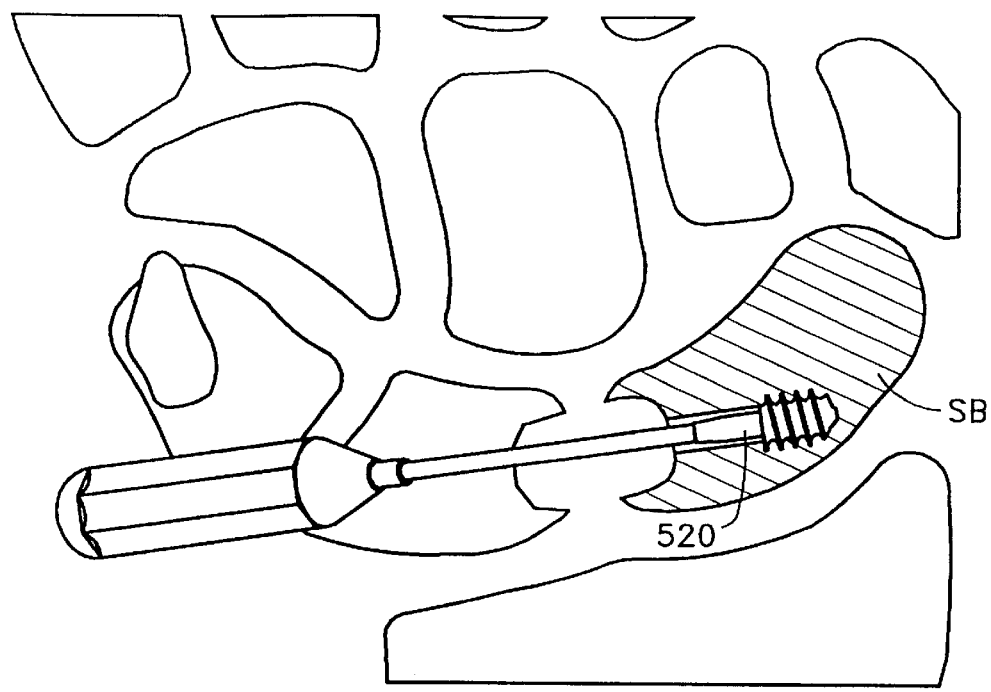
FIG. 80 is a view similar to FIG. 79 with a first fastener of the fixation assembly secured into a scaphoid.

Turning to FIG. 79, after configuring or channelling the lunate bone LB, the first fastener 520 of the fixation assembly is threadably secured within the bone substance of the lunate bone. As shown in FIG. 80, a first fastener 520 of this embodiment of the fixation assembly is threadably secured within the bone substance of the scaphoid bone. Notably, the pitch of the threads on the first fastener 520 prohibit the fastener from becoming dislodged from the bone substance of the respective bone fragment.

Figure 81:
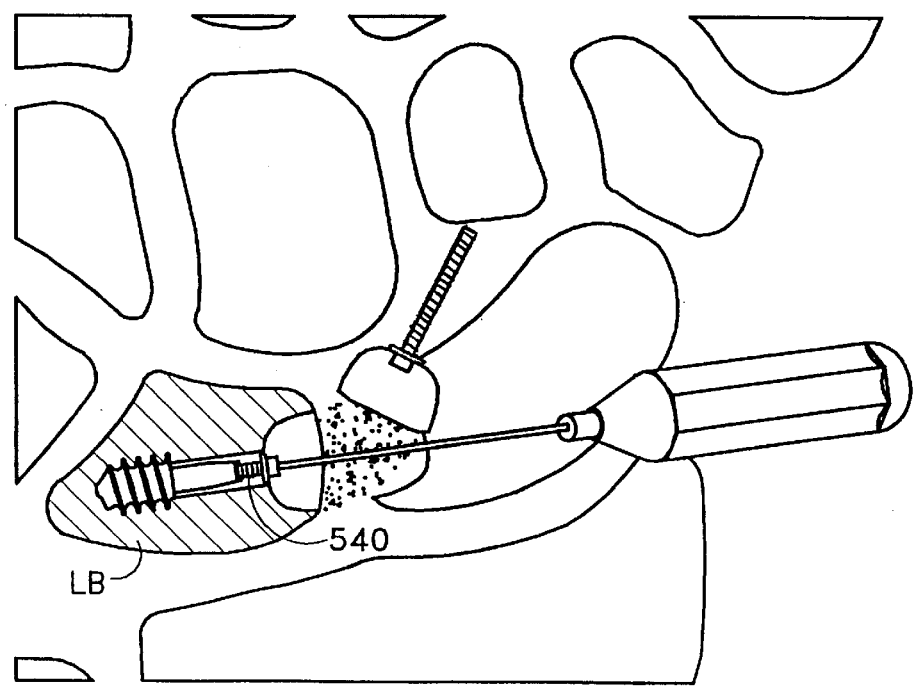
FIG. 81 is a schematic view similar to FIG. 79 showing the fixation assembly of the present invention used to partially attach the bone-ligament-bone graft to a lunate.
Figure 82:
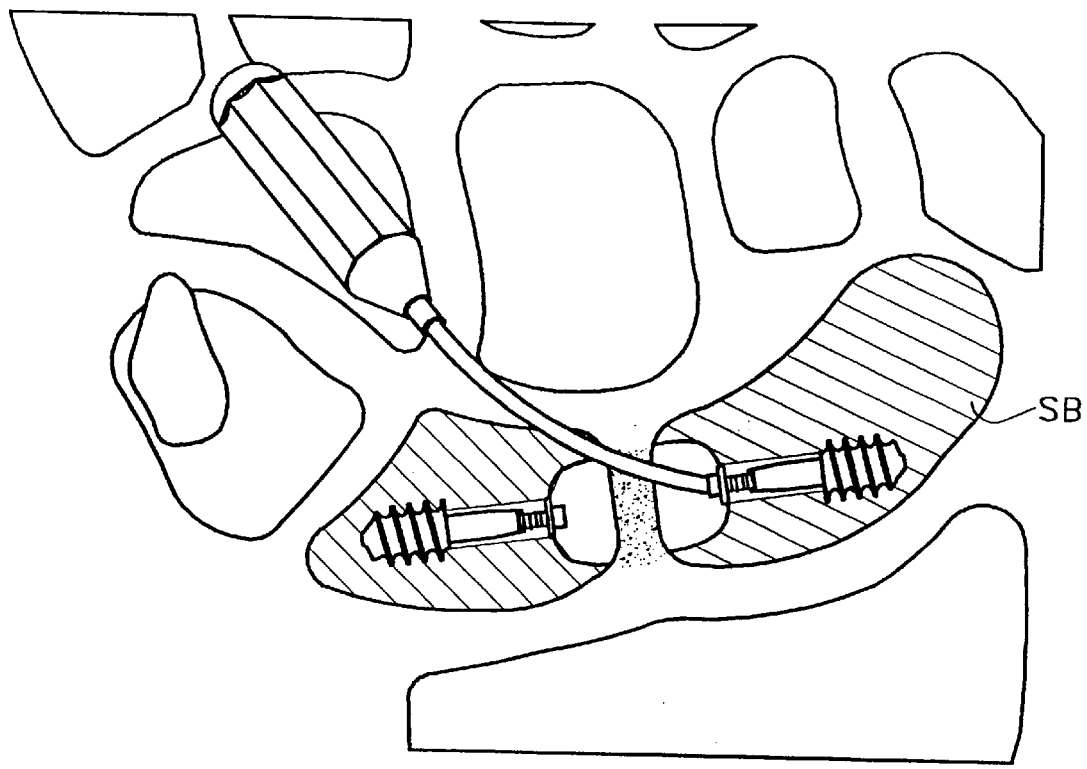
FIG. 82 is a view similar to FIG. 81 but showing another fixation assembly according to the present invention being used to attach an opposite portion of the bone-ligament-bone graft to the scaphoid.
Figure 83:
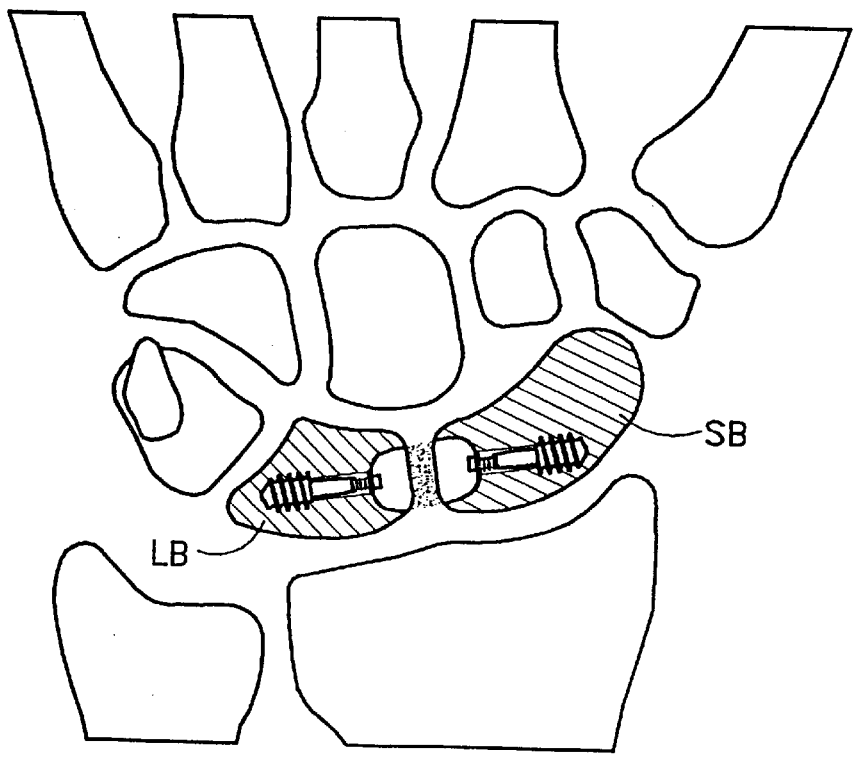
FIG. 83 is a schematic view similar to FIG. 82 but showing a bone-ligament-bone graft procedure completed.

Turning to FIG. 81, the bone-ligament-bone graft is then secured within the channel or configuration of the lunate/scaphoid bone. As shown in FIG. 81, a suitable tool is used to threadably secure the bone graft to the first fastener in the lunate bone. Preferably, such tool includes a flexible shank portion. Because the second fastener is fixedly attached to the bone fragment, the rotating action of the connector 540 forcibly draws the bone fragment into the channelled configuration of the lunate bone LB. Turning to FIG. 82, the other bone fragment is secured in the channelled configuration of the scaphoid bone in a similar manner. FIG. 83 schematically illustrates the bone-ligament-bone graft secured in place between the lunate bone LB and scaphoid bone SB.

Figure 85:
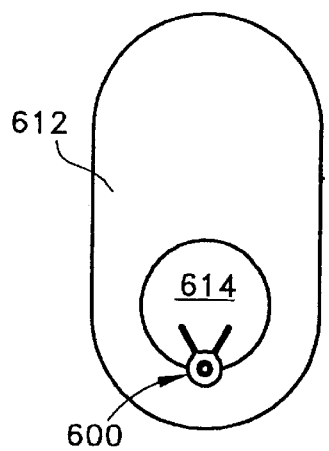
FIG. 85 is an end view of the scaphoid shown in FIG. 84.
Figure 84:
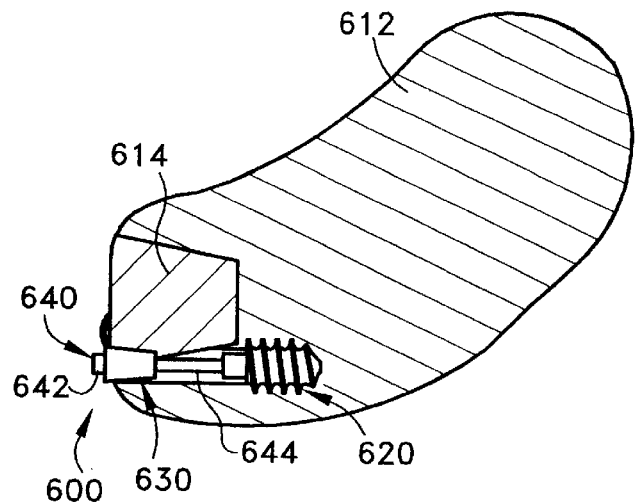
FIG. 84 is a cross section of a scaphoid with another embodiment of the fixation assembly of the present invention having a bone graft attached thereto.

Still another embodiment of the multipiece fixation assembly according to the present invention is schematically illustrated in FIGS. 84 and 85. In this embodiment of the invention, the fixation assembly is utilized to affix a bone plug 614 to a scaphoid bone 612. This alternative embodiment of fixation assembly is schematically illustrated in FIGS. 84 and 85 and is designated generally therein by reference numeral 600. As with the other embodiments of the invention, the fastener assembly 600 functions to maintain the bone plug 614 in a proper compressive relationship relative to the scaphoid bone fragment 612. The elements of this alternative embodiment of the fixation assembly that are identical or functionally analogous to those in earlier embodiments discussed above are designated by reference numerals identical to those used above with the exception that the reference numerals in this alternative embodiment are in the 600 series.

As shown in FIG. 84, this alternative embodiment of the fixation assembly 600 includes a first axially elongated fastener 620, a second fastener 630, a connector 640 and a retainer apparatus (not shown). The first fastener 620, connector 640, and retainer apparatus (not shown) can be like those elements schematically illustrated in FIGS. 56 through 59. Alteratively, an internal thread form similar to that disclosed in FIGS. 63A and 63B and discussed in detail above could likewise be used to prevent rotation of the connector 640 without detracting or departing from the spirit and scope of the present invention.

The alternative embodiment of the second fastener 630 is illustrated in FIGS. 86 through 90. The second fastener 630 comprises a member 631 defining a coaxial bore extending therethrough and having a plurality of prongs extending radially outwardly away from member 631.

In the embodiment illustrated in FIGS. 86 through 90, member 631 of fastener 630 has an axially elongated frusto-conically shaped configuration. Preferably, the prongs 634 extend from that end of member having a larger diameter.

Member 631 of fastener 630 is formed from a biocompatible material preferably from a class of materials comprised of: titanium, stainless steel, or a cobalt chromium molybdenum alloy. Alternatively, an outer surface of the member comprising fasteners 620 and 630 can be treated in a well known manner to promote bone growth.

Figure 86:
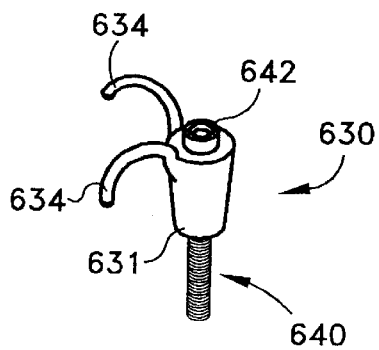
FIG. 86 is a perspective view of an alternative embodiment of the second fastener used in combination with a fixation assembly of the type illustrated in FIG. 84 and having a connector passing endwise therethrough.
Figure 87:
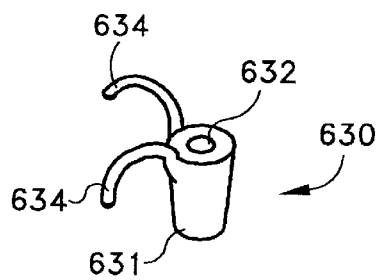
FIG. 87 is a perspective view of the alternative embodiment of the second fastener illustrated in FIG. 86.
Figure 88:
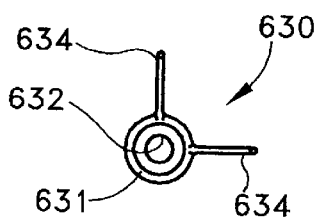
FIG. 88 is a bottom plan view of the second fastener illustrated in FIG. 87.
Figure 89:
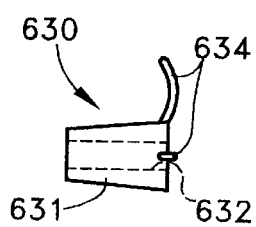
FIG. 89 is an elevational view of the second fastener illustrated in FIG. 87.
Figure 90:
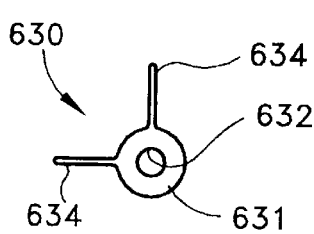
FIG. 90 is a top plan view of the second fastener illustrated in FIG. 87.

As shown in FIG. 86, the throughbore or aperture 632 defined by member 631 of the second fastener 630 is specifically sized relative to the connector 640. More specifically, the throughbore 632 is sized to allow an externally threaded shank portion 644 of connector 640 to extend axially through the second fastener 630 and into threaded engagement with the internal threading (not shown) of the first fastener 620. The head portion 642 of the connector 640 is prohibited, however, from passing endwise through the second fastener 630.

With this embodiment of the invention, the bone plug 614 is placed into the configured channel of the scaphoid bone 612. Thereafter, the first fastener 620 is secured within the bone substance of the bone fragment 612 in a manner discussed in detail above. Thereafter, the threaded connector 640 is passed through the second fastener and threadably engaged with the first fastener. As will be appreciated, rotation of the connector 640 will draw the second fastener 630 toward the first fastener 620 thereby allowing the prong 634 on the second fastener to forcibly move the bone plug 614 into compressive relationship relative to the bone fragment 612. Continued rotation of the connector 640 will continue until the surgeon develops the appropriate "feel" of the fasteners 620, 630 relative to each other thereby establishing a predetermined level of compression between the fasteners and, thus, the bone plug 614 and bone fragment 612. As discussed in detail above, the retaining apparatus (not shown) associated with this embodiment of the invention will maintain the first and second fastener 620 and 630, respectively, in the predetermined compressive relationship by prohibiting the connector 640 from turning thereby maintaining the bone plug 614 and bone fragment 612 in a predetermined compressive relationship during the healing process and in a manner promoting tissue growth therebetween.

FIGS. 91 through 99 schematically illustrate other forms of fasteners that would be equally applicable for use with this embodiment of the invention.

Figure 100:
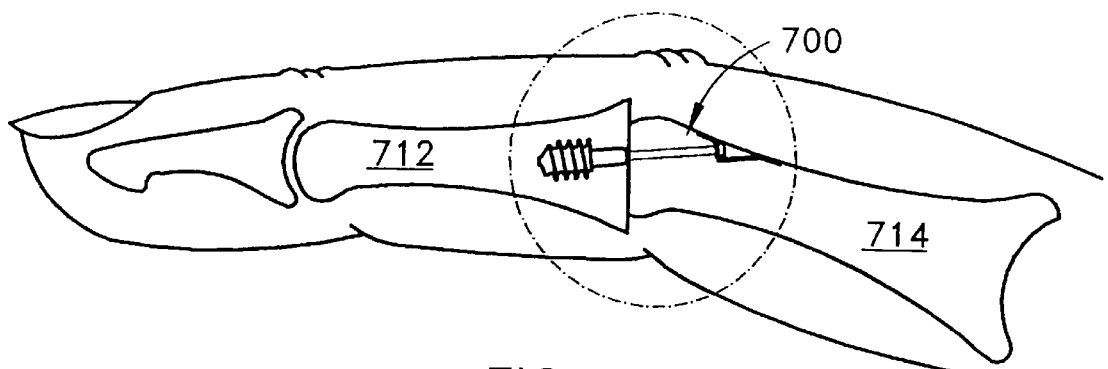
FIG. 100 is a schematic view showing an alternative embodiment of the fixation assembly as used in combination with a small joint arthrodesis.

Another alternative embodiment of the present invention is likewise useful regarding repair of a small joint such as in the finger of a patient. As shown in FIG. 100, this alternative embodiment of the fixation assembly of the present invention is used to secure bone 712 to bone 714 under a predetermined compressive force.

Figure 101:
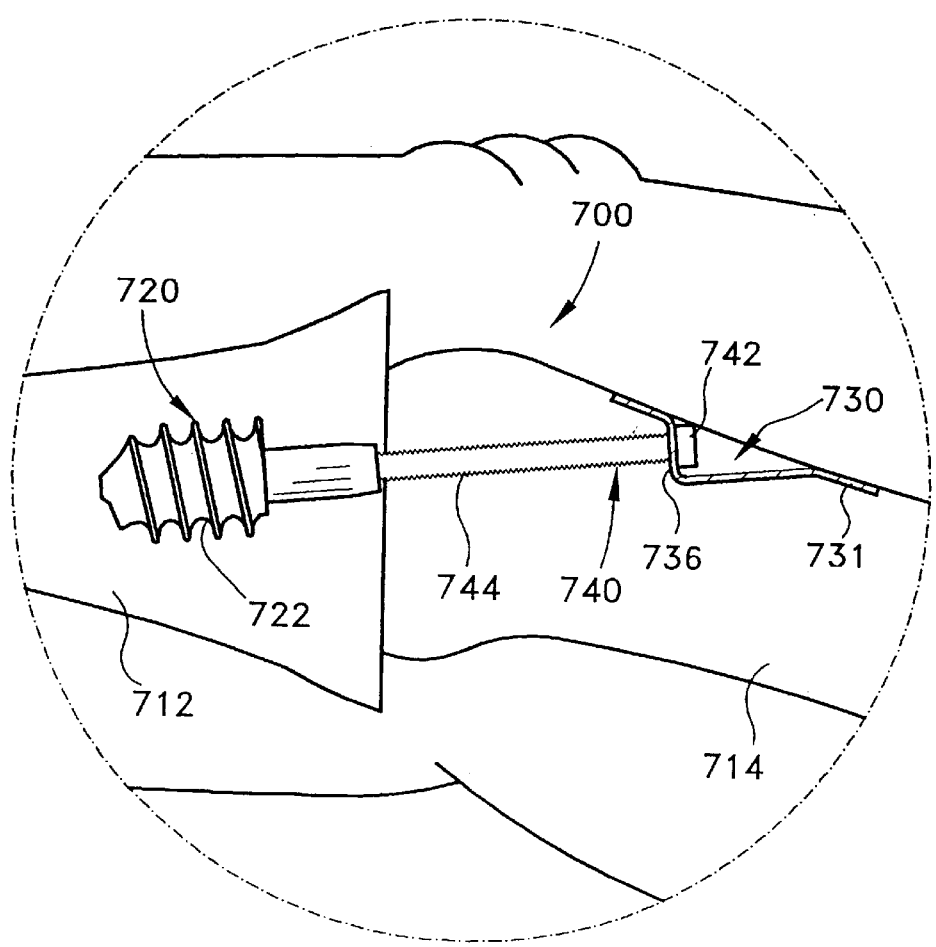
FIG. 101 is an enlarged view of that area encircled in FIG. 100.

For use in combination with such an environment, an alternative embodiment of the multi-piece fixation assembly according to the present invention is illustrated in FIGS. 100 and 101 and is designated generally by reference numeral 700. The fixation assembly 700 is similar, and functions in a similar manner, to the other embodiments of the fixation assembly described above. The elements of this alternative embodiment of the fixation assembly 700 that are identical or functionally analogous to those of other embodiments of the fixation assembly are designated by reference numerals identical to those used for the alternative embodiments with the exception that this embodiment reference numerals are in the 700 series. As shown in FIG. 101, this alternative embodiment of the fixation assembly 700 includes the first axially elongated fastener 720 secured to bone 712, a second fastener 730 fixedly attached to bone 714, a connector 740 for interconnecting the first and second fasteners 720 and 730, respectively, and a retaining apparatus (not shown).

The first fastener 720, the connector 740 and the retainer apparatus (not shown) used in combination with this embodiment of the invention are substantially similar to those components schematically illustrated in FIGS. 56 through 59 and discussed in detail above. Alternatively, a thread form similar to that disclosed in FIGS. 63A and 63B and discussed in detail above could be used to prevent inadvertent rotation of the connector 740 without detracting or departing from the spirit and scope of the present invention. Therefore, no further detail description need be provided therefor for complete understanding of the present invention.

Figure 102:
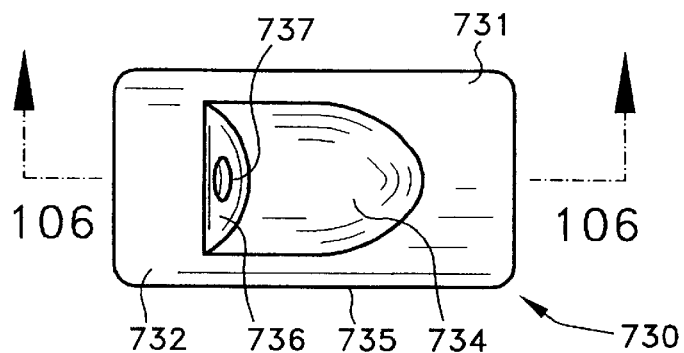
FIG. 102 is a top plan view of an alternative embodiment of the second fastener.
Figure 103:
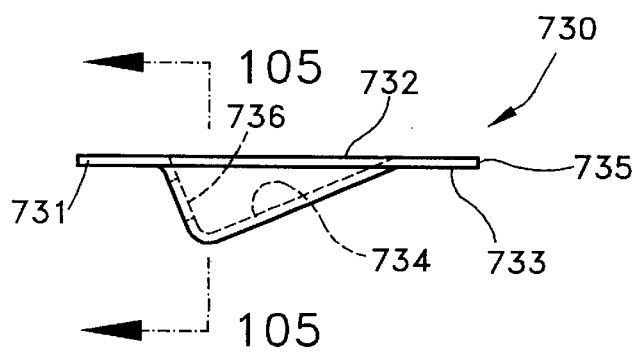
FIG. 103 is an elevational view of the alternative embodiment of second fastener illustrated in FIG. 102.
Figure 104:
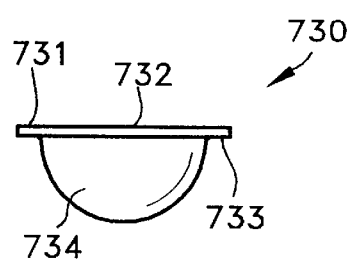
FIG. 104 is a right end view of the second fastener illustrated in FIG. 102.
Figure 105:
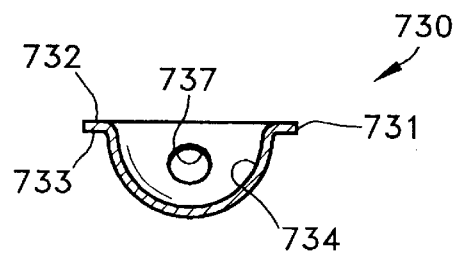
FIG. 105 is a sectional view taken along line 105—105 of FIG. 103.
Figure 106:
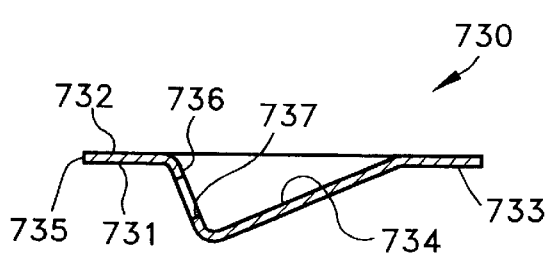
FIG. 106 is a sectional view taken along line 106—106 of FIG. 102.

The alternative embodiment of the second fastener 730 is illustrated in FIGS. 102 through 106. The second fastener 730 is formed from a bone compatible material preferably chosen from the class consisting of: titanium, stainless steel, or a cobalt chromium molybdenum alloy and is attachable to an exterior of the second bone 714 (FIG. 101). As shown in FIGS. 102 through 104, the second fastener 730 comprises an elongated and narrowed plate-like member 731. Member 731 has upper and lower generally parallel surfaces 732 and 733, respectively. The plate-like member 731 further includes an indentation 734 preferably extending longitudinally of member 731 and has a closed margin defined within the periphery 735 of member 731 and including a wall 736 depending in an acute angle relative to the upper surface 732 of the plate-like member 731. The depending wall 736 defines an aperture 737.

Notably, the aperture 737 defined by the plate-like member 731 is sized such that the shank portion 744 (FIG. 101) of the connector 740 is permitted to endwise pass therethrough. Moreover, the aperture 737 in plate-like member 731 is sized such that the head portion 742 (FIG. 101) of the connector 740 is prevented from passing endwise therethrough. Instead, the head portion 742 of connector 740 abuts with the depending wall 736 of the plate-like member 731.

Returning to FIG. 101, the first fastener 720 is secured in the bone substance of bone 712. Notably, the external threading 722 on the first fastener 720 is sufficient to prevent the fastener 720 from becoming dislodged from the bone substance when subjected to axial forces applied thereagainst. Next, the surgeon configures the bone fragment 714 to accept the indentation 734 defined by the plate-like member 731. More specifically, the bone 714 is configured with a step against which wall 736 is permitted to abut. Thereafter, the shank portion 744 of connector 740 passes through bore 737 and into threaded engagement with the first fastener 720.

It will be appreciated at this point in the procedure that some degree of gap or separation may exist between bones 712 and 714. Notably as mentioned above, the head end or portion 742 of connector 740 is larger than bore 737 defined by depending wall 736 of indentation 734 thus preventing passage of the head portion 742 of connector 740 past the wall 736 of plate-like member 731. Any gap or separation existing between the bone 712 and 714 is narrowed by the surgeon rotating the connector 740. That is, with the head portion 742 of connector 740 in operable engagement with wall 736 of plate-like member 731 and with wall 736 abutting against the configured bone 714, continued rotation of the connector 740 will cause and result in the first and second fasteners 720 and 730, respectively, and the bones attached to each being drawn toward each other. Ultimately, the bone 712 and 714 are preferably drawn into abutting relationship under a predetermined compression relative to each. Since the fasteners 720 and 730 are already fixed to the bone substance of each bone 712 and 714, the ability to rotate the connector 740 allows the surgeon an appropriate "feel" when the bones 712, 714 are drawn into a predetermined and proper compressive relationship relative to each other. Moreover, the retaining apparatus (not shown) associated with this embodiment of the invention prevents the connector 740 from inadvertently turning thus maintaining the predetermined compressive relationship between the fasteners 720 and 730 and the bones 712 and 714, respectively, connected to each.

Another aspect of the present invention relates to providing an interfragmentary fixation kit as schematically illustrated in FIG. 107. The interfragmentary fixation kit comprises a collection of first axially elongated fasteners. Each fastener in the collection has an elongated length that is different from the elongated length of other fasteners in the collection. Notably, each fastener in the collection has external threading for anchoring the first fastener into a bone fragment. The configuration of the external threading of each fastener in the collection may differ from other fasteners in the collection. Accordingly, the surgeon is permitted to choose from the interfragmentary fixation kit the appropriate sized fastener. The interfragmentary fixation kit further includes a series of second fasteners. Each of said second fasteners in the series is adapted for attachment in nonmovable relation to the second bone in the patient and has a different configuration than the other fasteners in the series of second fasteners, thus yielding a selection from which the surgeon can chose the most appropriate fastener from the particular fracture being repaired. Moreover, a set of elongated connectors are provided in combination with the interfragmentary fixation kit. Each connector in the set of connectors has a head portion that accommodates a driving tool and an elongated lengthwise shank portion having external uniformly pitched threading that corresponds to the internal threading of each fastener in the collection of first fasteners. Understandably, the length of the shank portion of each connector in the set of connectors varies from one another to allow various fasteners to be used in combination relative to each other. Accordingly, the surgeon is permitted to mix and match sets of components to the appropriate circumstances which require repair.

Regardless of the particular fixation assembly embodiment used, the multipiece interfragmentary fixation assembly permits first and second bone fragments to be connected under compression. Another important feature of the present invention is that the interfragmentary fixation assembly allows the bone fragments to be interconnected under adjustable compression that is preselected by the surgeon during the connection process. Thus, with the present invention, the surgeon is provided with a "feel" for the level or degree of compression to be established between the fasteners and, thus, bone fragments to promote healing of bone fragments. Although some of the components of the fixation assembly of the present invention are completely buried within the bone substance of the bone fragments requiring repair, a salient feature of the present invention is the provision of a retainer mechanism that maintains the predetermined level of compression between the fasteners by preventing the connector between the fasteners from inadvertently turning.

From the foregoing, it will be observed that numerous modifications and variations can be effected without departing from the true spirit and scope of the novel concept of the present invention. It will be appreciated that the present disclosure is intended as an exemplification of the invention, and is not intended to limit the invention to the specific embodiment illustrated. The disclosure is intended to cover by the appended claims all such modifications as fall within the scope of the claims.

What is claimed is:

1. A multipiece interfragmentary fixation assembly for connecting portions of bone across a fracture therebetween, said interfragmentary fixation assembly comprising:

a first axially elongated fastener defining an elongated axis and having external threading for anchoring said first fastener into a first bone fragment, said first fastener defining an coaxial opening with internal uniformly pitched threading extending along at least a portion of the length thereof;

a second fastener attachable in non-movable relation with a second bone fragment;

an elongated connector including a head portion that accommodates a tool and a shank portion having external uniformly pitched threading corresponding to the internal threading of said first fastener, and wherein the shank portion of said connector extends endwise through the second fastener and into threaded engagement with said first fastener while the head portion of said connector operably engages with said second fastener such that rotation of said connector draws the first and second fasteners and thereby the first and second bone fragments into compressive and proper relation relative to each other; and a retaining apparatus for preventing said connector from inadvertently rotating relative to said second fastener thereby maintaining the proper compressive relationship between the fasteners and the bone fragments.

2. The multipiece interfragmentary fixation assembly according to claim 1 wherein a leading end of said first fastener has a pointed configuration while a trailing end of said first fastener is configured to accommodate a driving tool capable of turning said first fastener such that the external threading threadably engages with said first bone fragment.

3. The multipiece interfragmentary fixation assembly according to claim 1 wherein said second fastener has an elongated configuration with external threading for anchoring said second fastener in said second bone fragment.

4. The multipiece interfragmentary fixation assembly according to claim 3 wherein said second fastener has a coaxial opening extending between leading and trailing ends thereof.

5. The multipiece interfragmentary fixation assembly according to claim 4 wherein the trailing end of said second fastener is configured to accommodate a driving tool capable of turning said second fastener such that the external threading threadably engages with said second bone fragment.

6. The multipiece interfragmentary fixation assembly according to claim 4 wherein said retaining apparatus comprises an insert fitted within said coaxial opening and operably associated with said second fastener for preventing inadvertent rotation of said connector thereby maintaining the proper compressive relationship between the fasteners and the bone fragments.

7. The multipiece interfragmentary fixation assembly according to claim 1 wherein said second fastener comprises a member formed from a bone compatible material and configured with a generally concave shaped section that is generally centralized between multiple prongs extending radially away from said central section, and an apertured hemi-spherically shaped element that is seated for rocking movement within said central section of said member, and wherein the shank portion of said elongated connector extends endwise through the said member and said element into threaded engagement with said first fastener, with the head portion of said connector being operably engagable with said element such that rotation of said connector draws the member and said first fastener and the respective bone fragments engaged by each toward and into compressive relationship relative to each other.

8. The multipiece interfragmentary fixation assembly according to claim 7 wherein the concave centralized section of said member defines an enlarged opening that permits said member to rock relative to said connector and said element thereby enhancing attachment of said prongs to said second bone fragment.

9. The multipiece interfragmentary fixation assembly according to claim 1 wherein said retaining apparatus comprises a non-metallic insert disposed along the length of the coaxial opening of said first fastener for engaging the external threading on said connector and thereby preventing inadvertent rotation of said connector.

10. The multipiece interfragmentary fixation assembly according to claim 1 wherein said second fastener comprises an apertured disk that fits about the shank portion of said connector and operably engages an underside of the head portion of said connector to permit relative rotation therebetween, the apertures in said disk permitting said second bone fragment to be attached thereto.

11. The multipiece interfragmentary fixation assembly according to claim 1 wherein said second fastener comprises an elongated member having first and second ends and an axial bore for allowing the shank portion of said connector to extend endwise therethrough and into threaded engagement with said first fastener, the elongated member of said second fastener further including a bone fragment retainer extending radially away from said elongated member.

12. The multipiece interfragmentary fixation assembly according to claim 11 wherein the elongated member of said second fastener has a generally cylindrical configuration between opposite ends thereof.

13. The multipiece interfragmentary fixation assembly according to claim 11 wherein the elongated member of said second fastener has a frusto-conical configuration between opposite ends thereof.

14. The multipiece interfragmentary fixation assembly according to claim 1 wherein said second fastener comprises a plate having upper and lower generally parallel surfaces with an indentation having a closed margin defined by said plate and including a wall depending at an acute angle relative to the upper surface of said plate, said wall defining an aperture through which the shank portion of said connector extends into threaded engagement with the internal threading of said first fastener while the wall of said indentation maintains the head portion on an opposite side of said plate from said first fastener.

15. A multipiece interfragmentary fixation assembly for interconnecting first and second bone fragments to each other across a fracture defined therebetween, said interfragmentary fixation assembly comprising:

a first axially elongated fastener formed from a bone compatible material and having external threading for anchoring said first fastener within an interior of the first bone fragment, said first fastener defining an opening with internal uniformly pitched threading;

a second fastener formed from a bone compatible material and attachable to an exterior of the second bone fragment, said second fastener comprising a member configured with a generally concave shaped and apertured section that is generally centralized between prongs extending radially outward and away from the central section of said member, said second fastener further including an apertured hemi-spherically shaped element configured to rockingly seat within the central section of said member;

an elongated screw connector including an enlarged head portion that accommodates a driving tool and an elongated threaded shank portion having external uniform pitched threading extending over the length thereof corresponding to the internal threading of said first fastener, and wherein the shank portion of said connector extends endwise through the apertured element and the apertured center section of the member of said second fastener and into threaded engagement with said internal threading of said first fastener while the enlarged head portion of said connector operably engages with the element of said second fastener such that rotation of said connector draws the first and second fasteners and thereby the first and second bone fragments toward and into preselected compressive relationship relative to each other, and wherein the apertured center section of the member of said second fastener is configured to allow said member to rock relative to said element with the connector passing therethrough to enhance the ability of the prongs of said member to positively engage the exterior of said second bone fragment to the fullest extend possible; and wherein said first fastener further includes a retaining apparatus arranged along the internal threading thereof for operably engaging the external threading of said connector and thereby preventing inadvertent rotation of said connector thus maintaining the preselected compressive relationship between said first and second fasteners and the first and second bone fragments attached thereto.

16. The multipiece interfragmentary fixation assembly according to claim 15 wherein said retaining apparatus comprises a non-metallic ring arranged along the length of the internal threading of said first fastener for operably engaging the external threading of said connector and thereby preventing inadvertent rotation of said connector thus maintaining the preselected compressive relationship between the first and second fasteners.

17. A multipiece interfragmentary fixation assembly for connecting portions of bone across a fracture therebetween, said interfragmentary fixation assembly comprising:

an axially elongated fastener having external threading for anchoring said first fastener into a first bone fragment, said first fastener defining a coaxial opening with internal uniformly pitched threading extending the length thereof;

a generally planar member having upper and lower generally parallel surfaces, said planar member defining a generally centralized throughbore with a plurality of apertures arranged in generally circumferential relation relative to said throughbore;

an elongated connector including an enlarged head portion that accommodates a driving tool and is configured to prevent its movement through said throughbore of said planar member but is smaller than the spacings between opposed apertures defined by said planar member, said connector further including a shank portion defining an elongated axis and that is sized to extend endwise through said throughbore defined by said planar member whereby said planar member is free to turn beneath said enlarged head of said member about said axis defined by said shank portion, and wherein said shank portion has external uniformly pitched threading corresponding to the internal threading of said first fastener; and a retaining apparatus arranged along the internal threading thereof for operably engaging the external threading of said connector and thereby preventing inadvertent rotation of said connector relative to said fastener.

18. A multipiece interfragmentary fixation assembly for interconnecting first and second bone fragments, comprising:

a first bone screw having external threading for anchoring said first bone screw in said first bone fragment, said first bone screw defining an axial bore having uniformly pitched internal threading along the majority length thereof;

a second bone screw having external threading for anchoring said second bone screw in said second bone fragment, said second bone screw defining an axial bore extending therethrough;

an elongated connector including a head portion that is configured to accommodate a tool and an elongated shank portion with external uniformly pitched threading that corresponds to the internal threading of said first screw, and wherein the shank portion of said connector extends endwise through the axial bore defined by said second fastener and into threaded engagement with said the axial bore defined in said first fastener while the head of the connector operably engages with the second fastener such that rotation of said connector draws said first and second fasteners and thereby the first and second bone fragments toward and into compressive relationship relative to each other; and a retainer apparatus for preventing said connector from turning relative to said second fastener thereby maintaining the proper compressive relationship between the fasteners and the bone fragments.

19. The multipiece interfragmentary fixation assembly according to claim 18 wherein a first end of said first bone screw has a pointed configuration while a second end of said first bone screw is configured to accommodate a driving tool capable of turning said first bone screw such that the external threading engages with said first bone fragment.

20. The multipiece interfragmentary fixation assembly according to claim 18 wherein the external threading on said first and second bone screws generally correspond relative to each other.

21. The multipiece interfragmentary fixation assembly according to claim 18 wherein a trailing end of the axial bore defined by said second bone screw is configured to accommodate a driving tool capable of turning said second bone screw such that the external threading threadably engages with said second bone fragment.

22. The multipiece interfragmentary fixation assembly according to claim 18 wherein the axial bore defined by said second bone screw has a first lengthwise portion that opens to a trailing end of said second bone screw and has a non-circular cross-sectional configuration that is sized to allow the head portion and shank portion of said connector to pass endwise therethrough and a second lengthwise portion that opens to a leading end of said second bone screw and is sized to allow only said shank portion of said connector to pass endwise therethrough.

23. The multipiece interfragmentary fixation assembly according to claim 22 wherein said retainer apparatus comprises a element having a cross-sectional configuration generally corresponding to the cross-section of the first portion of the axial bore defined by said second bone screw whereby said element is prevented from turning relative to said second bone screw, said element having a pliant annular ring that operably engages with said second bone screw for preventing the connector from inadvertently turning in a direction whereby loosening the compressive relationship between the fasteners beyond a preset amount.

24. The multipiece interfragmentary fixation assembly according to claim 22 wherein the head portion of said connector defines a socket and an annular recess radially extending outwardly from the socket, and wherein said retainer apparatus comprises an element having a cross-sectional configuration generally corresponding to the cross-section of the first portion of the axial bore defined by said second bone screw whereby said element is prevented from turning relative to said second bone screw, said element having a pliant annular ring that operably engages with the annular recess in the socket defined by said connector, and wherein said element further includes a finger that axially extends from said element into said socket and operably engages with said connector for preventing said connector from turning relative to said second member.

25. The multipiece interfragmentary fixation assembly according to claim 24 wherein said element includes a plurality of fingers that axially extend from one end of said element and into the socket and operable engagement with said connector for preventing inadvertent turning movement of said connector relative to said second bone screw.

26. The multipiece interfragmentary fixation assembly according to claim 18 wherein said retaining apparatus comprises a non-metallic insert disposed along the length of the internal threading of said axial bore for engaging the external threading on said connector and thereby preventing inadvertent rotation of said connector.

27. A multipiece interfragmentary fixation assembly for interconnecting first and second bone fragments, comprising:
a first bone screw having external threading axially extending away from a proximal end of said first screw along a lengthwise portion of said screw for anchoring said first bone screw in said first bone fragment and a reduced diameter portion extending from said external threading to a distal end of said first screw, with said reduced diameter portion of said screw having an axially tapering configuration along an outer surface thereof, said first bone screw defining an axial bore having uniformly pitched internal threading along the majority length thereof;
a second bone screw having external threading axially extending away from a distal end of said second screw and along a lengthwise portion of said second screw for anchoring said second bone screw in said second bone fragment and a reduced diameter portion extending from said external threading to a proximal end of said second screw, said second bone screw defining an axial bore extending therethrough, and wherein the axial bore defined by said second screw includes a counterbore portion extending axially away from the distal end of said screw, said counterbore having an axially tapered configuration that complements the tapered configuration on the reduced diameter portion of said first screw;
an elongated connector including a head portion that is configured to accommodate a tool and an elongated shank portion with external uniformly pitched threading that corresponds to the internal threading of said first screw, and wherein the shank portion of said connector extends endwise through the axial bore defined by said second fastener and into threaded engagement with said the axial bore defined in said first fastener while the head of the connector operable engages with the second fasteners such that rotation of said connector draws said first and second fasteners and thereby the first and second bone fragments toward and into a predetermined compressive relationship relative to each other and with the reduced diameter portion of said first screw fitting axially into the counterbore portion defined by said second screw whereby effecting alignment of the bone fragments relative to each other.

28. The multipiece interfragmentary fixation assembly according to claim 27 further including a retaining apparatus for preventing said connector from inadvertently rotating relative to said bone screws thereby maintaining the predetermined compressive relationship between the screws and the bone fragments attached thereto.

29. The multipiece interfragmentary fixation assembly according to claim 27 wherein a trailing end of the axial bore defined by said second bone screw is configured to accommodate a driving tool capable of turning said second bone screw such that the external threading threadably engages with said second bone fragment.

30. The multipiece interfragmentary fixation assembly according to claim 27 wherein the axial bore defined by said second bone screw has a first lengthwise portion that opens to a trailing end of said second bone screw and has a non-circular cross-sectional configuration that is sized to allow the head portion and shank portion of said connector to pass endwise therethrough and a second lengthwise portion that opens to a leading end of said second bone screw and is sized to allow only said shank portion of said connector to pass endwise therethrough.

31. The multipiece interfragmentary fixation assembly according to claim 30 wherein said retainer apparatus comprises a element having a cross-sectional configuration generally corresponding to the cross-section of the first portion of the axial bore defined by said second bone screw whereby said element is prevented from turning relative to said second bone screw, said element having a pliant annular ring that operably engages with an annular grove disposed along the length of said first portion of said axial bore defined by said second bone screw for preventing the connector from inadvertently turning in a direction whereby loosening the compressive relationship between the fasteners beyond a preset amount.

32. The multipiece interfragmentary fixation assembly according to claim 30 wherein the head portion of said connector defines a socket and an annular recess radially extending outwardly from the socket, and wherein said retainer apparatus comprises an element having a cross-sectional configuration generally corresponding to the cross-section of the first portion of the axial bore defined by said second bone screw whereby said element is prevented from turning relative to said second bone screw, said element having a pliant annular ring that operably engages with the annular recess in the socket defined by said connector, and wherein said element further includes a finger that axially extends from said element into said socket and operably engages with said connector for preventing said connector from turning relative to said second member.

33. The multipiece interfragmentary fixation assembly according to claim 32 wherein said element includes a plurality of fingers that axially extend from one end of said element and into the socket and operable engagement with said connector for preventing inadvertent turning movement of said connector relative to said second bone screw.

34. The multipiece interfragmentary fixation assembly according to claim 28 wherein said retaining apparatus comprises a non-metallic insert disposed along the length of said coaxial opening for engaging the external threading on said connector and thereby preventing inadvertent rotation of said connector.

35. A multipiece interfragmentary fixation assembly for connecting fragments of bone across a fracture therebetween, said interfragmentary fixation assembly comprising:
- a first axially elongated fastener with external threading for anchoring said first fastener into a first bone fragment;
- a second fastener configured for non-movable attachment to a second bone fragment; and
- a rotatable and elongated connector for drawing the first and second fasteners and thereby the bone fragments attached to each into compressive and proper relationship relative to each other, with the connector and said first fastener being threadably interconnected to each other along at least a portion of their length, and wherein at least a portion of the threadable connection being configured to prevent the connector from inadvertently rotating relative to said first fastener thereby maintaining the proper compressive relationship between the fasteners and the bone fragments.

36. The multipiece interfragmentary fixation assembly according to claim 35 wherein a leading end of said first fastener has a pointed configuration while a trailing end of said first fastener is configured to accommodate a driving tool capable of turning said first fastener such that the external threading threadably engages with said first bone fragment.

37. The multipiece interfragmentary fixation assembly according to claim 35 wherein said second fastener has an elongated configuration with external threading for anchoring said second fastener in said second bone fragment.

38. The multipiece interfragmentary fixation assembly according to claim 37 wherein said second fastener has a coaxial opening extending between leading and trailing ends thereof.

39. The multipiece interfragmentary fixation assembly according to claim 38 wherein the trailing end of said second fastener is configured to accommodate a driving tool capable of turning said second fastener such that the external threading threadably engages with said second bone fragment.

40. The multipiece interfragmentary fixation assembly according to claim 35 wherein said second fastener comprises a member formed from a bone compatible material and configured with a generally concave shaped section that is generally centralized between multiple prongs extending radially away from said central section, and an apertured hemi-spherically shaped element that is seated for rocking movement within said central section of said member, and wherein a shank portion of said elongated connector extends endwise through the said member and said element into threaded engagement with said first fastener, with a head portion of said connector being operably engagable with said element such that rotation of said connector draws the member and said first fastener and the respective bone fragments engaged by each toward and into compressive relationship relative to each other.

41. The multipiece interfragmentary fixation assembly according to claim 40 wherein the concave centralized section of said member defines an enlarged opening that permits said member to rock relative to said connector and said element thereby enhancing attachment of said prongs to said second bone fragment.

42. The multipiece interfragmentary fixation assembly according to claim 35 wherein said second fastener comprises an apertured disk that fits about a shank portion of said connector and operably engages an underside of a head portion of said connector to permit relative rotation therebetween, the apertures in said disk permitting said second bone fragment to be attached thereto.

43. The multipiece interfragmentary fixation assembly according to claim 35 wherein said second fastener comprises an elongated member having first and second ends and an axial bore for allowing a shank portion of said connector to extend endwise therethrough and into threaded engagement with said first fastener, the elongated member of said second fastener further including a bone fragment retainer extending radially away from said elongated member.

44. The multipiece interfragmentary fixation assembly according to claim 35 wherein the elongated member of said second fastener has a generally cylindrical configuration between opposite ends thereof.

45. The multipiece interfragmentary fixation assembly according to claim 35 wherein said second fastener comprises a plate having upper and lower generally parallel surfaces with an indentation having a closed margin defined by said plate and including a wall depending at an acute angle relative to the upper surface of said plate, said wall defining an aperture through which a shank portion of said connector extends into threaded engagement with the internal threading of said first fastener while the wall of said indentation maintains a head portion of said connector on an opposite side of said plate from said first fastener.

46. A multipiece interfragmentary fixation assembly for interconnecting first and second bone fragments to each other across a fracture defined therebetween, said interfragmentary fixation assembly comprising:
- a first axially elongated fastener formed from a bone compatible material and having external threading for anchoring said first fastener within an interior of the first bone fragment;
- a second fastener formed from a bone compatible material and attachable to an exterior of the second bone fragment, said second fastener comprising a member configured with a generally concave shaped and apertured section that is generally centralized between prongs extending radially outward and away from the central section of said member, said second fastener further including an apertured hemi-spherically shaped element configured to rockingly seat within the central section of said member;
- an elongated screw connector including an enlarged head portion that accommodates a driving tool and an elongated and externally threaded shank portion extending endwise through the apertured element and the apertured center section of the member of said second fastener and into threaded engagement with internal threading of said first fastener while the enlarged head portion of said connector operably engages with the element of said second fastener such that rotation of said connector draws the first and second fasteners and thereby the first and second bone fragments toward and into preselected compressive relationship relative to each other, and wherein the apertured center section of the member of said second fastener is configured to allow said member to rock relative to said element with the connector passing therethrough to enhance the ability of the prongs of said member to positively engage the exterior of said second bone fragment to the fullest extent possible, and wherein at least a lengthwise portion of the internal threading of said fastener is configured such that when the preselected compressive relationship is established between the fasteners the external threading on the connector is wedged against the internal threading of the first fastener to prevent inadvertent rotation of the connector thereby maintaining the preselected compressive relationship between the fasteners and the bone fragments connected thereto.

47. A multipiece interfragmentary fixation assembly for interconnecting first and second bone fragments, comprising:

a first bone screw having external threading axially extending away from a proximal end of and along a lengthwise portion of said first bone screw for anchoring said first bone screw to said first bone fragment;

a second bone screw having external threading along a lengthwise portion thereof for anchoring said second bone screw in said second bone fragment, said second bone screw defining an axial bore extending therethrough; and an elongated screw connector including an enlarged head portion that accommodates a driving tool and an elongated and externally threaded shank portion extending endwise through the axial bore of said second bone screw and into threaded engagement with internal threading of said first bone screw while the enlarged head portion of said connector operably engages with the second bone screw such that rotation of said connector draws the first and second bone screws and thereby the first and second bone fragments toward and into preselected compressive relationship relative to each other, and wherein at least a lengthwise portion of the internal threading of said first bone screw is configured such that when the preselected compressive relationship is established between the bone screws the external threading on the connector is wedged against the internal threading of the first bone screw to prevent inadvertent rotation of the connector thereby maintaining the preselected compressive relationship between the bone screws and the bone fragments connected thereto.

48. The interfragmentary fixation assembly according to claim 47 wherein the internal threading defined by said first bone screw further includes a wedge ramp at a root of each thread defined by said first bone screw.

49. The interfragmentary fixation assembly according to claim 1 wherein said retaining apparatus comprises a unidirectional thread form extending axially along the internal threading defined by said first elongated fastener such that crest areas of the external threading on said connector coact therewith in a manner preventing the connector from inadvertently rotating relative to said second fastener.

50. An interfragmentary fixation kit, comprising:

a collection of first axially elongated fasteners, each fastener in said collection having an elongated length that is different from the elongated length of another fastener in said collection, and with each fastener in said collection having external threading for anchoring said first fastener into a first bone fragment, and wherein each fastener in said collection of fasteners having a coaxial bore extending therethrough with internal uniformally pitched threading extending the length of said bore;

a series of second fasteners, with each fastener in said series of fasteners being adapted for attachment in non-movable relation relative to a second bone fragment and having a different configuration than the other fasteners in said series of second fasteners;

a set of elongated connectors, each connector in said set of connectors having a head portion that accommodates a driving tool and an elongated lengthwise shank portion having external uniformly pitched threading corresponding to the internal threading of each fastener in said collection of first fasteners, and wherein the length of the shank portion of each connector in said set of connectors varies from one another, and wherein the shank portion of each connector in said set of connectors is configured to extend endwise through each fastener in said series of second fasteners and into threaded engagement with the internal threading of a fastener chosen from said collection of first fasteners while the head portion of said connector is adapted to operably engage with a second fastener chosen from said series of second fasteners such that rotation of the connector draws the first and second fasteners chosen from said collection of first fasteners and the series of second fasteners into a predetermined compressive relationship relative to each other and thereby drawing the bone fragments attached to the respective fasteners into a predetermined compressive relationship relative to each other.

\* \* \* \* \*